(12) United States Patent
Smith et al.

(10) Patent No.: US 12,128,183 B2
(45) Date of Patent: *Oct. 29, 2024

(54) PATIENT INTERFACE AND HEADGEAR

(71) Applicant: Fisher & Paykel Healthcare Limited, Auckland (NZ)

(72) Inventors: Daniel John Smith, Auckland (NZ); Brett John Huddart, Auckland (NZ); Matthew James Adams, Tauranga (NZ); Nicholas Alexander Hobson, Auckland (NZ); Timothy James Beresford Sharp, Auckland (NZ); Roheet Patel, Auckland (NZ); Gregory James Olsen, Auckland (NZ); Matthew Roger Stephenson, Auckland (NZ); Troy Barsten, Manukau (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/528,296

(22) Filed: Dec. 4, 2023

(65) Prior Publication Data

US 2024/0165360 A1 May 23, 2024

Related U.S. Application Data

(63) Continuation of application No. 16/053,471, filed on Aug. 2, 2018, now Pat. No. 11,865,263, which is a
(Continued)

(51) Int. Cl.
*A61M 16/00* (2006.01)
*A61M 16/06* (2006.01)
*A61M 16/08* (2006.01)

(52) U.S. Cl.
CPC .... *A61M 16/0683* (2013.01); *A61M 16/0057* (2013.01); *A61M 16/06* (2013.01);
(Continued)

(58) Field of Classification Search
CPC .... A61M 16/06–0655; A61M 16/0683; A62B 18/02; A62B 18/025; A62B 18/04; A62B 18/06; A62B 18/08; A62B 18/084
See application file for complete search history.

(56) References Cited

U.S. PATENT DOCUMENTS

| 301,111 A | 7/1884 | Genese |
| 472,238 A | 4/1892 | Van Orden |

(Continued)

FOREIGN PATENT DOCUMENTS

| CA | 996301 | 9/1976 |
| CA | 1311662 | 12/1992 |

(Continued)

OTHER PUBLICATIONS cpap.com, InnoMed/Resp Care Bravo Nasal Pillow CPAP Mask with Headgear, (http://web.archive.org/web/*/https://www.cpap.com/productpage/bravo-nasal-interface/), downloaded Feb. 24, 2020, 5 pp.
(Continued)

*Primary Examiner* — LaToya M Louis
(74) *Attorney, Agent, or Firm* — Knobbe, Martens, Olson & Bear, LLP

(57) ABSTRACT

Patient interface components and/or associated head gear and adjustment systems improve sealing and/or patient comfort and/or ease of use. The interface includes an inflating or ballooning seal. The headgear assembly can be connected to the interface with an elastic component and an inelastic component. The elastic component enabling a course fitting of the interface to the patient and the inelastic
(Continued)

component enabling a final fitting of the interface to the patient.

10 Claims, 23 Drawing Sheets

Related U.S. Application Data continuation of application No. 13/518,713, filed as application No. PCT/IB2010/003466 on Dec. 22, 2010, now Pat. No. 10,065,010.

(60) Provisional application No. 61/289,641, filed on Dec. 23, 2009, provisional application No. 61/391,514, filed on Oct. 8, 2010.

(52) U.S. Cl.
CPC ..... *A61M 16/0616* (2014.02); *A61M 16/0816* (2013.01); *A61M 16/0825* (2014.02); *A61M 16/0858* (2014.02)

(56) References Cited

U.S. PATENT DOCUMENTS

| | | |
|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,364,104 A | 1/1921 | Geer |
| 1,635,545 A | 7/1927 | Drager |
| 1,942,442 A | 1/1934 | Motsinger |
| 2,199,690 A | 5/1940 | Bullard |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,390,233 A | 12/1945 | Akerman et al. |
| 2,508,050 A | 5/1950 | Valente |
| 2,586,851 A | 2/1952 | Monro et al. |
| 2,611,897 A | 9/1952 | Adams |
| 2,661,514 A | 12/1953 | Ada |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 3,045,672 A | 7/1962 | Croasdaile |
| 3,156,922 A | 11/1964 | Anderson |
| 3,295,529 A | 1/1967 | Corrigall et al. |
| 3,416,521 A | 12/1968 | Humphrey |
| 3,457,564 A | 7/1969 | Holloway |
| 3,490,452 A | 1/1970 | Greenfield |
| 3,500,474 A | 3/1970 | Austin |
| 3,530,031 A | 9/1970 | Loew |
| 3,792,702 A | 2/1974 | Delest |
| 3,834,682 A | 9/1974 | McPhee |
| 3,850,171 A | 11/1974 | Ball et al. |
| 3,887,968 A | 6/1975 | Lynam |
| 3,972,321 A | 8/1976 | Proctor |
| 3,990,757 A | 11/1976 | Gill |
| 3,992,720 A | 11/1976 | Nicolinas |
| 3,994,022 A | 11/1976 | Villari et al. |
| 4,051,556 A | 10/1977 | Davenport et al. |
| 4,062,068 A | 12/1977 | Davenport et al. |
| 4,090,510 A | 5/1978 | Segersten |
| D250,047 S | 10/1978 | Lewis et al. |
| D250,131 S | 10/1978 | Lewis et al. |
| 4,127,130 A | 11/1978 | Naysmith |
| D252,322 S | 7/1979 | Johnson |
| 4,167,185 A | 9/1979 | Lewis |
| 4,201,205 A | 5/1980 | Bartholomew |
| 4,266,540 A | 5/1981 | Panzik et al. |
| 4,278,082 A | 7/1981 | Blackmer |
| 4,288,891 A | 9/1981 | Boden |
| 4,313,437 A | 2/1982 | Martin |
| 4,328,605 A | 5/1982 | Hutchinson et al. |
| 4,354,488 A | 10/1982 | Bartos |
| 4,367,735 A | 1/1983 | Dali |
| 4,402,316 A | 9/1983 | Gadberry |
| 4,413,382 A | 11/1983 | Siegmann |
| 4,437,462 A | 3/1984 | Piljay |
| 4,453,292 A | 6/1984 | Bakker |
| 4,458,373 A | 7/1984 | Maslow |
| 4,477,928 A | 10/1984 | Graff |
| 4,606,077 A | 8/1986 | Phillips |
| D293,613 S | 1/1988 | Wingler |
| 4,734,940 A | 4/1988 | Galet et al. |
| 4,753,233 A | 6/1988 | Grimes |
| 4,782,832 A | 11/1988 | Trimble et al. |
| 4,817,596 A | 4/1989 | Gallet |
| 4,848,334 A | 7/1989 | Bellm |
| 4,853,275 A | 8/1989 | Tracy et al. |
| 4,856,508 A | 8/1989 | Tayebi |
| 4,915,105 A | 4/1990 | Lee |
| 4,941,467 A | 7/1990 | Takata |
| 4,944,310 A | 7/1990 | Sullivan |
| 4,947,488 A | 8/1990 | Ashinoff |
| D310,431 S | 9/1990 | Bellm |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,042,478 A | 8/1991 | Kopala et al. |
| D320,677 S | 10/1991 | Kumagai et al. |
| 5,052,084 A | 10/1991 | Braun |
| D321,419 S | 11/1991 | Wallace |
| 5,065,756 A | 11/1991 | Rapoport |
| 5,074,297 A | 12/1991 | Venegas |
| 5,094,236 A | 3/1992 | Tayebi |
| 5,113,857 A | 5/1992 | Dickerman et al. |
| 5,148,578 A | 9/1992 | Clarke et al. |
| 5,148,802 A | 9/1992 | Sanders et al. |
| 5,191,882 A | 3/1993 | Vogliano |
| 5,231,979 A | 8/1993 | Rose |
| 5,245,995 A | 9/1993 | Sullivan et al. |
| D340,317 S | 10/1993 | Cole |
| 5,269,296 A | 12/1993 | Landis et al. |
| D354,128 S | 1/1995 | Rinehart |
| D355,484 S | 2/1995 | Rinehart |
| 5,388,743 A | 2/1995 | Silagy |
| 5,438,979 A | 8/1995 | Johnson et al. |
| 5,477,852 A | 12/1995 | Landis et al. |
| 5,488,948 A | 2/1996 | Dubruille |
| 5,513,634 A | 5/1996 | Jackson |
| 5,529,062 A | 6/1996 | Byrd |
| 5,533,506 A | 7/1996 | Wood |
| 5,546,605 A | 8/1996 | Mallardi |
| 5,551,419 A | 9/1996 | Froehlich et al. |
| 5,566,395 A | 10/1996 | Nebeker |
| 5,595,174 A | 1/1997 | Gwaltney |
| 5,601,078 A | 2/1997 | Schaller et al. |
| D378,610 S | 3/1997 | Reischel et al. |
| 5,657,752 A | 8/1997 | Landis et al. |
| 5,724,965 A | 3/1998 | Handke et al. |
| 5,752,510 A | 5/1998 | Goldstein |
| 5,755,578 A | 5/1998 | Contant et al. |
| 5,774,901 A | 7/1998 | Minami |
| 5,884,624 A | 3/1999 | Barnett et al. |
| 5,921,239 A | 7/1999 | McCall et al. |
| 5,941,245 A | 8/1999 | Hannah et al. |
| 5,941,856 A | 8/1999 | Kovacs et al. |
| 6,017,315 A | 1/2000 | Starr et al. |
| 6,019,101 A | 2/2000 | Cotner et al. |
| 6,044,844 A | 4/2000 | Kwok et al. |
| 6,050,260 A | 4/2000 | Daniell et al. |
| 6,119,694 A | 9/2000 | Correa et al. |
| 6,192,886 B1 | 2/2001 | Rudolph |
| D440,302 S | 4/2001 | Wolfe |
| 6,256,798 B1 | 7/2001 | Egolf et al. |
| 6,272,690 B1 | 8/2001 | Carey et al. |
| 6,282,725 B1 | 9/2001 | Vanidestine, Jr. |
| 6,298,850 B1 | 10/2001 | Argraves |
| 6,338,342 B1 | 1/2002 | Fecteau et al. |

(56) References Cited

U.S. PATENT DOCUMENTS

| | | |
|---|---|---|
| 6,347,631 B1 | 2/2002 | Hansen et al. |
| D455,891 S | 4/2002 | Biedrzycki |
| 6,418,928 B1 | 7/2002 | Bordewick et al. |
| 6,422,238 B1 | 7/2002 | Lithgow |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,470,886 B1 | 10/2002 | Jestrabek-Hart |
| 6,478,026 B1 | 11/2002 | Wood |
| 6,491,034 B1 | 12/2002 | Gunaratnam et al. |
| 6,536,435 B1 | 3/2003 | Fecteau et al. |
| 6,561,188 B1 | 5/2003 | Ellis |
| 6,561,191 B1 | 5/2003 | Kwok |
| 6,581,594 B1 | 6/2003 | Drew et al. |
| 6,581,601 B2 | 6/2003 | Ziaee |
| 6,588,424 B2 | 7/2003 | Bardel |
| 6,631,718 B1 | 10/2003 | Lovell |
| 6,637,434 B2 | 10/2003 | Noble |
| 6,644,315 B2 | 11/2003 | Ziaee |
| 6,651,658 B1 | 11/2003 | Hill et al. |
| 6,659,102 B1 | 12/2003 | Sico |
| 6,662,803 B2 | 12/2003 | Gradon et al. |
| 6,679,257 B1 | 1/2004 | Robertson et al. |
| 6,679,265 B2 | 1/2004 | Strickland et al. |
| 6,772,761 B1 | 8/2004 | Rucker, Jr. |
| 6,851,425 B2 | 2/2005 | Jaffre et al. |
| 6,883,519 B2 | 4/2005 | Schmidtke et al. |
| 6,886,564 B2 | 5/2005 | Sullivan et al. |
| 6,892,729 B2 | 5/2005 | Smith et al. |
| 6,907,882 B2 | 6/2005 | Ging et al. |
| 6,951,218 B2 | 10/2005 | Gradon et al. |
| 7,004,165 B1 | 2/2006 | Salcido |
| D520,140 S | 5/2006 | Chaggares |
| 7,036,508 B2 | 5/2006 | Kwok |
| 7,062,795 B2 | 6/2006 | Skiba et al. |
| 7,066,179 B2 | 6/2006 | Eaton et al. |
| D526,094 S | 8/2006 | Chen |
| 7,096,864 B1 | 8/2006 | Mayer et al. |
| 7,096,867 B2 | 8/2006 | Smith et al. |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,318,437 B2 | 1/2008 | Gunaratnam et al. |
| 7,353,826 B2 | 4/2008 | Sleeper et al. |
| 7,353,827 B2 | 4/2008 | Geist |
| 7,814,911 B2 | 10/2010 | Bordewick et al. |
| 7,845,352 B2 | 12/2010 | Sleeper et al. |
| 7,861,715 B2 | 1/2011 | Jones et al. |
| 7,870,860 B2 | 1/2011 | McCormick et al. |
| 7,896,003 B2 | 3/2011 | Matula et al. |
| 7,913,692 B2 | 3/2011 | Kwok |
| 7,967,014 B2 | 6/2011 | Heidmann |
| 8,042,539 B2 | 10/2011 | Chandran et al. |
| 8,047,893 B2 | 11/2011 | Fenske |
| 8,074,651 B2 | 12/2011 | Bierman et al. |
| 8,104,473 B2 | 1/2012 | Woodard et al. |
| 8,132,270 B2 | 3/2012 | Lang et al. |
| 8,136,524 B2 | 3/2012 | Ging et al. |
| 8,209,995 B2 | 7/2012 | Kieling et al. |
| 8,297,285 B2 | 10/2012 | Henry et al. |
| 8,371,302 B2 | 2/2013 | Ging et al. |
| 8,443,807 B2 | 5/2013 | McAuley et al. |
| D686,313 S | 7/2013 | Matula et al. |
| 8,479,741 B2 | 7/2013 | McAuley et al. |
| 8,505,538 B2 | 8/2013 | Amarasinghe |
| 8,517,025 B2 | 8/2013 | Ho et al. |
| 8,522,785 B2 | 9/2013 | Berthon-Jones et al. |
| 8,573,201 B2 | 11/2013 | Rummery et al. |
| 8,596,271 B2 | 12/2013 | Matula, Jr. et al. |
| 8,596,274 B2 | 12/2013 | Hieber et al. |
| 8,631,793 B2 | 1/2014 | Omura et al. |
| 8,636,005 B2 | 1/2014 | Gradon et al. |
| 8,636,007 B2 | 1/2014 | Rummery et al. |
| 8,636,008 B2 | 1/2014 | Flory et al. |
| 8,757,157 B2 | 6/2014 | Price et al. |
| 8,783,257 B2 | 7/2014 | McAuley et al. |
| 8,794,239 B2 | 8/2014 | Gunaratnam |
| 8,857,435 B2 | 10/2014 | Matula, Jr. et al. |
| 8,915,251 B2 | 12/2014 | Lubke et al. |
| 8,997,742 B2 | 4/2015 | Moore et al. |
| 9,032,955 B2 | 5/2015 | Lubke et al. |
| 9,044,564 B2 | 6/2015 | Dravitzki et al. |
| 9,138,555 B2 | 9/2015 | McAuley et al. |
| 9,149,596 B2 | 10/2015 | Valcic et al. |
| 9,265,909 B2 | 2/2016 | Ho et al. |
| 9,302,065 B2 | 4/2016 | Smith et al. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,480,809 B2 | 11/2016 | Guney et al. |
| 9,517,320 B2 | 12/2016 | Barlow et al. |
| 9,550,038 B2 | 1/2017 | McAuley et al. |
| 9,592,336 B2 | 3/2017 | Nielsen et al. |
| 9,656,038 B2 | 5/2017 | Rummery et al. |
| 9,744,385 B2 | 8/2017 | Henry |
| 9,782,554 B2 | 10/2017 | Mazzone et al. |
| 9,878,118 B2 | 1/2018 | Formica |
| D810,277 S | 2/2018 | Amarasinghe |
| 9,884,160 B2 | 2/2018 | McAuley |
| 9,901,700 B2 | 2/2018 | McAuley et al. |
| 9,925,349 B2 | 3/2018 | Jablonski |
| 9,974,914 B2 | 5/2018 | McAuley |
| 9,993,606 B2 | 6/2018 | Gibson et al. |
| 10,039,665 B2 | 8/2018 | Blaszczykiewicz et al. |
| 10,065,010 B2 | 9/2018 | Smith et al. |
| 10,071,217 B2 | 9/2018 | Grashow |
| 10,080,856 B2 | 9/2018 | McLaren |
| 10,207,072 B2 | 2/2019 | Dunn et al. |
| 10,279,138 B2 | 5/2019 | Ovzinsky |
| 10,456,546 B2 | 10/2019 | McLaren et al. |
| 10,646,680 B2 | 5/2020 | Huddart et al. |
| 10,675,428 B2 | 6/2020 | Guney et al. |
| 10,792,451 B2 | 10/2020 | Allan et al. |
| 10,828,449 B2 | 11/2020 | Higgins et al. |
| 10,828,452 B2 | 11/2020 | Huddart et al. |
| 10,874,814 B2 | 12/2020 | Huddart et al. |
| 11,331,449 B2 | 5/2022 | McLaren et al. |
| 11,419,999 B2 | 8/2022 | Patel et al. |
| 11,607,518 B2 | 3/2023 | Hammer et al. |
| 11,648,365 B2 | 5/2023 | Huddart et al. |
| 11,701,486 B2 | 7/2023 | Mashal et al. |
| 11,752,292 B2 | 9/2023 | McLaren et al. |
| 11,806,452 B2 | 11/2023 | McLaren et al. |
| 11,813,384 B2 | 11/2023 | Huddart et al. |
| 11,819,620 B2 | 11/2023 | Hammer |
| 11,865,263 B2 | 1/2024 | Smith et al. |
| 11,878,119 B2 | 1/2024 | McLaren et al. |
| 2002/0005198 A1 | 1/2002 | Kwok et al. |
| 2002/0020416 A1 | 2/2002 | Namey |
| 2002/0046755 A1 | 4/2002 | Voss |
| 2002/0052568 A1 | 5/2002 | Houser et al. |
| 2002/0053347 A1 | 5/2002 | Ziaee |
| 2002/0059935 A1 | 5/2002 | Wood |
| 2002/0096178 A1 | 7/2002 | Ziaee |
| 2002/0157668 A1 | 10/2002 | Bardel |
| 2003/0005933 A1 | 1/2003 | Izuchukwu |
| 2003/0051732 A1 | 3/2003 | Smith et al. |
| 2003/0079749 A1 | 5/2003 | Strickland et al. |
| 2003/0084903 A1 | 5/2003 | Fecteau et al. |
| 2003/0111080 A1 | 6/2003 | Olsen et al. |
| 2003/0121519 A1 | 7/2003 | Estes et al. |
| 2003/0164170 A1 | 9/2003 | Drew et al. |
| 2003/0172936 A1 | 9/2003 | Wilkie et al. |
| 2003/0196656 A1 | 10/2003 | Moore |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2004/0067333 A1 | 4/2004 | Amarasinghe |
| 2004/0211427 A1 | 10/2004 | Jones et al. |
| 2004/0226566 A1 | 11/2004 | Gunaratnam et al. |
| 2005/0011524 A1 | 1/2005 | Thomlinson et al. |
| 2005/0016067 A1 | 1/2005 | Pettit |

(56) References Cited

U.S. PATENT DOCUMENTS

| | | |
|---|---|---|
| 2005/0028822 A1 | 2/2005 | Sleeper et al. |
| 2005/0033247 A1 | 2/2005 | Thompson |
| 2005/0066976 A1 | 3/2005 | Wondka |
| 2005/0076913 A1 | 4/2005 | Ho et al. |
| 2005/0098183 A1 | 5/2005 | Nash et al. |
| 2005/0150497 A1 | 7/2005 | Eifler et al. |
| 2005/0161049 A1 | 7/2005 | Wright |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0262619 A1 | 12/2005 | Musal et al. |
| 2006/0060200 A1 | 3/2006 | Ho et al. |
| 2006/0081250 A1 | 4/2006 | Bordewick et al. |
| 2006/0096596 A1 | 5/2006 | Occhialini et al. |
| 2006/0107958 A1 | 5/2006 | Sleeper |
| 2006/0113147 A1 | 6/2006 | Harris |
| 2006/0118117 A1 | 6/2006 | Berthon-Jones et al. |
| 2006/0124131 A1 | 6/2006 | Chandran |
| 2006/0137690 A1 | 6/2006 | Gunaratnam et al. |
| 2006/0174887 A1 | 8/2006 | Chandran et al. |
| 2006/0174892 A1 | 8/2006 | Leksutin et al. |
| 2006/0196510 A1 | 9/2006 | McDonald et al. |
| 2006/0196511 A1 | 9/2006 | Lau et al. |
| 2006/0237018 A1 | 10/2006 | McAuley et al. |
| 2007/0000492 A1 | 1/2007 | Hansel et al. |
| 2007/0010786 A1 | 1/2007 | Casey et al. |
| 2007/0089749 A1 | 4/2007 | Ho et al. |
| 2007/0125385 A1 | 6/2007 | Ho et al. |
| 2007/0125387 A1 | 6/2007 | Zollinger et al. |
| 2007/0130663 A1 | 6/2007 | Lang et al. |
| 2007/0137653 A1 | 6/2007 | Wood |
| 2007/0163600 A1 | 7/2007 | Hoffman |
| 2007/0169777 A1 | 7/2007 | Amarasinghe et al. |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0235033 A1 | 10/2007 | Reier et al. |
| 2007/0295335 A1 | 12/2007 | Nashed |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0052806 A1 | 3/2008 | McDaniel |
| 2008/0053450 A1 | 3/2008 | Van Kerkwyk et al. |
| 2008/0060648 A1 | 3/2008 | Thornton et al. |
| 2008/0060653 A1 | 3/2008 | Hallet et al. |
| 2008/0060657 A1 | 3/2008 | McAuley et al. |
| 2008/0065015 A1 | 3/2008 | Fiser |
| 2008/0083412 A1 | 4/2008 | Henry et al. |
| 2008/0092906 A1 | 4/2008 | Gunaratnam et al. |
| 2008/0099024 A1 | 5/2008 | Gunaratnam et al. |
| 2008/0110464 A1 | 5/2008 | Davidson et al. |
| 2008/0134480 A1 | 6/2008 | Shiue |
| 2008/0196728 A1 | 8/2008 | Ho |
| 2008/0230068 A1 | 9/2008 | Rudolph |
| 2008/0230069 A1 | 9/2008 | Valcic et al. |
| 2008/0264422 A1 | 10/2008 | Fishman |
| 2008/0302366 A1 | 12/2008 | McGinnis et al. |
| 2008/0314388 A1 | 12/2008 | Brambilla et al. |
| 2009/0000624 A1 | 1/2009 | Lee et al. |
| 2009/0014007 A1 | 1/2009 | Brambilla et al. |
| 2009/0032026 A1 | 2/2009 | Price et al. |
| 2009/0044808 A1 | 2/2009 | Guney et al. |
| 2009/0044809 A1 | 2/2009 | Welchel et al. |
| 2009/0120442 A1 | 5/2009 | Ho |
| 2009/0133697 A1 | 5/2009 | Kwok et al. |
| 2009/0145429 A1 | 6/2009 | Ging et al. |
| 2009/0173349 A1 | 7/2009 | Hernandez et al. |
| 2009/0178680 A1 | 7/2009 | Chang |
| 2009/0183739 A1 | 7/2009 | Wondka |
| 2009/0211583 A1 | 8/2009 | Carroll |
| 2009/0250060 A1 | 10/2009 | Hacke et al. |
| 2009/0320187 A1 | 12/2009 | Petzl et al. |
| 2010/0000538 A1 | 1/2010 | Edwards et al. |
| 2010/0000544 A1 | 1/2010 | Blaszczykiewicz et al. |
| 2010/0018534 A1 | 1/2010 | Veliss et al. |
| 2010/0037897 A1 | 2/2010 | Wood |
| 2010/0154798 A1 | 6/2010 | Henry et al. |
| 2010/0224199 A1 | 9/2010 | Smith et al. |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0307502 A1 | 12/2010 | Rummery et al. |
| 2010/0313532 A1 | 12/2010 | Stjernfelt et al. |
| 2010/0313891 A1 | 12/2010 | Veliss et al. |
| 2010/0319700 A1 | 12/2010 | Ng et al. |
| 2011/0048425 A1 | 3/2011 | Chang |
| 2011/0191938 A1 | 8/2011 | Elliott |
| 2011/0197341 A1 | 8/2011 | Formica |
| 2011/0220113 A1 | 9/2011 | Newman |
| 2011/0247628 A1 | 10/2011 | Ho |
| 2011/0259335 A1 | 10/2011 | Sullivan |
| 2011/0265791 A1 | 11/2011 | Ging et al. |
| 2011/0265796 A1 | 11/2011 | Amarasinghe et al. |
| 2012/0067349 A1 | 3/2012 | Barlow et al. |
| 2012/0125339 A1 | 5/2012 | Ho et al. |
| 2012/0132209 A1 | 5/2012 | Rummery |
| 2012/0138063 A1 | 6/2012 | Eves et al. |
| 2012/0174355 A1 | 7/2012 | Fraze |
| 2012/0222680 A1 | 9/2012 | Eves et al. |
| 2012/0285464 A1 | 11/2012 | Birch et al. |
| 2012/0304999 A1 | 12/2012 | Swift et al. |
| 2013/0000648 A1 | 1/2013 | Madaus et al. |
| 2013/0139822 A1 | 6/2013 | Gibson |
| 2013/0152918 A1 | 6/2013 | Rummery et al. |
| 2013/0152937 A1 | 6/2013 | Jablonski |
| 2013/0160769 A1 | 6/2013 | Ng et al. |
| 2013/0220327 A1 | 8/2013 | Barlow et al. |
| 2013/0247916 A1 | 9/2013 | Symons |
| 2013/0319421 A1 | 12/2013 | Hitchcock et al. |
| 2014/0026888 A1 | 1/2014 | Matula |
| 2014/0026890 A1 | 1/2014 | Haskard et al. |
| 2014/0083428 A1 | 3/2014 | Rothermel et al. |
| 2014/0102456 A1 | 4/2014 | Ovizinsky |
| 2014/0137870 A1 | 5/2014 | Barlow |
| 2014/0158726 A1 | 6/2014 | Malara |
| 2014/0166019 A1 | 6/2014 | Ho et al. |
| 2014/0190486 A1 | 7/2014 | Dunn et al. |
| 2014/0209098 A1 | 7/2014 | Dunn |
| 2014/0209298 A1 | 7/2014 | Baldasaro et al. |
| 2014/0216452 A1 | 8/2014 | Miller et al. |
| 2014/0305439 A1 | 10/2014 | Chodkowski |
| 2014/0358054 A1 | 12/2014 | Capra |
| 2015/0000615 A1 | 1/2015 | Imran et al. |
| 2015/0005685 A1 | 1/2015 | Chetlapalli et al. |
| 2015/0028519 A1 | 1/2015 | Lang et al. |
| 2015/0033457 A1 | 2/2015 | Tryner et al. |
| 2015/0051000 A1 | 2/2015 | Henn |
| 2015/0090268 A1 | 4/2015 | Madaus et al. |
| 2015/0128953 A1 | 5/2015 | Formica et al. |
| 2015/0151070 A1 | 6/2015 | Capra et al. |
| 2015/0190262 A1 | 7/2015 | Capra et al. |
| 2015/0202397 A1 | 7/2015 | Pastoor |
| 2015/0217150 A1 | 8/2015 | Harris |
| 2015/0285337 A1 | 10/2015 | Dingley et al. |
| 2015/0290415 A1 | 10/2015 | Dunn |
| 2016/0022944 A1 | 1/2016 | Chodkowski et al. |
| 2016/0038707 A1 | 2/2016 | Allan et al. |
| 2016/0045700 A1 | 2/2016 | Amarasinghe |
| 2016/0082214 A1 | 3/2016 | Barlow et al. |
| 2016/0166793 A1 | 6/2016 | McLaren et al. |
| 2016/0178027 A1 | 6/2016 | Wetzel |
| 2016/0278463 A1 | 9/2016 | Stevenson |
| 2016/0375214 A1 | 12/2016 | Chodkowski et al. |
| 2017/0136269 A1 | 5/2017 | Jacotey et al. |
| 2017/0182276 A1 | 6/2017 | Hammer |
| 2017/0189636 A1 | 7/2017 | Gibson et al. |
| 2017/0216548 A1 | 8/2017 | Gerhardt |
| 2018/0214655 A1 | 8/2018 | Kooij et al. |
| 2018/0264218 A1 | 9/2018 | Chodkowski |
| 2019/0111227 A1 | 4/2019 | Veliss et al. |
| 2019/0151592 A1 | 5/2019 | Bornholdt |
| 2020/0230343 A1 | 7/2020 | Sims et al. |
| 2020/0338294 A1 | 10/2020 | McLaren et al. |

(56) References Cited

U.S. PATENT DOCUMENTS

| | | |
|---|---|---|
| 2022/0126049 A1 | 4/2022 | Amarasinghe |
| 2023/0347090 A1 | 11/2023 | Huddart et al. |
| 2024/0024606 A1 | 1/2024 | McLaren et al. |
| 2024/0033461 A1 | 2/2024 | Felix et al. |
| 2024/0077763 A1 | 3/2024 | Yoon et al. |
| 2024/0139456 A1 | 5/2024 | Freestone |
| 2024/0181194 A1 | 6/2024 | Hammer |

FOREIGN PATENT DOCUMENTS

| | | |
|---|---|---|
| CN | 2172538 | 7/1994 |
| CN | 1784250 | 6/2006 |
| CN | 1901963 A | 1/2007 |
| CN | 201033204 | 3/2008 |
| CN | 201171846 | 12/2008 |
| CN | 101432039 A | 5/2009 |
| CN | 100502972 C | 6/2009 |
| CN | 101516427 | 8/2009 |
| CN | 202822396 U | 3/2013 |
| DE | 895692 | 11/1953 |
| DE | 2706284 | 8/1978 |
| DE | 3122034 | 12/1982 |
| DE | 3907428 | 9/1990 |
| DE | 10254399 | 6/2004 |
| DE | 102006011151 | 9/2007 |
| EP | 0 350 322 | 1/1990 |
| EP | 0 401 307 | 8/1995 |
| EP | 0 879 565 | 11/1998 |
| EP | 0 982 049 | 3/2000 |
| EP | 1 187 650 | 12/2005 |
| EP | 2 130 563 | 12/2009 |
| EP | 2 517 757 | 10/2012 |
| EP | 2 022 528 | 3/2016 |
| FR | 2390116 | 3/1938 |
| FR | 2618340 | 11/1970 |
| FR | 825960 | 1/1989 |
| FR | 2658725 | 8/1991 |
| FR | 2749176 | 12/1997 |
| FR | 2804421 | 8/2001 |
| GB | 190224431 | 12/1902 |
| GB | 339522 | 12/1930 |
| GB | 826198 | 12/1959 |
| GB | 880824 | 10/1961 |
| GB | 1467828 | 3/1977 |
| GB | 2133275 | 7/1984 |
| GB | 2188236 | 9/1987 |
| GB | 1211268 | 4/2000 |
| GB | 2478305 | 9/2011 |
| GB | 2491227 | 11/2012 |
| GB | 2553475 | 3/2018 |
| JP | S46-12114 | 4/1971 |
| JP | 46-016719 | 6/1971 |
| JP | S55-89072 | 7/1980 |
| JP | 368861 U | 5/2000 |
| JP | 2004-016488 | 1/2004 |
| JP | 2003-053874 | 9/2004 |
| JP | 2009-125306 | 6/2009 |
| JP | 2010-090973 | 4/2010 |
| JP | 2000-102624 | 5/2013 |
| JP | 2018-127729 | 8/2018 |
| KR | 10-2011-0028950 | 3/2011 |
| NZ | 585295 | 12/2011 |
| WO | WO 95/12432 | 5/1995 |
| WO | WO 97/32494 | 9/1997 |
| WO | WO 98/003225 | 1/1998 |
| WO | WO 98/018514 | 5/1998 |
| WO | WO 99/04842 | 2/1999 |
| WO | WO 99/058181 | 11/1999 |
| WO | WO 00/50122 | 8/2000 |
| WO | WO 00/069497 | 11/2000 |
| WO | WO 00/074758 | 12/2000 |
| WO | WO 01/041854 | 6/2001 |
| WO | WO 01/097892 | 12/2001 |
| WO | WO 02/44749 | 6/2002 |
| WO | WO 02/047749 | 6/2002 |
| WO | WO 02/074372 | 9/2002 |
| WO | WO 04/041341 | 5/2004 |
| WO | WO 04/073778 | 9/2004 |
| WO | WO 05/021075 | 3/2005 |
| WO | WO 05/032634 | 4/2005 |
| WO | WO 05/046776 | 5/2005 |
| WO | WO 05/051468 | 6/2005 |
| WO | WO 05/063328 | 7/2005 |
| WO | WO 05/118042 | 12/2005 |
| WO | WO 05/123166 | 12/2005 |
| WO | WO 06/130903 | 12/2006 |
| WO | WO 06/138416 | 12/2006 |
| WO | WO 07/022562 | 3/2007 |
| WO | WO 07/041786 | 4/2007 |
| WO | WO 07/068044 | 6/2007 |
| WO | WO 07/125487 | 11/2007 |
| WO | WO 07/147088 | 12/2007 |
| WO | WO 08/007985 | 1/2008 |
| WO | WO 08/060295 | 5/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/038918 | 3/2009 |
| WO | WO 09/052560 | 4/2009 |
| WO | WO 09/059353 | 5/2009 |
| WO | WO 09/092057 | 7/2009 |
| WO | WO 09/108995 | 9/2009 |
| WO | WO 09/139647 | 11/2009 |
| WO | WO 09/148956 | 12/2009 |
| WO | WO 10/066004 | 6/2010 |
| WO | WO 10/131189 | 11/2010 |
| WO | WO 10/139014 | 12/2010 |
| WO | WO 11/072739 | 6/2011 |
| WO | WO 11/077254 | 6/2011 |
| WO | WO 11/112401 | 9/2011 |
| WO | WO 12/07300 | 1/2012 |
| WO | WO 12/045127 | 4/2012 |
| WO | WO 12/069951 | 5/2012 |
| WO | WO 12/071300 | 5/2012 |
| WO | WO 12/143822 | 10/2012 |
| WO | WO 12/177152 | 12/2012 |
| WO | WO 13/006913 | 1/2013 |
| WO | WO 13/026091 | 2/2013 |
| WO | WO 13/026092 | 2/2013 |
| WO | WO 13/064930 | 5/2013 |
| WO | WO 14/020469 | 2/2014 |
| WO | WO 14/025267 | 2/2014 |
| WO | WO 14/031673 | 2/2014 |
| WO | WO 14/075141 | 5/2014 |
| WO | WO 14/077708 | 5/2014 |
| WO | WO 14/110622 | 7/2014 |
| WO | WO 14/110626 | 7/2014 |
| WO | WO 14/129913 | 8/2014 |
| WO | WO 14/175752 | 10/2014 |
| WO | WO 14/175753 | 10/2014 |
| WO | WO 15/033287 | 3/2015 |
| WO | WO 15/043229 | 4/2015 |
| WO | WO 15/070289 | 5/2015 |
| WO | WO 15/079396 | 6/2015 |
| WO | WO 15/083060 | 6/2015 |
| WO | WO 15/151019 | 10/2015 |
| WO | WO 15/187986 | 12/2015 |
| WO | WO 16/043603 | 3/2016 |
| WO | WO 17/030447 | 2/2017 |
| WO | WO 17/059476 | 4/2017 |
| WO | WO 17/150990 | 9/2017 |
| WO | WO 17/158474 | 9/2017 |
| WO | WO 17/158544 | 9/2017 |
| WO | WO 17/160166 | 9/2017 |
| WO | WO 17/216708 | 12/2017 |
| WO | WO 19/003094 | 1/2019 |

OTHER PUBLICATIONS

Pad A Cheek, LLC, Sleep apnea can make beautiful sleep elusive, (http://web.archive.org/web/20070701000000*/http://www.padacheek.com/;Wayback Machine), downloaded Feb. 24, 2020, 3 pp.

(56) References Cited

OTHER PUBLICATIONS

Philips Respironics "System One Heated Humidifier—User Manual", 2011, pp. 1-16, [retrieved on Nov. 25, 2013] from the internet: URL: http://www.cpapxchange.com/cpap-machines-biap- machines/system-one-60-series-cpap-humidifier-manual.pdf.
Langnau, Jan. 2, 2012, Tips on Clips Part 2: Make it Snappy, https://www.makepartsfast.com/tips-on-clips-part-2-make-it-snappy/, 9 pp.

PATIENT INTERFACE AND HEADGEAR

CROSS-REFERENCE TO RELATED APPLICATIONS

This application is a continuation application of U.S. application Ser. No. 16/053,471, filed Aug. 2, 2018, which is a continuation application of U.S. application Ser. No. 13/518,713, filed on Jun. 22, 2012, now U.S. Pat. No. 10,065,010, issued on Sep. 4, 2018, which is a national stage application under 35 U.S.C. § 371(c) of PCT Application No. PCT/IB10/03466, filed on Dec. 22, 2010, which claims the priority benefit under 35 U.S.C. § 119(d) of U.S. Provisional Application No. 61/289,641, filed on Dec. 23, 2009, and of U.S. Provisional Application No. 61/391,514, filed on Oct. 8, 2010, each of which is hereby incorporated by reference in its entirety.

BACKGROUND OF THE INVENTION

Field of the Invention

The present invention relates to improved patient interface components, particularly but not solely, for use in delivering artificial respiration therapy to patients. In particular, the invention relates to interfaces and to headgear that is used to secure interfaces to a patient.

Description of the Related Art

In the art of respiration devices, there are a variety of respiratory interfaces that cover the nose and/or mouth of a patient in order to provide a seal around the nasal and/or oral areas of the face such that gas may be provided at positive pressure within the interface for consumption by the patient.

The interfaces must provide an effective seal against the face to reduce the likelihood of significant leakage of the respiratory gas being supplied. In many interfaces, a good seal often is attained only with considerable discomfort for the patient, with temporary success and/or with significant time spent fitting the interface to the patient.

With respect to the discomfort for the patient, this problem is most crucial in acute care medical environments. In such environments, the patient will be required to wear the interface continuously for hours or perhaps even days. If significant discomfort is experienced, the patient will not willingly tolerate the mask for the desired long durations.

In many constructions, even a good seal can be temporary due to an inability to seal effectively when the face of the patient becomes distorted. For example, when the patient is sleeping on a side, one side of the headgear may be pulled tight while the other side becomes loose. This asymmetric loading can twist the axis of the interface relative to the axis of the head due to the net torque from the headgear and any associated breathing tube. The twisting of the axis can result in leakage on one side of the interface. In addition, a side-sleeping patient may also distort the facial contours (e.g., in the nasal area) around the seal, which may lead to further leakage.

Finally, in acute care settings, the speed with which respiratory treatment can be established is important. Accordingly, with some headgear configurations, the ability to rapidly establish a satisfactory seal has been identified as an area in which current configurations could be improved.

SUMMARY OF THE INVENTION

It has been found that improvements can be made to both sealing of the interface to the face of the patient and securing the interface to the face of the patient with headgear.

Because the interface may be worn for prolonged periods in a hospital for example or when sleeping, comfort preferably should be maximized while also maintaining sufficient pressure on the interface to provide proper location and an adequate seal against the face, thereby reducing the likelihood of significant leaks. For example, any leakage preferably is less than about 15 L/min. In a hospital setting, it is also possible that a patient will not be conscious while wearing the interface. Added comfort can also increase the patient's compliance with treatment and results in better outcomes generally.

It is preferable that the interface and associated headgear is as easy as possible to put on and take off correctly. In particular, it is also desirable for a single headgear design to accommodate a wide range of patient head sizes, shapes and hair style types, while still being simple to work. This is especially the case in a hospital setting where staff are regularly fitting and removing patient interfaces and associated head gear. Desirably, the interface also accommodates various facial shapes and sizes.

From the patient's viewpoint, the interface also should provide certain advantages where possible. For example, the patient may desire to wear glasses such that clearance above the nasal region can be important. In addition, the patient may desire to talk to people and, therefore, advances in the interface that can improve the ability to be heard without removing the interface can be important. Furthermore, the patient generally prefers to not have the interface intrude in a significant manner into the field of vision. Thus, a lower profile interface is desirable. Finally, from a comfort standpoint, the patient would desire an interface and headgear configuration that reduces gas leaks that are directed toward the eyes and that has a reduced smell of materials while also having a lower noise level.

Clinically, the healthcare provider desires that the well-sealing interface provide generally even interface pressure distribution on the skin to reduce the likelihood of point loading or excessive pressure gradients. Such a feature can reduce the likelihood of irritation to the skin of the patient. In addition, flushing of carbon dioxide to reduce the likelihood of rebreathing of carbon dioxide is desirable.

It is an object of the present invention to provide an improved patient interface and/or an improved headgear arrangement for securing a patient interface to a patient or to at least provide the public and medical profession a useful choice.

In this specification where reference has been made to patent specifications, other external documents, or other sources of information, this is generally for the purpose of providing a context for discussion. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of." When interpreting each statement in this specification that includes the term "comprising," features other than that or those prefaced by the term may also be present. Related terms such as "comprise" and "comprises" are to be interpreted in the same manner.

Certain embodiments of this invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

In one aspect, the present invention may broadly be said to consist in an interface comprising a mask, headgear, an adjustment line, an upper sliding connection between the adjustment line and an upper portion of the mask, a lower sliding connection between the adjustment line and a lower portion of the mask, a left sliding connection between the adjustment line and a left side portion of the headgear, a right sliding connection between the adjustment line and a right side portion of the headgear, the adjustment line thus forming connections between the left side portion of the headgear and the upper and lower portions of the mask and the right side portion of the headgear and the upper and lower portions of the mask, and a clasp, clamp or other adjustment mechanism for securing at least a first portion of the adjustment line relative to a second portion of the adjustment line (either directly or indirectly) with the path of the line between the first and second portions including the upper, lower, left and right side connections, such that the length of the path of the adjustment line may be altered.

According to a further aspect, the adjustment line passes across the outside of either the upper portion of the mask, the lower portion of the mask or both.

According to a further aspect, the headgear includes upper left side attachment portion and lower left side attachment portion, upper right side attachment portion and lower right side attachment portion, and the adjustment line passes through the upper and lower attachment portions of each of the left side and right side portions of the headgear.

According to a further aspect, the interface includes at least two sliding connections between the attachment line and the lower mask portion.

According to a further aspect, the interface at least two sliding connections between the attachment line and the upper mask portion.

According to a further aspect, the interface a clasp holding the adjustment line at two points such that the adjustment line forms a closed loop.

According to a further aspect, the first and second portions of the adjustment line pass through the clasp, and drawing either or both ends through the clasp reduces the length of the loop, and the sliding connections to the mask and headgear distribute this tightening around the loop.

According to a further aspect, the clasp, clamp or adjustment mechanism releases the adjustment line or allows the adjustment line to pass through it upon application of tension on the adjustment line above a threshold (the threshold limiting the tension on the adjustment line to a useful range of tension).

According to a further aspect, the locations of the sliding connections on the mask are such that the projected area of the mask above the upper sliding connection and the projected area of the mask below the lower sliding connection are substantially equal.

According to a further aspect, the adjustment line is substantially non extensile.

According to a further aspect, one or more said sliding connections associated with said mask includes a pulley wheel engaging with said adjustment line.

According to a further aspect, one or more said sliding connections associated with said headgear includes a pulley wheel engaging with said adjustment line.

According to a further aspect, said adjustment line is wholly or partially enclosed in a tube allowing said closed loop.

According to a further aspect, said clasp, clamp or other adjustment mechanism is:
a) a jam cleat
b) a cam cleat
c) linear ratchet ski binding type mechanism
d) ratchet and release adjustment wheel.

In another aspect, the present invention may broadly be said to consist in an interface for supplying gases to a patient comprising a seal for contacting the user's face on an inside side, the seal contacting the face around the mouth and nose of the wearer, wherein the outside surface of the interface being shaped to include a substantial reproduction of at least one human facial feature.

According to a further aspect, the outside surface of the interface includes the reproduction of a human nose.

According to a further aspect, the seal is part of a seal member formed from a soft compliant material, the interface includes a stiffer support member forming part of the outside surface of the interface and at least one facsimile of a human facial feature is formed as part of the seal member.

According to a further aspect, the support member is flexible and the periphery of the support member can conform to the facial contour of the wearer.

According to a further aspect, the seal member includes a seal portion which contacts the user's face and an enclosing portion which contacts the inside surface of the supporting member, a seal portion contacting the inside surface of the supporting member being fully or substantially complete but for an aperture sufficient to supply breathing gases.

According to a further aspect, the interface includes a connector sealed to the aperture of the seal member.

According to a further aspect, the outer perimeter of the support member includes a scallop or notch and the human facial feature of the seal member protrudes through the notch.

According to a further aspect, the seal member includes a radially inward projecting sealing flap around substantially the entire perimeter of the seal member, wherein the sealing flap also contacts the face first during donning of the interface.

According to a further aspect, the support member includes attachments for headgear for supporting the interface on a user.

According to a further aspect, the support member is ergonomically contoured for holding in the hand.

According to a further aspect, the facial feature comprises a human nose, the seal member extends to cover the wearer's nose and upper cheeks, cheekbones and the upper perimeter of the support member extends transversely across the upper lip below the nose, upwardly alongside each nostril and transversely away from the nose at each side, above the level of the nostrils.

According to a further aspect, the support body includes an opening substantially aligned with the aperture of the seal member, the opening of the support body being larger than aperture of the seal member.

According to a further aspect, the support member and the seal member each include a chin portion, at least the chin portion of the seal member extending under the chin of the wearer in use.

According to a further aspect, said seal is an inflating seal.

According to a further aspect, said stiffness support member includes a bridge portion extending at least partially over said seal member in the region of the bridge of said reproduction of a human nose.

According to a further aspect, said interface further includes a breathing tube connection port, and wherein said connection port is fitted to said seal member.

In another aspect, the present invention may broadly be said to consist in a respiratory mask comprising a soft compliant seal member adapted to cover a users nose and mouth, and contact a users face to seal along at least a sealing edge, a support member adjacent to and supporting said seal member, wherein at least an outer portion of said support member comprises a plurality of displaceable members movable with respect to at least an inner portion of said support member.

According to a further aspect, said inner portion of said support member includes a hub portion connected to said seal and said displaceable members are cantilevered such that they branch outward from said inner hub toward said peripheral sealing edge of said seal member.

According to a further aspect, said displaceable members are movable with respect to one another.

According to a further aspect, said respiratory mask includes a further support member adjacent to and supporting said support member or said seal member, wherein at least an outer portion of said further support member comprises a plurality of displaceable members movable with respect to at least an inner portion of said further support member.

According to a further aspect, the movement of said displaceable members is predominantly in a front to back direction with respect to a users face when wearing said respiratory mask.

According to a further aspect, one or more of said displaceable members further includes one or more compliant members associated with a free end of said displaceable member.

According to a further aspect, said compliant member is a compressible hoop.

According to a further aspect, said compliant member is an articulated elastic beam.

According to a further aspect, said compliant member is a compressible foam material.

According to a further aspect, said support member or said further support member includes a semi-rigid reinforcing rib that substantially stiffens said support member or said further support member in a direction.

According to a further aspect, said reinforcing rib and said direction is substantially aligned with a mid sagittal plane of said user when wearing said mask.

In another aspect, the present invention may broadly be said to consist in an interface substantially as herein described with reference to any one or more of the drawings.

In another aspect, the present invention may broadly be said to consist in an interface comprising a mask, headgear, a connection between said mask and said headgear comprising an elastic extensile element and a substantially non-extensile element arranged in parallel, a adjustment mechanism operable to adjust the length of the non-extensile element of the connection.

According to a further aspect, said connection is adapted to in use extend from a first side of said mask, around the back of a user's head, to a second side of said mask.

According to a further aspect, the mask has left and right sides, and the headgear has left and right sides, said connection includes a first connection between the left side of the mask and the left side of the headgear, and a second connection between the right side of the mask and the right side of the headgear, the first and second connections comprising an elastic extensile element and a substantially non-extensile element arranged in parallel, a first adjustment mechanism operable to adjust the length of the non-extensile element of the first connection, and a second adjustment mechanism operable to adjust the length of the non-extensile element of the second connection.

According to a further aspect, said interface further comprises a third connection between the left side of the mask and the left side of the headgear, and a fourth connection between the right side of the mask and the right side of the headgear, the third and fourth connections comprising an elastic extensile element and a substantially non-extensile element arranged in parallel, a third adjustment mechanism operable to adjust the length of the non-extensile element of the third connection, and a fourth adjustment mechanism operable to adjust the length of the non-extensile element of the fourth connection.

According to a further aspect, the first and second connections connect between an upper portion of the mask and an upper portion of the headgear, and the third and fourth connections connect between a lower portion of the mask and a lower portion of the headgear.

According to a further aspect, the first and second adjustment mechanisms are operable to adjust the length of the non-extensile elements of the first and second connections.

According to a further aspect, the third and fourth adjustment mechanisms are operable to adjust the length of the non-extensile elements of the third and fourth connections.

According to a further aspect, all the adjustment mechanisms are located on the mask.

According to a further aspect, all the adjustment mechanisms are of a locking type having at least two modes, wherein in a first locking mode the length of said non-extensile element cannot be lengthened, and in a second un-locking mode the length of said non-extensile element can be lengthened.

According to a further aspect, the length of said non-extensile element can be shortened when said locking mechanism is in said locking mode.

According to a further aspect, the first and second connections pass around the side of a users head and are located above a users ear, and the third and fourth connections pass around the side of a users head and are located below a users ear.

According to a further aspect, the adjustment mechanisms are each one of:
a. a friction clasp
b. a ladder lock
c. a buckle
d. a ratchet
e. a clamp
f. a cam cleat According to a further aspect, the elastic element and non-extensile element of the first connection are attached to the mask at a substantially coinciding attachment location, and the elastic element and non-extensile element of the second connection are attached to the mask at a substantially coinciding attachment location.

According to a further aspect, the elastic element and non-extensile element of the third connection are attached to the mask at a substantially coinciding attachment location, and the elastic element and non-extensile element of the fourth connection are attached to the mask at a substantially coinciding attachment location.

According to a further aspect, the elastic element and non-extensile element of the first connection are attached to the headgear at a substantially coinciding attachment location, and the elastic element and non-extensile element of the second connection are attached to the headgear at a substantially coinciding attachment location.

According to a further aspect, the elastic element and non-extensile element of the third connection are attached to the headgear at a substantially coinciding attachment location, and the elastic element and non-extensile element of the fourth connection are attached to the headgear at a substantially coinciding attachment location.

According to a further aspect, the length of the elastic extensile elements of the connections can be stretched to between approximately 1.5 times and 3 times their un-stretched length.

According to a further aspect, the length of the elastic extensile elements of the connections can be stretched to approximately double their un-stretched length.

According to a further aspect, the length of the elastic extensile elements of the connections are not adjustable other than by stretching of the material.

According to a further aspect, the retention force provided by the elastic extensile elements of the connections is sufficient to retain the mask on a user's face during fitting.

According to a further aspect, the retention force provided by the elastic elements of the connections is sufficient to assist sealing of the mask during use.

According to a further aspect, the mask is one of:
g. a nasal mask,
h. an oral mask,
i. an oral nasal mask (full face)
j. nasal pillows
k. oral mask including nasal prongs
l. nasal cannula According to a further aspect, the elastic elements and non-extensile elements of each respective connection are integrated one within the other.

According to a further aspect, the elastic elements of each connection include a passage within running a substantial length thereof, and the respective non-extensile elements are located in said passage.

According to a further aspect, the non-extensile elements of each respective connection are also configured to resist compressive forces along their length.

In another aspect, the present invention may broadly be said to consist in an interface comprising a mask, headgear, a connection between the mask and the headgear having a first adjustable mode wherein the length of the connection can be adjusted and a second fixed mode wherein the length of the connection cannot be substantially increased.

According to a further aspect, said connection comprises a right side connection and a left side connection, and wherein the length of the right side connection and the left side connection can each be adjusted in the first mode, and the length of the right side connection and the left side connection cannot be substantially increased in the second fixed mode.

According to a further aspect, the adjustment of the length of the connection is via a locking mechanism having at least two modes, wherein in a first locking mode the length of the connection cannot be lengthened, and in a second un-locking mode the length of said connection can be lengthened.

According to a further aspect, the length of said connection can be shortened when said locking mechanism is in said locking mode.

According to a further aspect, each connection comprises an elastic extensile element configured to provide a retention force to hold the mask on a wearers face in said first locking mode.

According to a further aspect, each connection comprises an elastic extensile element configured to provide a retention force to hold the mask on a wearers face in said second un-locking mode.

According to a further aspect, the headgear is less extensible than the elastic elements of the connections.

According to a further aspect, the headgear is less extensible than the connections.

In another aspect, the present invention may broadly be said to consist in a headgear for use with a mask comprising a first strap configured to engage the back of a user's head and comprising a lower rear portion, a left side portion, a right side portion, and left and right side upper arch portions, the lower rear portion adapted to in use be located on a user's neck substantially below the external occipital protuberance, the left and right side portions each extending from a respective side of the lower rear portion superolaterally behind a patients ears and mastoid processes, the left and right side upper portions each comprising an arch extending over the respective ears and extending forward of a users ears to define left and right upper termination portion, a second strap extending from an apex region of the left side arch to an apex region of the right side arch, a third and fourth strap each extending from a respective side of the lower rear portion forwards and under a user ears, a fifth and sixth straps each extending forwards from a respective upper termination portion.

According to a further aspect, the fifth and sixth straps are connected to a respective side upper termination portion such that the general angular orientation of each of the fifth and sixth straps can move in a generally sagittal plane.

According to a further aspect, the generally sagittal planes correspond to the respective side surfaces of a patient's head.

According to a further aspect, the connections between the fifth and sixth straps and the respective side upper termination portion pivot about a generally laterally extending axis.

According to a further aspect, the second strap comprises a left hand side portion and a right hand side portion releasably joined together.

According to a further aspect, the second strap is adjustable in length.

According to a further aspect, the first and second straps are formed from a single flat member.

According to a further aspect, said flat member takes up a 3D headgear shape adapted to engage a user's head when the left and right hand side portions of the second strap are joined together.

According to a further aspect, the first, second, third and fourth straps are formed from a single flat member.

According to a further aspect, the third and fourth straps are not formed from said single flat member.

According to a further aspect, the fifth and sixth straps are not formed from said single flat member.

According to a further aspect, the second strap consists of a single material and the material is not soft.

According to a further aspect, the first and second straps are of a self supporting and resilient material.

According to a further aspect, the third and fourth straps are of a self supporting and resilient material.

According to a further aspect, the fifth and sixth straps are of a self supporting and resilient material.

According to a further aspect, the third and fourth straps are of a soft material.

According to a further aspect, the fifth and sixth straps are of a soft material.

According to a further aspect, the left and right side arch portions consist of a single resilient material.

According to a further aspect, the width of the second, third, fourth, fifth and sixth straps is between 10 mm and 30 mm.

According to a further aspect, the width of the first strap except at the lower rear portion is between 10 mm and 30 mm.

According to a further aspect, the width of the first strap at the lower rear portion is between 10 mm and 50 mm.

According to a further aspect, the thickness of the first, second, third, fourth, fifth and sixth straps is between 0.1 and 3 mm.

According to a further aspect, the straps are a laminate with a layer of one of the following materials:
m. Non-woven polypropylene (PP)
n. Non-woven polyethylene (PE)
o. Santoprene/polypropylene blend According to a further aspect, the third and fourth straps include a region of reduced strap width.

According to a further aspect, the reduced width regions are adjacent the lower rear portion.

According to a further aspect, the fifth and sixth straps include a region of reduced strap width.

According to a further aspect, the reduced width regions of the fifth and sixth straps are adjacent the upper termination portions.

According to a further aspect, any one or more of the following includes a laminate structure comprising at least one soft material in addition to the:
p. the first strap,
q. the third or fourth straps,
r. the fifth or sixth straps.

In another aspect, the present invention may broadly be said to consist in an interface comprising:
a mask defining a gases cavity and having left and right sides,
headgear including left and right side straps for connection between the left side of the headgear and the left side of the mask, and between the right side of the headgear and the right side of the mask respectively, wherein
the mask includes a first separable connection for attachment to the left side strap, and a second separable connection for attachment to the right side strap, and
there being no further separable connections not located on the exterior surface of the front of the mask.

According to a further aspect, the headgear includes further left and right side straps for connection between the left side of the headgear and the left side of the mask, and between the right side of the headgear and the right side of the mask respectively, wherein
the mask further includes a third separable connection for attachment to the further left side strap, and a fourth separable connection for attachment to the further right side strap.

According to a further aspect, each separable connection comprises a protrusion located on the exterior surface of the front of the mask, and
the left and right side straps each include at least one aperture sized to fit over a respective protrusion to complete the connection.

According to a further aspect, each protrusion extends away from the mask surface and includes a flange at the distal end of the protrusion operable to resist passing through the aperture.

In another aspect, the present invention may broadly be said to consist in a mask assembly comprising a gases cavity having an interior surface, a seal for contacting a wearer's face to substantially seal said cavity, a plenum space at least partially defined by a partition wall located within said gases space and in fluid communication with a gases entry port for receiving gases, a diffuser port outlet through which gases can flow from the plenum space to the gases cavity, and wherein the diffuser port outlet is at least partially defined by a perimeter portion of said wall.

According to a further aspect, said diffuser port extends substantially around the entire perimeter of the wall.

According to a further aspect, said diffuser port is less than 10 mm wide.

According to a further aspect, said diffuser port is between 3 and 6 mm wide.

According to a further aspect, the wall is configured to deflect gases flow from the entry port to enter he gases cavity around the peripheral edges of the wall proximate at least a portion of the seal.

According to a further aspect, said mask further comprises one or more pressure monitoring port.

According to a further aspect, the pressure monitoring port is located on the mask body and extends through the plenum chamber and is in fluid communication with the gases cavity.

According to a further aspect, the seal is an inflating seal.

According to a further aspect, the gases entry port has a short length of highly flexible tubing for connection to a breathing tube attached.

According to a further aspect, the total cross sectional area of the diffuser port is at least two times the area of the gases entry port.

According to a further aspect, the diffuser port extends substantially around the entire perimeter of the partition wall.

According to a further aspect, the diffuser port is not a continuous opening extending substantially around the entire perimeter of partition wall and includes regions along the partition wall periphery that are closed.

According to a further aspect, the partition wall includes one or more apertures therethrough.

According to a further aspect, the mask includes one or more flow directing rib extending approximately radially from a central region of the partition wall and projecting from the partition wall or the mask cavity wall.

In another aspect, the present invention may broadly be said to consist in a mask assembly comprising a gases cavity having an interior surface, a seal for contacting a wearer's face to substantially seal said cavity, a flow influencing structure configured to swirl breathing gases in a cyclonic pattern approximately tangential to a wearers facial surface, a gases entry port fluidly connected to the flow influencing structure.

According to a further aspect, the flow influencing structure comprises a substantially cylindrical wall extending substantially perpendicular to the mask cavity wall, a substantially conical wall extending coaxially with the cylindrical wall and defining an approximately annular swirling space between the cylindrical wall and the conical wall.

According to a further aspect, the annular swirling space is open to the cavity, and narrower near the mask cavity wall.

According to a further aspect, the gases entry port is offset from the centre of the annular swirling space and configured to direct gases flow into the annular swirling space approximately tangentially.

According to a further aspect, a mask assembly as described above further comprising an anti-asphyxiation valve.

According to a further aspect, a mask assembly as described above further comprising one or more pressure monitoring port.

In an aspect of the invention, a respiratory interface comprises an inflating soft compliant seal member adapted to cover a nose and a mouth of a user. The seal member comprises a sealing portion that is adapted to contact a face of the user. The sealing portion comprises a rolled perimetric edge and a sealing flange that extends inwardly from the perimetric edge. The sealing flange comprises an extended surface that has one end connected to the rolled perimetric edge. A support member is secured to the seal member. The support member is more rigid than the seal member. The support member comprises a support member perimetric edge. The rolled perimetric edge of the sealing portion extends outward beyond the support member perimetric edge. A generally vertical medial plane divides the interface into a right half and a left half. The interface is more flexible about the generally vertical medial plane than about any generally horizontal plane that extends through the interface.

According to a further aspect, the rolled perimetric edge of the sealing portion extends beyond the support member perimetric edge around an entire length of the support member perimetric edge.

According to a further aspect, the sealing flange extends radially inwardly from substantially all of the rolled perimetric edge of the seal member.

According to a further aspect, the seal member further comprises an enclosing portion that connects to the sealing portion proximate the rolled perimetric edge of the sealing member, the enclosing portion being secured to the support member.

According to a further aspect, the sealing portion of the seal member is substantially more flexible than the enclosing portion of the seal member.

According to a further aspect, the rolled perimetric edge of the seal member in plan view is defined by a plurality of radii R1 and the rolled perimetric edge in section comprises a thickness t and an inside radius R2, a generally horizontal plane extends through a first upper connection for headgear and a second upper connection for headgear and an upper portion of the rolled perimetric edge of the seal member is defined above the generally horizontal plane, and wherein the entire upper portion of the perimetric edge satisfies (1) $4 \leq (R2/t) \leq 7$ and (2) $(R1/R2) < 10$.

According to a further aspect, a point of first contact is positioned along at least a portion of the sealing flange such that the sealing flange is adapted to contact the face of the user before the rolled perimetric edge.

According to a further aspect, the support member comprises a plurality of individually displaceable members that are positioned between an attachment for a headgear assembly and the seal member such that the displaceable members can transfer forces from the headgear assembly to the seal member.

In an aspect of the invention, a respiratory interface comprises an inflating soft compliant seal member adapted to cover a nose and a mouth of a user. The seal member comprises a sealing portion that is adapted to contact a face of the user. The sealing portion comprises a rolled perimetric edge and a sealing flange that extends inwardly from the perimetric edge. The sealing flange comprises an extended surface that has one end connected to the rolled perimetric edge. A support member is secured to the seal member. The support member is more rigid than the seal member. The interface defines a chamber. An airflow inlet extends into the chamber and a flow diverter is positioned within the chamber proximate the airflow inlet. The flow diverter causing at least a portion of an airflow from the airflow inlet to be diffused radially within the interface.

According to a further aspect, the diffused airflow is directed radially over at least a portion of the sealing flange.

According to a further aspect, the airflow inlet extends into the interface at an angle between about 0° and about 70° from vertical.

According to a further aspect, the flow diverter comprises a partition wall.

According to a further aspect, the flow diverter comprises a swirling structure.

According to a further aspect, the interface is in combination with a headgear assembly that is connected to the support member of the interface.

In an aspect of the invention, a headgear assembly is used to secure a respiratory interface to a head. The headgear assembly comprises a first strap portion. The first strap portion comprises a lower rear region. The lower rear region is adapted to be located on or below an external occipital protuberance. The lower rear region extends forward and upward to a first side region and a second side region. The first side region extends superolaterally from the lower rear region. The second side region extends superolaterally from the lower rear region. Each of the first and second side regions is adapted to extend rearward of a mastoid process and over an ear. The first side region comprises a first arched portion and the second side region comprises a second arched portion. The first arched portion and the second arched portion are connected by a top strap. The top strap is adapted to extend over the head from above the ears. A first termination portion extends forward from the first arched portion and a second termination portion extends forward from the second arched portion.

According to a further aspect, the top strap is adapted to be positioned forward of a crown of the head and the lower rear region is adapted to be positioned below the crown of the head such that the crown of the head is captured between the top strap and the lower rear region.

According to a further aspect, at least a portion of the first strap portion is semi-rigid.

According to a further aspect, the top strap comprises a first portion and a second portion, the first portion and the second portion being attached to each other with a connector.

According to a further aspect, the headgear assembly includes a first inelastic connecting strap and a second inelastic connecting strap, the first inelastic connecting strap and the second inelastic connecting strap being securable to an interface.

According to a further aspect, the headgear assembly includes a first elastic connecting strap and a second elastic connecting strap, the first elastic connecting strap and the second elastic connecting strap being securable to the interface.

According to a further aspect, the first inelastic connecting strap and the first elastic connecting strap extend in parallel between the first termination portion and the interface and the second inelastic connecting strap and the second elastic connecting strap extend in parallel between the second termination portion and the interface.

According to a further aspect, the headgear assembly comprising a third inelastic connecting strap and a fourth inelastic connecting strap, the third inelastic connecting strap and the fourth inelastic connecting strap extending between the first strap portion and the interface.

According to a further aspect, the headgear assembly including a first lower connecting strap and a second lower connecting strap extending away from the first strap portion, at least a portion of the first and second lower connecting straps being semi-rigid whereby the first and second lower connecting straps are adapted to present laterally outward or forward when the lower rear region is positioned on the head such that the first lower connection strap and the second lower connecting strap are less likely to tangled behind the head when the headgear assembly is positioned on the head.

According to a further aspect, the first lower connecting strap and the second lower connecting strap are connected to the lower rear region and the semi-rigid portion is proximate a connection between the first lower connecting strap, the second lower connecting strap and the lower rear region.

According to a further aspect, the headgear assembly is in combination with an interface, the interface comprising a support member and a seal member, the seal member being connected to the support member, the headgear assembly being connected to the support member.

According to a further aspect, an adjustment line is provided with an upper sliding connection between the adjustment line and an upper portion of the interface. A lower sliding connection is between the adjustment line and a lower portion of the interface. A left sliding connection is between the adjustment line and a left side portion of the headgear assembly. A right sliding connection is between the adjustment line and a right side portion of the headgear assembly. The adjustment line connects the upper sliding connection, the left sliding connection, and the right sliding connection and the lower sliding connection.

According to a further aspect, an adjustment mechanism is attached to the adjustment line such that a length of the adjustment line can be altered whereby a tension in an assembly of the headgear assembly and the interface can be altered.

According to a further aspect, the adjustment mechanism alters the length of the adjustment line to provide a predetermined level of tension between the interface and the headgear assembly.

According to a further aspect, the interface is connected to the headgear assembly with a tensioning component, the tensioning component cooperating with a locking element such that the tensioning component provides an elastic connection between the interface and the headgear assembly during fitting of the headgear assembly and interface while the locking element creates an inelastic connection between the interface and the headgear assembly following fitting of the headgear assembly and interface.

According to a further aspect, the tensioning component comprises a line with an adjustable length and the locking element comprises a clasp.

According to a further aspect, the support member of the interface comprises attachments for the headgear assembly.

According to a further aspect, the headgear assembly connects to the interface at a first connection point, the headgear assembly being configured such that adjusting a tension of the headgear assembly takes place at or forward of the first connection point.

According to a further aspect, fastening of the headgear assembly to the interface does not comprise a strap that creates tension by being bent back toward the headgear assembly from the first connection point.

According to a further aspect, the first connection point comprises a post and the headgear assembly comprises at least one corresponding aperture that engages with the post.

In an aspect of the invention, a method of securing an interface and headgear assembly to a head, wherein the headgear assembly is moveably and elastically connected to an upper portion of the interface, comprises placing the interface on a face using a first hand, gripping a rear portion of the headgear assembly with a second hand and raising the rear portion of the headgear assembly over the head, pulling the rear portion of the headgear assembly down over a back of the head until a top strap of the headgear assembly is seated on a top of the head, releasing the headgear assembly from the second hand and releasing the interface from the first hand such that the elastically connected headgear assembly and interface substantially remain in position without being held by the first hand or the second hand, securing an inelastic lower strap to the interface and securing an inelastic upper strap to the interface such that the interface and headgear assembly are inelastically connected.

According to a further aspect, an elastic component extends between the headgear assembly and the interface assembly to provide the elastic connection between the headgear assembly and the interface, the method further comprising orienting the interface with the elastic component between the upper portion of the interface and the headgear assembly such that the headgear assembly and the interface can be correctly oriented relative to the face.

According to a further aspect, the interface comprises a seal with an inwardly extended flange, the flange comprises a recess that is adapted to receive a chin, the method further comprising position the chin within the recess while placing the interface on the face using the first hand.

According to a further aspect, the chin is positioned within the recess prior to the interface being brought into contact with a nose.

BRIEF DESCRIPTION OF THE DRAWINGS

These and other features, aspects and advantages of the present invention will now be described with reference to the drawings of several preferred embodiments, which embodiments are intended to illustrate and not to limit the invention, and in which figures.

DETAILED DESCRIPTION OF PREFERRED EMBODIMENTS

Overall System

Figure 1:
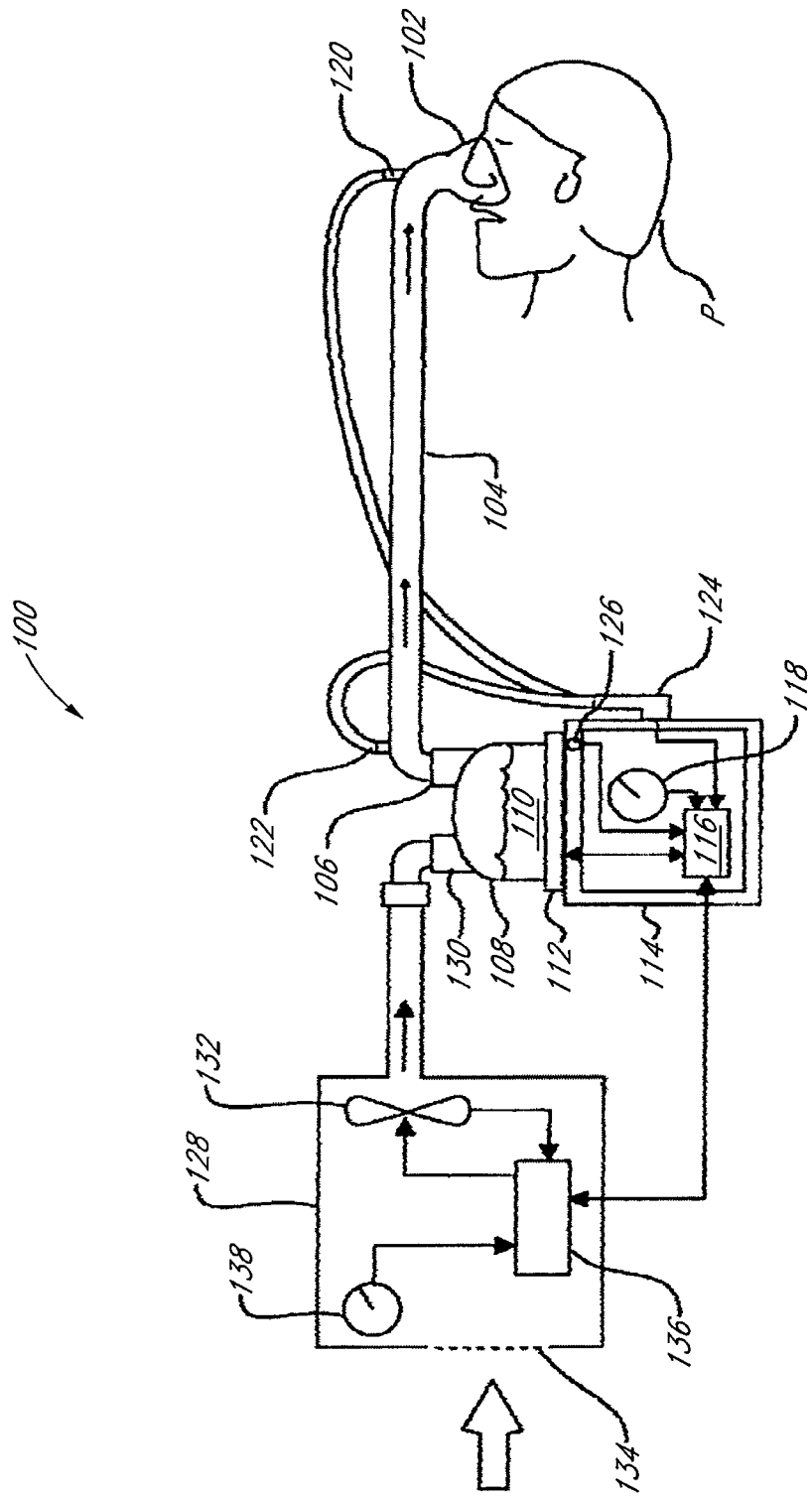
FIG. 1 is a block diagram of a humidified positive airway pressure system as might be used in conjunction with the patient interface and/or headgear that is arranged and configured in accordance with certain features, aspects and advantages of the present invention.

With reference to FIG. 1, a humidified positive airway pressure (PAP) system 100 is shown in which a patient P, or other user, is receiving humidified and pressurized gases through a patient interface 102. The PAP system 100 can be continuous, variable or bi-level positive airway pressure or any other suitable form of respiratory therapy. In some configurations, the PAP system 100 could be or include a hospital ventilator or any other suitable form of respiratory therapy. In some applications, the interface 102 can be used with non-humidified PAP systems.

The interface 102 connects to a conduit that defines a humidified gases transportation pathway or inspiratory breathing tube 104, for example. The conduit 104 may contain heating means or a heater wire (not shown) that heats the gases or the walls of the conduit to reduce condensation of humidified gases within the conduit.

The conduit 104 connects to an outlet 106 of a humidification chamber 108. The humidification chamber 108 preferably contains a volume of water 110. The humidification chamber 108 preferably is formed from a plastics material. In some configurations, the humidification chamber has a highly heat conductive base (e.g., an aluminum base or the like) that is in direct contact with a heater plate 112 of a humidifier 114.

The humidifier 114 includes a suitable controller 116. The controller 116 can be any suitable controller or control means and can be an electronic controller. The controller 116 may comprise a microprocessor-based controller that executes computer software commands stored in associated memory.

The controller 116 receives input from sources such as, for example but without limitation, a user input 118 (e.g., dial, button and the like) through which a user of the system 100 can set, for example but without limitation, a value (e.g., a preset value, an entered value or the like) that represents a desired level of humidity and/or temperature of the gases supplied to patient P. The controller may also receive input from other sources (e.g., temperature and/or flow velocity sensors 120, 122 through a connector 124, and a heater plate temperature sensor 126).

In response to a user-set humidity and/or temperature value, which can be input with the user input 118, and the other inputs, the controller 116 determines when or to what level to energize the heater plate 112 to heat the volume of water 110 within the humidification chamber 108. As the volume of water 110 within the humidification chamber 108 is heated, water vapor begins to accumulate in the volume of the humidification chamber 108 above the surface of the water volume 110.

The water vapor passes out of the outlet 106 of the humidification chamber 108 with a flow of gases (e.g., air) provided from a gases supply blower 128 or other suitable gases supply means, which flow of gases enters the humidification chamber 108 through an inlet 130. Exhaled gases from the patient's mouth are passed directly to ambient surroundings in FIG. 1 or, when the therapy is being delivered by a ventilator, the exhaled gases are returned to the ventilator via an expiratory breathing tube (not shown).

The blower 128 includes a variable pressure regulator, a variable pressure regulating means or a variable speed fan 132 that draws air or other gases through a blower inlet 134. The speed of the variable speed fan 132 is controlled by a controller 136 in response to inputs for the controller 136 and a user-set, predetermined or preset value of pressure or fan speed with a user input 138 (e.g., a dial, button or the like). In some configurations, the functions of the controller 136 could be performed by the controller 116.

Figure 35:
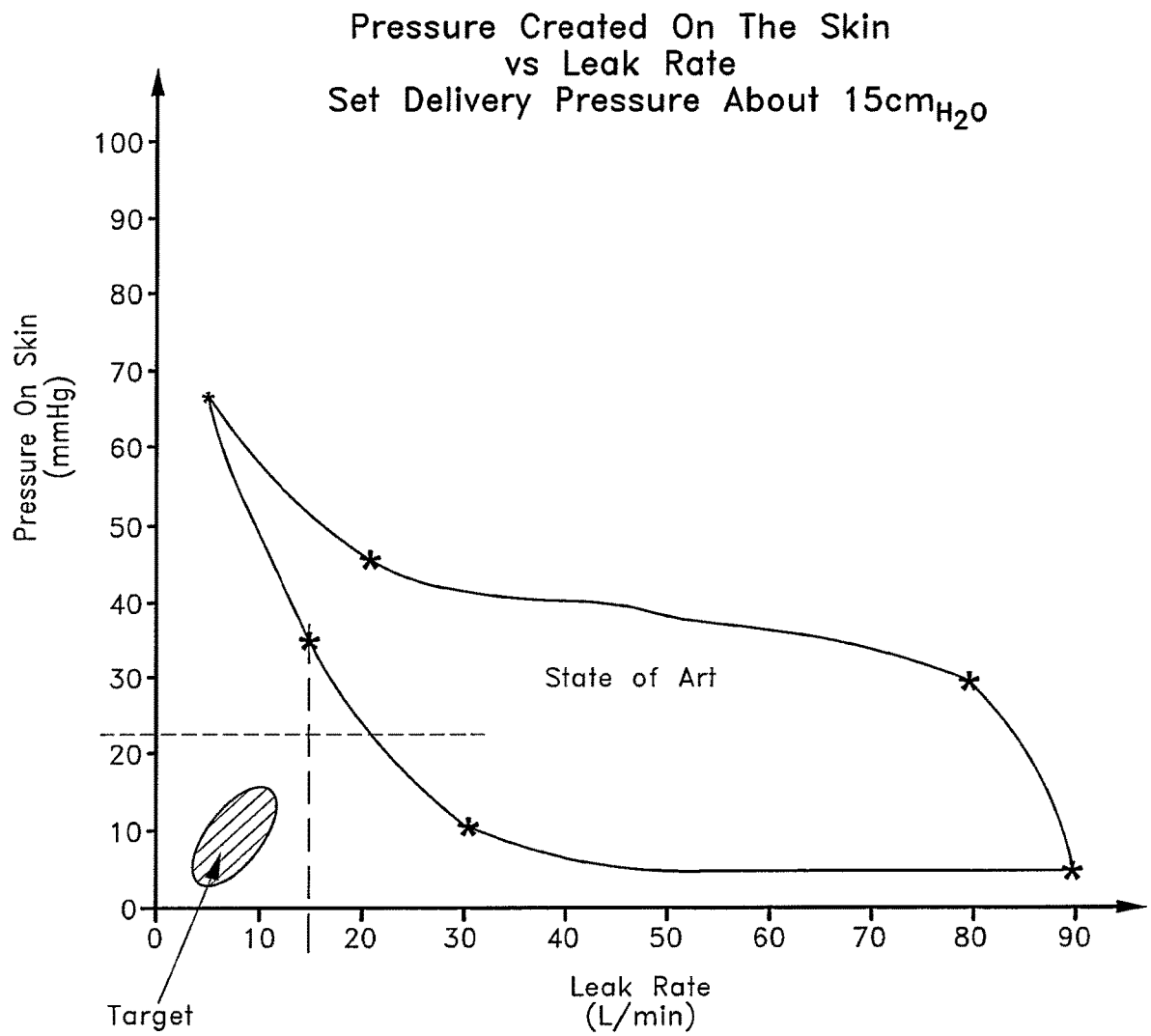
FIG. 35 is a graphical depiction of a relationship between pressure on skin exerted by an interface and headgear assembly and leak rate from the interface.

The patient interface 102 generally comprises a mask and associated headgear. The patient interfaces described below find particular utility in hospital or other urgent care settings where patients often require artificial respiratory therapy without delay. In addition, patients in such settings often receive artificial respiratory therapy for prolonged and often uninterrupted periods of time. Accordingly, the interfaces are designed to be rapidly fitted to patients and the interfaces are designed to provide increased comfort. Preferably, the interfaces and headgear assemblies are capable of being initially fitted in less than about 25 seconds while achieving a leak rate of less than about 20 L/min with a set delivery pressure through the interface of about 15 cm $H_2O$. In addition, as shown in FIG. 35, the interfaces and headgear assemblies preferably achieve a leak rate that is less than about 15 L/min and a skin surface pressure that is less than about 22.5 mmHg with a set delivery pressure through the interface of about 15 cm $H_2O$. The skin surface pressure of 22.5 mmHg has been found to be clinically significant in reducing the likelihood of developing pressure sores over prolonged treatment periods. Leakage rates of about 15 L/min have been found to be relevant to stability of equipment used to provide the pressurized gases. In some configurations, the skin surface pressure can be less than about 18 mmHg with a leak rate of less than about 11 L/min.

Figure 36:
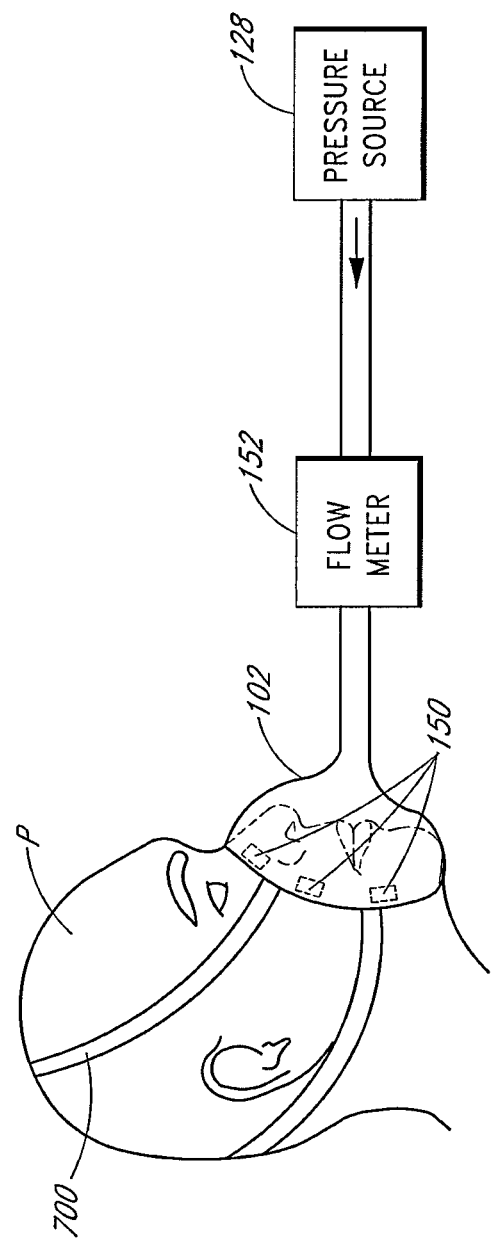
FIG. 36 is a schematic view of a testing configuration for determining a relationship between pressure and leak rate.

With reference to FIG. 36, a method of determining skin surface pressure and leak rates will be described. As shown in FIG. 36, one or more sensors 150 can be positioned on the face of the test subject P. The sensor or sensors 150 can be positioned along a contact region for the interface 102. Preferably, the sensor or sensors 150 are positioned along regions that are prone to developing pressure sores during treatment (e.g., the region extending from the cheek bones, under the eyes and across the nasal bridge). The sensors 150 are adapted to sense pressure. In some configurations, the sensors 150 are pressure transducers. Preferably, the sensors 150 are pressure transducers that have an operating range between about 0 mmHg and about 100 mmHg. More preferably, the sensors 150 are pressure transducers that have an operating range between about 0 mmHg and about 50 mmHg. The sensors 150 also preferably are thin film pressure transducers. In some configurations, the sensors 150 have a thickness of about 0.5 mm or less.

With the sensors 150 positioned on the face of the test subject, the interface 102 can be applied to the face of the test subject such that the interface rests on the sensors 150. The pressure source 128 can be turned on such that pressurized gases are supplied to the test subject through the interface 102. Preferably, the gases are pressurized to about 15 cm $H_2O$ for purposes of the analysis. The interface 102 can be secured in place with tension provided by a headgear assembly 700. Preferably, the headgear assembly 700 is used to provide sufficient tension to reduce to about zero the leakage between the interface and the face of the test subject in the eye region. For purposes of the test, no bias flow holes are provided (i.e., any bias flow holes in the system are occluded) in the system such that any leakage generally occurs only between the interface and the test subject.

With the interface tensioned to the face of the test subject and with the pressure source providing gases at a pressure of about 15 cm $H_2O$, the test subject then holds their breath such that the pressurized gases leak from the seal between the interface 102 and the face of the test subject P. The leakage rate can be determined using a flow meter 152. The flow meter 152 can be integrated with the ventilator or other source of positive pressure gases or the flow meter 152 can be a separate component. Preferably, the flow meter 152 is operable in the range of about 0 L/min and about 200 L/min.

While the pressurized gases leak, the leakage rate and the pressure between the interface and the face of the test subject can be monitored. After the peak leakage rate and the peak pressure have been recorded, the tension provided by the headgear assembly 700 can be adjusted (e.g., increase) and additional sets of data can be obtained. With multiple data points, a performance envelope can be derived for the interface that reflects skin pressure and leakage rates. Multiple test subjects can be used to provide multiple readings.

Exposed Nose Mask

Figure 2:
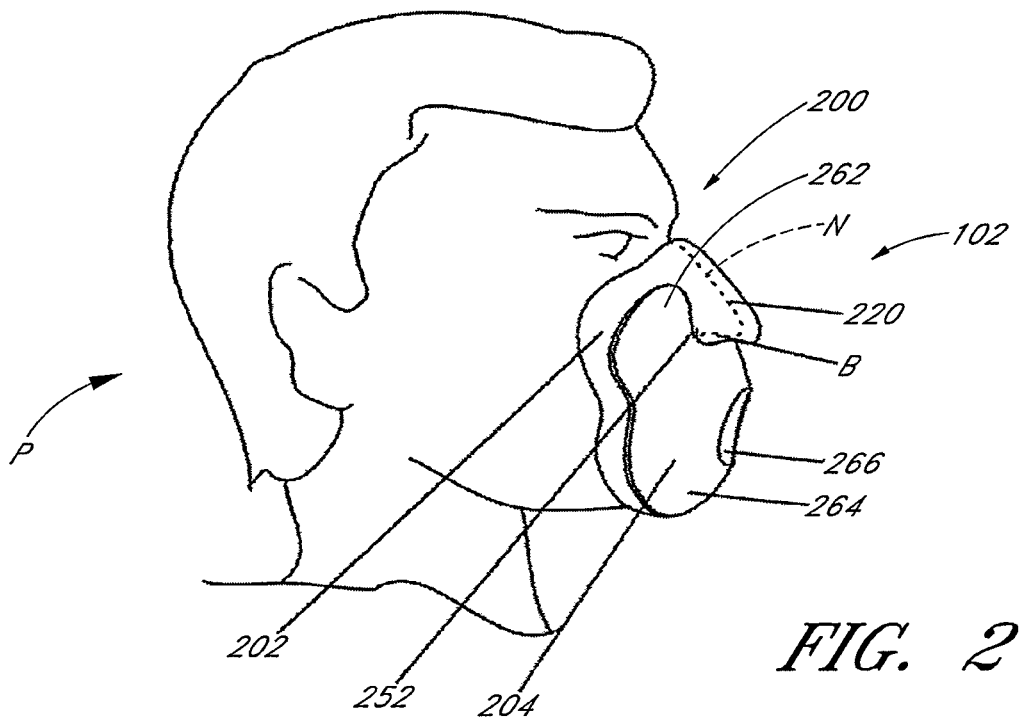
FIG. 2 is a side view of an interface body that is arranged and configured in accordance with certain features, aspects and advantages of the present invention. The illustrated body is shown fitted on a user but without headgear or a breathing tube attached.

With reference now to FIG. 2, the illustrated interface 102 comprises an interface body 200 that generally comprises a compliant seal member 202 and a supporting member 204. In FIG. 2, the interface 102 is shown on a patient P without any attached headgear or breathing tube connections. As will be described, at least a portion of an outer appearance of the interface 102 preferably carries an appearance of a substantial reproduction of at least one human facial feature. In some configurations, at least a portion of the outer appearance of the interface 102 comprises a substantial reproduction of at least a human nose.

As shown in FIG. 2, the illustrated interface 102 is a full face mask that covers both a nose N and a mouth of the patient P, or other user. The interface 102 can be sized according to the application. In other words, the interface 102 can be provided in a variety of sizes to accommodate use by patients or other users that can vary in age upward from as young as about two years old. The interfaces 102 can be sized based upon a measurement from chin to nasal bridge on a patient. Preferably, the size ranges that can be accommodated by each consecutive interface size will overlap between about 3 mm to about 7 mm. More preferably, the sizes will overlap about 5 mm. For example, three interface sizes can be provided based upon a chin to nasal bridge measurement criteria: small or size 1 for those with measurements up to about 110 mm; medium or size 2 for those with measurements from about 105 mm to about 130 mm; and large or size 3 for those with measurements from about 125 mm to about 145 mm. Advantageously, the measurement ranges overlap from one size to the next such that two sizes can be used on a single patient within the overlap, which ensures that patients will not fall into a gap between sizes. Other measurement techniques also can be used.

An external surface of the interface 102 preferably is of a shape familiar to the hand, which improves operation by the person placing the interface 102 on the patient. Preferably, the shape of the illustrated interface 102 encourages grasping of the interface 102 during fitting by the healthcare provider in the chin region of the interface 102. Such a grasping location results in the hand of the healthcare provider not approaching the eye region of the patient during fitting of the interface 102, which can be more calming on the patient during fitting. In addition, the protruding reproduction of the nose clearly indicates correct placement on the patient and provides a significant visual and tactile cue for correct location, making the mask very easy and intuitive to fit and to use.

Preferably, the interface 102 has a low profile that generally conforms to the contour of the face. This minimizes patient awareness of the mask and minimizes the compressible internal volume, which makes the interface 102 particularly suitable for use on ventilation. The low profile interface 102 preferably is out of the patient's line of sight and only minimally impacts on the patient's peripheral vision. In addition, relative to the prior art, the low profile interface 102 decreases the compressible volume defined within the interface while also decreasing the volume of rebreathable $CO_2$, each of results in a more desirable interface construction and enhanced interface performance.

Compliant Seal Member

Figure 5:
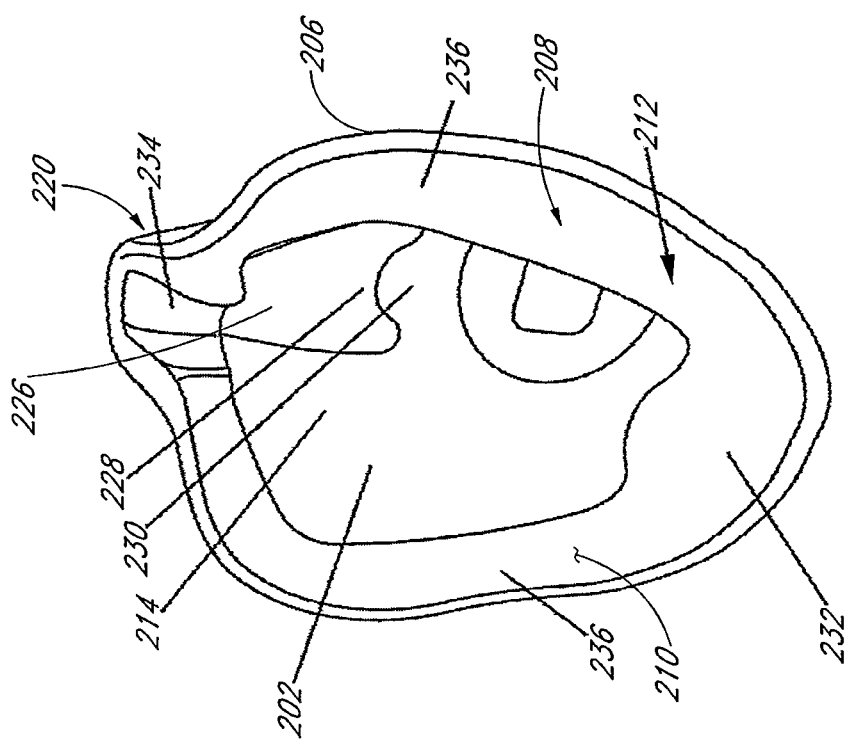
FIG. 5 is a rear perspective view of an inside of the seal member of the interface of body of FIG. 2.
Figure 4:
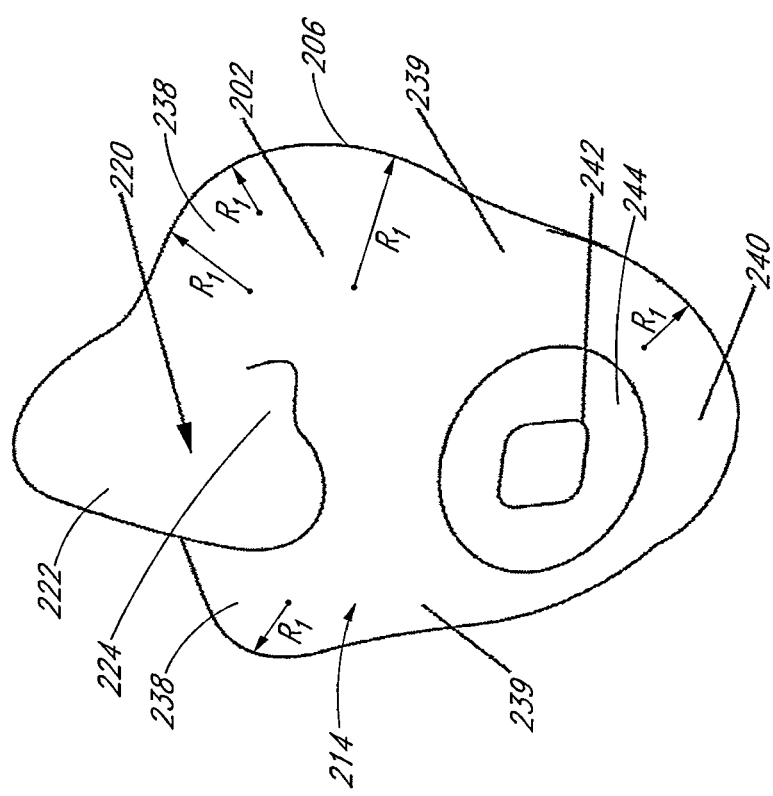
FIG. 4 is a front perspective view of an outside of a seal member of the interface body of FIG. 2.

With reference now to FIGS. 2, 4 and 5, the compliant seal member 202 is the component of the interface 200 that contacts the face of the patient P. The seal member 202 preferably is an inflating or ballooning seal type. An inflating or ballooning seal type is a type of seal that, when in use, system pressure or air flow delivered to the interface 102 acts to urge an inwardly extending flange, skirt or other similar member onto a patient's face to form a substantial seal. Thus, an inflating or ballooning seal type is different from seal types that rely solely upon interface retention forces from headgear to push or deform a cushion against the patient's face with enough force to seal the cushion against the patient's facial features.

To provide a suitable inflating or ballooning effect, the illustrated seal member 202 comprises a perimetric edge 206 and a sealing flange 208 that extends inwardly from the perimetric edge 206. Preferably, the sealing flange 208 extends inwardly from all or substantially all of the perimetric edge 206. As will be described, the perimetric edge 206 preferably comprises a rolled edge.

Figure 6:
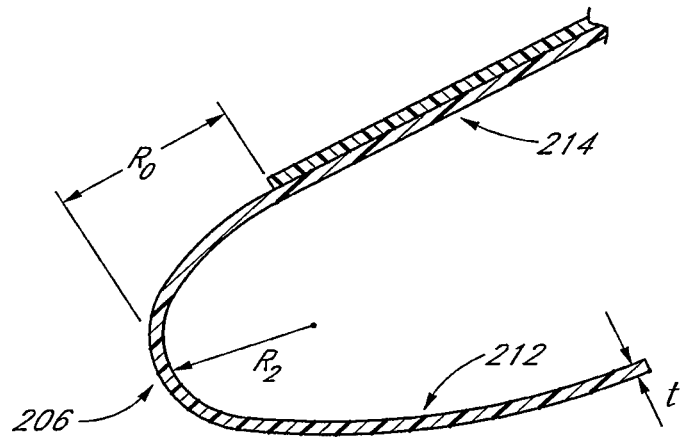
FIG. 6 is a schematic section view of a portion of the seal member showing a rolling and inflating aspect of the seal member.

With reference to FIG. 5, the illustrated sealing flange 208 comprises an extended surface 210, at least a portion of which will abut a skin surface of a face of a patient P. The extended surface 210, which has one end portion that is connected to the perimetric edge 206, defines a pocket-like structure that captures air or pressure from the air supply and that urges the flange 208 of the interface body 200 toward the face of the patient P to a desired degree. The sealing flange 208 can define at least a part of a sealing portion 212 of the illustrated seal member 202. The sealing portion 212 faces the patient, or is closest to the patient, in use. With reference to FIG. 6, the sealing portion 212 of the illustrated seal member 202 can be connected to an enclosing portion 214 of the seal member 202 at the perimetric edge 206, which can be defined by the rolled edge or by a radiused edge.

Preferably, the sealing portion 212 is substantially more flexible than the enclosing portion 214. The sealing portion 212 can be formed, for example but without limitation, of the same material as the enclosing portion 214 but the sealing portion 212 can have a lower thickness than the enclosing portion 214. In some embodiments, a different material, such as a silicone, a thermoplastic elastomer or a foam (e.g., open or closed including a skin) may be used for the sealing portion 212 relative to the enclosing portion 214. In use, the sealing portion 212 rests against the face of the patient P and, under an internal pressure of the inflating seal and a retention pressure of headgear, the sealing portion 212 is pressed against the face of the patient P to create an effective seal inward of the perimetric edge 206.

Figure 7:
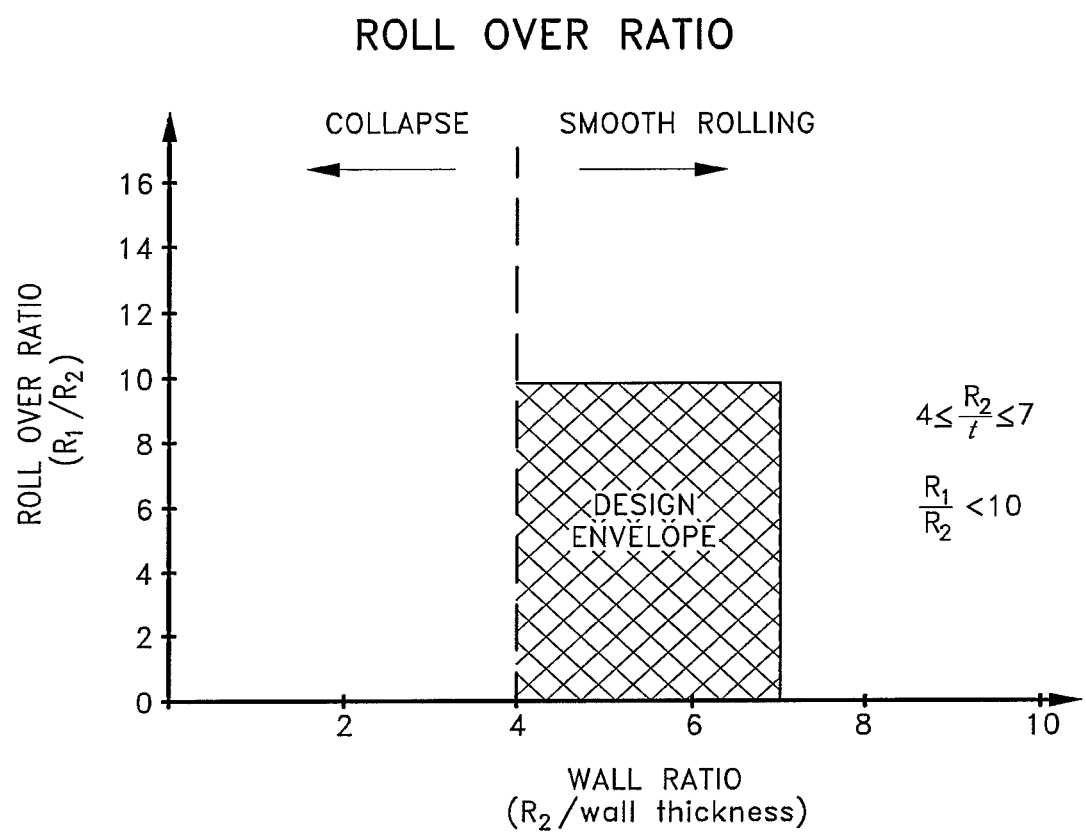
FIG. 7 is a graphical depiction of properties relating to rolling of the seal member.

With reference to FIG. 4, the perimetric edge 206 comprises a shape that can be defined by a series of radii $R_1$. The radii $R_1$ can be defined to the outer surface of the rolled perimetric edge 206. Thus, the outermost portion of the rolled perimetric edge 206 has a plan view shape that is defined by the series of radii $R_1$. In addition, as shown in FIG. 6, the rolled over perimetric edge 206 can be defined by a thickness (t) and an inside radius ($R_2$). FIG. 7 illustrates a desired relationship between the ratio of the inside radius of the rolling portion of the perimetric edge 206 at a particular segment to a wall thickness of the perimetric edge at that particular segment ($R_1/t$), hereinafter wall ratio, and the ratio of the particular radius $R_1$ of a particular segment of the perimetric edge 206 to the inside radius of the rolling portion of the perimetric edge 206 at that particular segment of the perimetric edge ($R_1/R_2$), hereinafter roller over ratio. As illustrated, it has been found that at a wall ratio of about 4 or less, the perimetric edge 206 of the seal member 202 may be subject to collapsing in that particular segment rather than exhibit a desired rolling. In addition, it has been found that a wall ratio of about 7 or more results in a configuration that may be too stiff in that particular segment to allow a desired rolling. Moreover, it has been found that at a radius ratio of about 10 or more, the particular segment of the seal member 202 may be too straight to allow a desired rolling. Thus, the region illustrated in FIG. 7 with hatching is a region of desired rollability for the perimetric edge 206. The perimetric edge 206, because it is defined by a series of radii in plan view, may have various segments that are positioned within the region of desired rollability. Preferably, at least the upper portion of the perimetric edge 206 (i.e., the portion that would leak in the general direction of the eyes when in use) is configured such that the dimensions completely fall within the region of desired rollability. In other words, preferably those segments satisfy the following two equations: (1) $4 \leq (R_2/t) \leq 7$ and (2) $(R_1/R_2) < 10$. In some configurations, at least the nasal portion of the seal member 202 and the laterally extending portions of the seal member 202 that extend toward the cheekbones are configured such that the dimensions (i.e., roll radius, plan radius and wall thickness) result in at least those segments falling within the region of desired rollability and satisfy the above-identified equations. In some configurations, at least the portion of the seal member 202 that is located above a generally horizontal plane that intersects upper headgear attachment location is configured such that the dimensions (i.e., roll radius, plan radius and wall thickness) result in at least those segments falling within the region of desired rollability and satisfy the above-identified equations. In some configurations, the entire perimeter of the seal member 202 is configured such that the dimensions (i.e., roll radius, plan radius and wall thickness) result in every segmented falling within the region of desired rollability and satisfy the above-identified equations.

Figure 8:
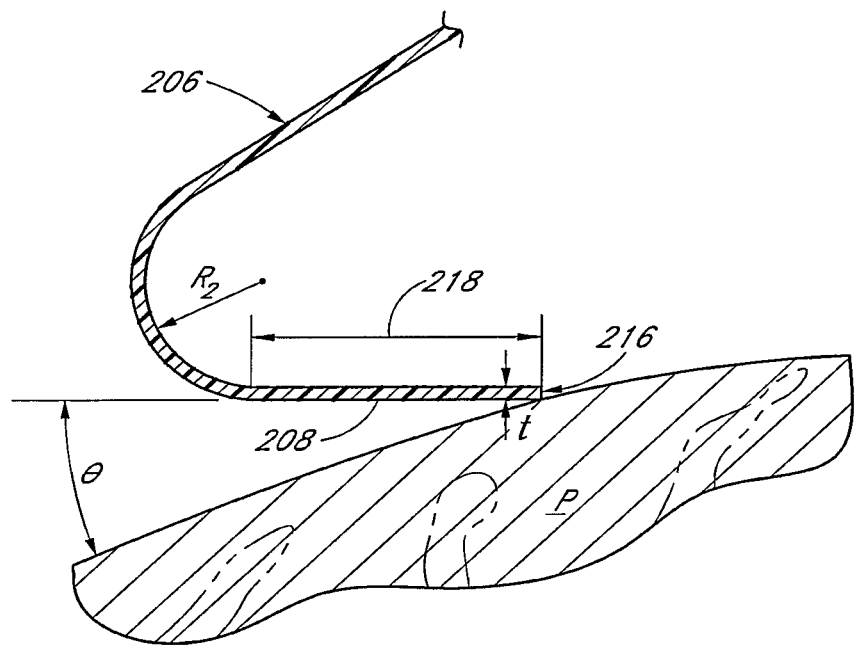
FIG. 8 is a schematic section view of a portion of the seal member showing an additional rolling and inflating aspect of the seal member.
Figure 9:
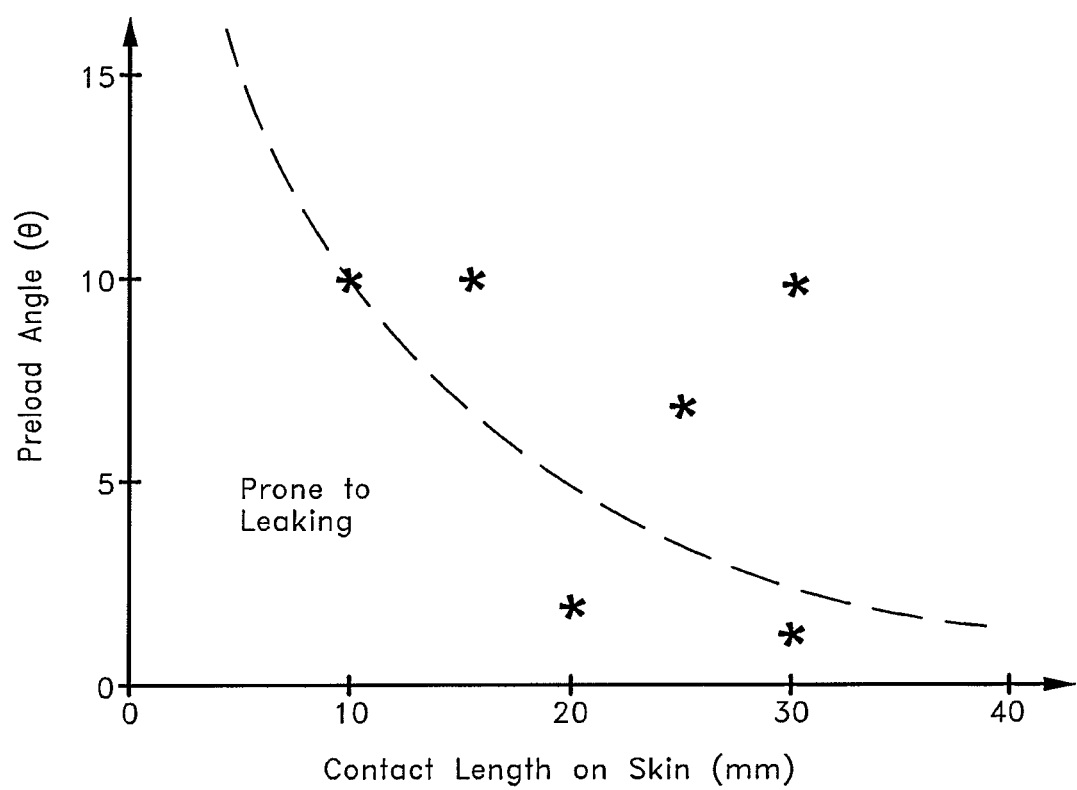
FIG. 9 is a graphical depiction of properties relating to preloading of the seal member.

Preferably, the sealing portion 212 curves inwardly to such an extent that the seal portion 212 forms an acute angle relative to the enclosing portion 214. Moreover, with reference to FIG. 8, the flange 208 is shown contacting a skin surface of the patient P. As shown, relative to a point of first contact 216, which is the end of the flange 208 disposed furthest from the perimetric edge 206 in the illustrated arrangement, the start of the radius $R_2$ can be located at a distance 218 between about 0 mm and about 40 mm or more. As shown in the graph of FIG. 9, a relationship is believed to exist between (1) the distance 218 (i.e., the distance between the point of first contact 216 and the start of the radius $R_2$) and (2) a preload angle $\Theta$, which is an angle between the flange 208 and the surface of the skin regardless of the location around the perimetric edge 206. The preload angle can be as shown graphically in FIG. 9, which graph was generated empirically. According to this relationship, the flange 208 is able to smoothly roll and compress against the face of the patient P. As shown in FIG. 9, increasing the contact length on the skin of the patient P can allow the contact angle to be lower, which indicates that a degree of protrusion of the free end of the flange can be decreased with a significant contact length. On the other hand, a greater protrusion of the free end of the flange can provide adequate sealing over a shorter contact length. In some configurations, the choice of the length 218 can be based upon the variation of a patient's facial geometry. In other words and by way of example only, to achieve a single size mask for varied populations, the flange is longer in the chin region where the dimensions of the face vary the most and the flange is shorter in the nasal region where the geometry varies less in dimension for a given ethnic group. The nasal bridge dimensions may vary from ethnic group to ethnic group. With the desired lengths determined, the angle can be determined to reduce the likelihood of leakage.

As described directly above, the point of first contact 216 results because the end of the flange 208 protrudes outward in at least some locations. In some embodiments, the free end of the flange 208 is the first surface of the interface body 200 to contact the face of the patient P. The distance 218 of the flange 208 preferably extends toward the face of the patient by between about 0 mm and about 10 mm. In some embodiments, the protrusion is between about 3 mm and 7 mm.

Advantageously, because the flange 208 presents toward the face of the patient, the free end of the flange 208, or another portion of the flange 208, after touching the face of the patient, curves inward (i.e., is bent inward) from a normal position a progressively increasing amount as the mask is urged into tighter contact with the face of the patient. Thus, the flange is preloaded while being donned, which provides the seal with an enhanced ability to conform around various facial anatomies and contours, which in turn provides improved sealing performance for the interface body 200.

Because the illustrated seal member 202 is an inflating or ballooning seal type, the seal member 202 acts to minimize the pressure on the skin. In addition, the seal member 202 acts to distribute pressure and reduce the likelihood of excessive localized pressure distributions. In other words, the illustrated seal member 202 reduces the likelihood of point-loading or excessive pressure gradients.

With reference again to FIG. 2, the seal member 202 is shown enveloping the nose N and mouth of the patient P. The seal member 202, as shown in FIGS. 4 and 5, comprises a nasal portion 220 that is shaped to be a substantial reproduction of the human nose. Preferably, the nasal portion 220 is an upper portion of the seal member 202. In the illustrated configuration, at least an outside surface of the nasal portion 220 is shaped to include a substantial reproduction of a human nose. Preferably, the outside surface and the inside surface of the nasal portion 220 are shaped to include a substantial reproduction of a human nose. In particular, in the illustrated configuration, the nasal portion 220 reproduces a substantial portion of a nose shape. Thus, the nasal portion 220 reproduces a majority of a nose shape.

In some embodiments, the nasal portion 220 of the seal member 202 reproduces the whole nose or very nearly the whole nose. The nose shape in the illustrated embodiment will be a generalized nose shape rather than matched to the particular patient. The illustrated nasal portion 220 comprises a nasal bridge 222. The illustrated nasal portion also may comprise nostril flares 224 or other similar features. Preferably, the nasal portion 220 simulates sufficient features to be representative of a human nose and to bear semblance to a human nose. In some embodiments, however, the seal member 202 may include a portion shaped to form a pocket or nasal chamber 226 that is capable of receiving a human nose but that does not constitute a substantial reproduction of the appearance of the nose. In other words, the seal member 202 can have a nasal portion with a shape that approximates a shape of a rectangular cuboid or that is substantially semi-cylindrical, for example but without limitation.

The nasal chamber 226 defined within the nasal portion 220 preferably is larger than a typical nose to accommodate a variety of user's noses within the interior of the nasal portion 220. Preferably, the seal member 202 comprises a septum protrusion 228. The septum protrusion 228 extends forward (i.e., away the face when worn) in the region of the septum to define an enlarged recess on the inside of the seal member 202 in the region of the nasal septum of the patient.

The seal member 202 also preferably comprises an upper lip protrusion 230 that is positioned proximate the center of the upper lip. By providing one or more of the septum protrusion 228 and the upper lip protrusion 230, the nasal chamber 226 is enlarged at those locations to provide added clearance in the seal member 202.

With reference to FIG. 5, the sealing portion 212 of the illustrated seal member 202 can be shaped to substantially conform to a shape of a typical face. In the illustrated configuration, the sealing portion 212, which includes the flange 208, comprises a hollow region 232. The hollow region 232 can accommodate the chin of the patient. The hollow region 232 can cup the chin along a portion of the flange 208. With continued reference to FIG. 5, the illustrated sealing portion 212, which includes the flange 208, also comprises a valley 234 for the bridge of the nose. The valley 234 can comprise a curved wall that is generally C-shaped or U-shaped.

With continued reference to FIG. 5, the illustrated sealing portion 212, which includes the flange 208, comprises curving cheek portions 236 that extend between the hollow region 232, which is situated proximate the chin of the patient, and the valley 234, which is situated proximate the bridge of the nose of the patient. The curving cheek portions 236 can connect proximate the hollow region 232. In addition, the valley 234 lies between and, in some configurations, separates and connects the curving cheek portions 236.

FIG. 4 is a view of the exterior of the seal member 202. The exterior view better illustrates the enclosing portion 214. In the illustrated configuration, the seal member 202 incorporates cheek portions 238, a chin portion 240 and the nasal portion 220. The cheek portions 238 preferably spread laterally outward from the nasal portion 220. In use, the cheek portions 238 extend outward from the nasal region toward the zygomatic process of the patient. The cheek portions 238 also extend downward with lateral portions 239 toward the chin portion 240. Thus, the cheek portions 238 extend toward the mandible of the patient at a location outside of the lateral extremities of the mouth.

With reference again to FIGS. 4 and 5, the seal member 202 defines an aperture 242 that extends from the exterior surface to the interior surface of the seal member. The aperture 242 can be positioned at or lower than a location where the mouth of the patient might be positioned during use of the interface body 200. In some embodiments, the aperture 242 is positioned below the nasal chamber 226. The aperture 242 can be described as positioned below the septum protrusion 228. The aperture 242 further can be described as positioned below the upper lip protrusion 230. Moreover, the aperture 242 can be described as positioned above the hollow region 232 that accommodates the chin of the patient. Thus, the aperture 242 can be positioned between where the mouth of the patient might be expected and the tip of the chin of the patient. The aperture 242 preferably is positioned along a medial plane of the seal member 202, which medial plane generally bisects the seal member 202 into a right half and a left half. For reasons that will be explained below, the illustrated aperture 242 lies on a generally flat plane portion 244 of the seal member.

Supporting Member

With reference again to FIG. 2, the supporting member 204 overlies a portion of the seal member 202. The supporting member 204 is substantially more rigid than the compliant seal member 202 such that the supporting member 204 provides support to the compliant seal member 202. However, the supporting member 204 still can be somewhat flexible and the supporting member 204 preferably is not fully rigid. In some configurations, the supporting member 204 has a similar stiffness to an approximately 1 mm thick sheet of polypropylene or polyethylene plastic material, for example but without limitation.

As shown, the supporting member 204 comprises a perimetric edge 250. The perimetric edge 250 may have a similar shape to the perimetric edge 206 of the seal member 202 but, when a notch 252 is spanned and the spanning distance is included in the length of the perimetric edge 205, the perimetric edge 250 preferably has a shorter length compared to the perimetric edge 206 of the seal member. In other words, a total length of the perimeter of the supporting member 204 preferably is less than a total length of the perimeter of the seal member 202. Due to the inclusion of the upper portion of the nasal portion 220 in the perimeter of the seal member 202, the total length of the perimeter of the supporting member (even including the dimensions of the notch 252) is less than a total length of the perimetric edge 206 of the supporting member 204.

In some configurations, the seal member 202 extends outward beyond the supporting member 204 in all locations. As illustrated in FIG. 6, the radius $R_2$ can be defined with a spacing RO of between about 3 mm and about 6 mm defined from the perimetric edge 250 of the supporting member 204 to an outside surface of a rolled over portion of the seal member 202.

Figure 10:
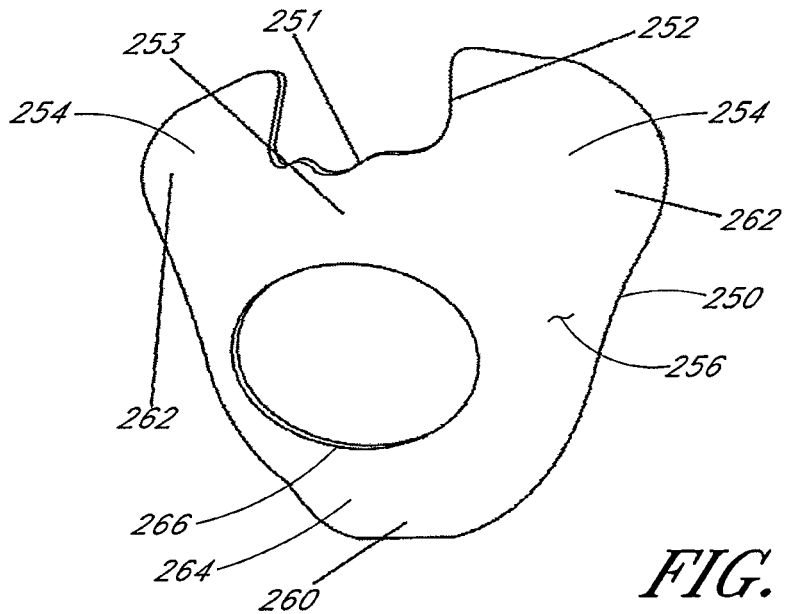
FIG. 10 is a front perspective view of an outside of a supporting member of the interface body of FIG. 2.
Figure 11:
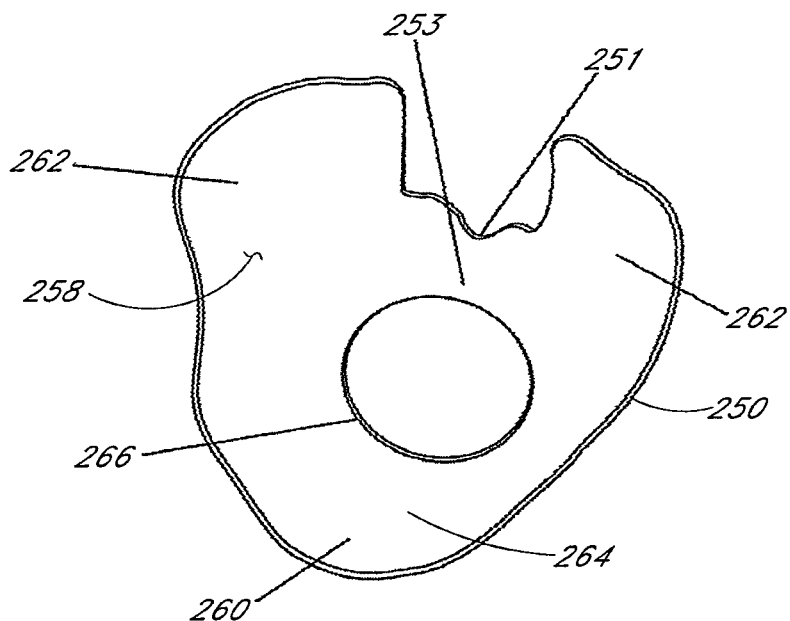
FIG. 11 is a rear perspective view of the inside of the supporting member of the interface body of FIG. 2.

As shown in FIGS. 10 and 11, the illustrated supporting member 204 comprises a contoured plate-like appearance. In other words, the supporting member 204 has form in three dimensions yet does not have a high level of relief. Preferably, the supporting member 204 has a total depth of relief of less than about 50 mm and about 65 mm in an interface sized for an average adult interface.

The otherwise generally smooth and continuous appearance of the perimetric edge 250 is interrupted by an upper notch 252. The notch 252 is positioned in the region of the nose of the patient. Thus, in the illustrated embodiment of FIG. 2, the supporting member 204 does not include a portion that resembles a human nose. By not comprising the human nose portion, the supporting member 204 has an improved bulk flexibility. Instead, the shape of a human nose is defined by the seal member 202 or some other component of the interface body 200. The notch 252 improves the flexibility of the support member 204. Thus, if there are different cheek bone angles, the support member 204 will flex slightly to better fit the patient.

In the illustrated configuration, the nasal portion 220 of the seal member 202 protrudes from the upper notch 252 in the support member 204. The shape of the illustrated notch 252 in the support member 204 accommodates the shape of the nasal portion 220 the seal member 204. The notch 252, by removing a nasal portion of the support member 204, provides the support member 204 with a shape that has minimal curvature from front to back (i.e., the support member 204 has a low profile and small depth of relief when formed).

In overall impression, the illustrated configuration provides a full face interface that resembles the human form while functioning to assist in controlling the ballooning of the seal member 202 by supporting the enclosing portion 214 of the seal member 202. The external appearance of the interface in use is of being partially human, thereby improving the emotional response of patients and of people observing the patient using the interface. Importantly, this may improve acceptance of the interface by patients and thereby improve compliance.

The notch 252 preferably defines a recess that extends inward from the perimetric edge 250 of the supporting member 204. In the illustrated configuration, the notch 252 extends inward toward a center of the interface body 200 or at least a center of the supporting member 204. The notch 252 may include an extended notch portion 251 to accommodate the septum. Other suitable profiles also can be provided to the notch 252 as desired. In some configurations, the notch 252 may be positioned above a ridge 253 that defines a valley on the inside of the support member 204 to further accommodate the central portion of the upper lip.

In the illustrated supporting member 204, the notch 252 is flanked by a pair of upward extensions 254 that are separated by the notch 252. Preferably, the upward extensions 254 define an uppermost extent of the support member 204. More preferably, the upward extensions 254 define an uppermost portion of the interface body 200 with the exception of portions of the very flexible seal member 202.

With reference to FIG. 2, the nose N of a patient P is illustrated in broken lines. The nose N protrudes into the chamber 226 defined by the nasal portion 220 of the seal member 202 while the notch 252 of the support member 204 crosses the medial plane at a location below the nose N. The upward extensions 254 of the support member 204 extend upwardly beyond a base B of the nose. In the illustrated configuration, the upward extensions 254 extend upward beyond a portion of the interface body 200 that is designed to accommodate a tip of the nose N of the patient P.

The lateral side edges of the notch 252 extend alongside lateral margins of the nose N such that the compliant seal member 202 can extend along the cheekbones and such that the support member 204 can reinforce the seal member 202 in the cheekbone region. Support of the interface body 200 on the cheekbones of the patient P can significantly improve the comfort level experienced by the patient P.

The upward extensions 254 also provide a stabilizing function and define, at least in part, means for stabilizing the illustrated mask on a central portion of the face of the patient. In particular, the upward extensions 254 roughly correspond to or overlap with a location of the maxilla bones of the skull.

The support member 204 generally conforms to a typical lower portion of a human face. As such and with reference to FIGS. 10 and 11, an outer surface 256 of the support member 204 has a generally convex appearance while an inner surface 258 of the support member 204 has a generally concave appearance. The inner surface 258 of the support member 204 generally conforms to an outside surface of the seal member 202. A chin portion 260 of the support member 204 can comprise a hollow concavity along the inner surface 258 of the support member 204. In addition, each of a pair of cheek portions 262 comprises a hollow concavity along the inner surface 258 of the support member.

The perimetric edge 250 of the support member 204 generally extends outside of the cheek portions 262 to outside of the chin portion 260 and generally follows inside a jaw line of the patient. As such, the illustrated perimetric edge 250 of the support member 204 extends to a chin of the patient P. Preferably, a lower portion 264 of the support member 204 hooks under the chin of the patient P. By hooking under the chin of the patient P, the support member 204 assists the seal member 202 in sealing in this region of the face of the patient P. The illustrated support member 204 defines an expanse of material that backs the seal member 202 and reinforces the chamber defined by the enclosing portion 214 of the seal member 202. In some configurations, the support member 204 defines a reinforcing rim that generally encircles a portion of the seal member 202.

Figure 3:
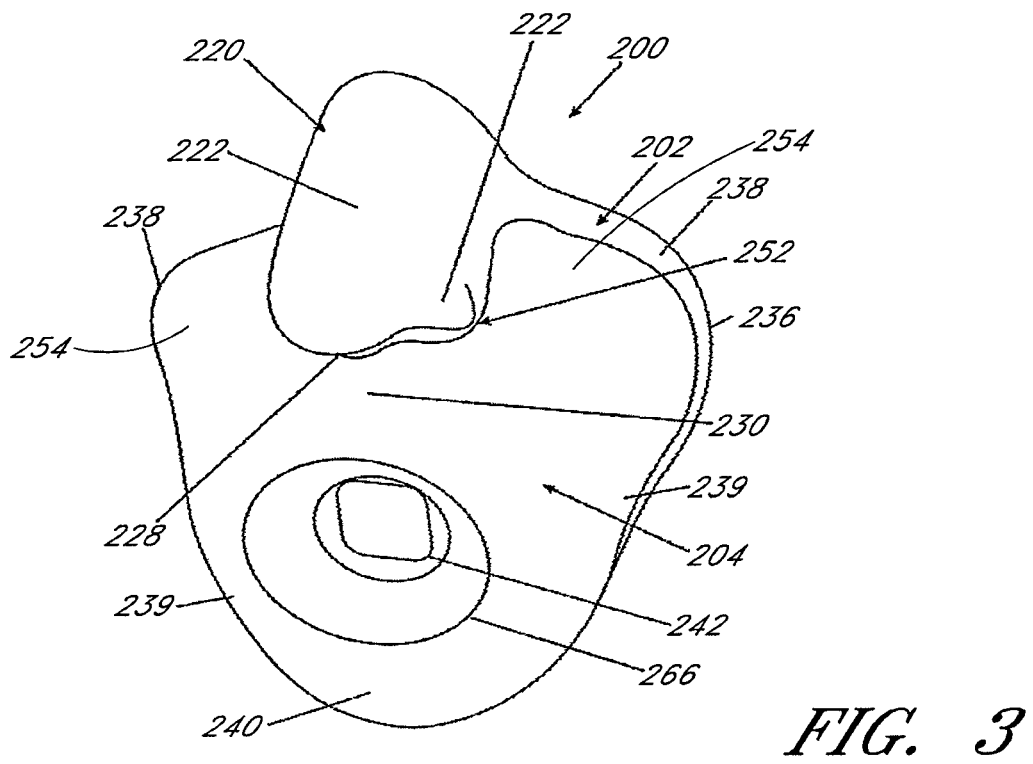
FIG. 3 is a perspective view of the interface body of FIG. 2.

As illustrated in FIGS. 2 and 3, the interface body 200 generally reproduces the general shape of the lower half of the user's face. The interface body 200 can cover the nose at the upper end. In some configurations, the interface body 200 is adapted to overlap with at least a portion of the nasal bone, which is the bone that extends above the cartilage of the nose and that is positioned between the eyes. At least the seal member 202 can include wings that extend outward toward the zygomatic bone of the wearer such that the seal member 202 extends outwards to follow the cheekbones. The interface body 200 extends downward to follow the jaw line to where the lower portion 264 of the support member 204 hooks under the chin.

With continued reference to FIGS. 10 and 11, the supporting member 204 also comprises a generally centralized opening 266. The opening 266 is positioned generally below the notch 252. Preferably, the opening 266 is positioned along the medial plane of the interface body 200, which is the plane that divides the illustrated interface body 200 into substantially symmetrical bilateral left and right halves. In the illustrated configuration, the opening 266 and the notch 252 both are positioned along the medial plane. The medial plane intersects, and preferably bisects, the opening 266 and the notch 252.

The opening 266 in the supporting member 204 preferably corresponds in location to the aperture 242 that is defined through the seal member 202. The aperture 242 is shown more clearly in FIGS. 4 and 5. The aperture 242 provides a location for a breathing gases inlet and outlet to the chamber that is defined on the face side of the seal member 202. By being positioned on the flat plane portion 244, the aperture 242 facilitates convenient connection and sealing of a supply breathing tube to the seal member 202. The support member 204 in the region of the opening 266 also may be configured to support the connection of the supply breathing tube (e.g., an elbow connector or other configuration of connector).

Bridge Section

Figure 13:
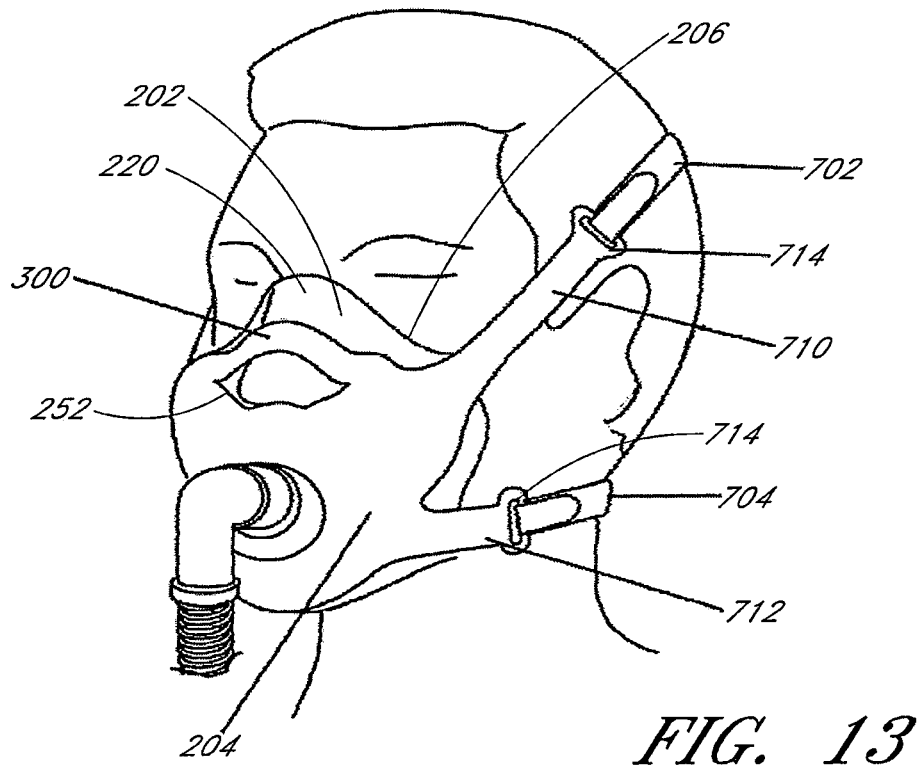
FIG. 13 is a front perspective view of another interface, which generally includes a modification of the interface body of FIG. 2, fitted to a user using headgear that is arranged and configured in accordance with certain features, aspects and advantages of the present invention. The illustrated interface is shown with a breathing tube or supply conduit attached.

With reference to FIG. 13, some embodiments of the supporting member 204 may also include a bridge section 300 that extends at least over the seal member 202 in the region of the notch 252. Thus, in some embodiments, the bridge section 300 may be positioned near the perimetric edge 206 of the seal member 202 in the region of the nasal portion 220. The bridge section 300 may provide additional support for the inflating seal member 202 in this region. The additional support can be useful in reducing the likelihood of air leaks along the sides of the nose, which air leaks may direct air in the general vicinity of the eyes of the patient.

Figure 14:
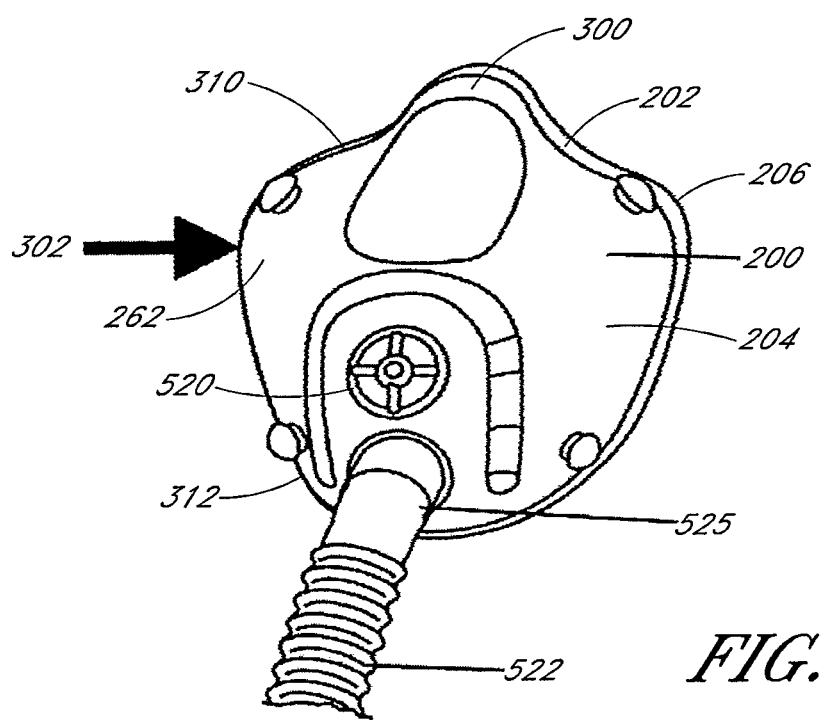
FIG. 14 is a front perspective view of an interface that is arranged and configured in accordance with certain features, aspects and advantages of the present invention with a breathing gases entry port located on a lower portion of the interface, which entry port is adapted to be positioned in a vicinity of a chin of a user.

With reference to FIG. 14, the bridge section 300 in this embodiment extends over the seal member 202 near the perimetric edge 206 of the seal member 202. The bridge section 300 shown in FIG. 14 preferably is between about 5 mm and 6 mm wide. The embodiment of FIG. 14 provides increased flexibility to the support member 204 and the seal member 202, which provides greater conformability to a wearer's facial geometry. In other words, the supporting member 204 has a lower flexible stiffness, which allows the interface 200 to flex under a retention force provided by headgear straps while the bridge portion 300 provides support for the seal member 202 in or proximate to the nasal portion 220. The bridge portion helps to reduce the likelihood of deflection of the seal member 202 at the bridge of the nose, which deflection can result in air leaks that are directed toward the general vicinity of the eyes.

With continued reference to FIG. 14, a load 302 applied in a lateral direction while the opposite side of the mask is held stationary causes flexing of the interface 200 about the medial plane. In the illustrated embodiment, the flexing reduces the overall width of the interface 200. The force 302 is applied at a location near the cheek portion 262 of the interface 200. Preferably, the force 302, when having a magnitude of about 1 N, will result in at least about 4 mm or more preferably at least about 5 mm of displacement when measured generally parallel to the direction of the force 302. While headgear generally does not apply the force 302 in the direction of the arrow, it has been found that the described flexing can be found in the interface 200. It also has been found that the flexing can help achieve an improved seal of the sealing member 202 over a wide range of facial geometries.

Preferably, the flexing or bending is about the medial plane. In some embodiments, it is preferable that the interface 200 is more flexible or deformable in the cheekbone region of the interface 200 (i.e., in an upper portion) compared to the jawbone region of the interface 200 (i.e., a lower portion). Such a difference in flexure zones can be achieved by the notch 252. Thus, the notch 252 can be used to provide an interface that is more deformable in the cheekbone region where greater anatomical variation may be expected and where the face is more sensitive to discomfort.

Figure 15:
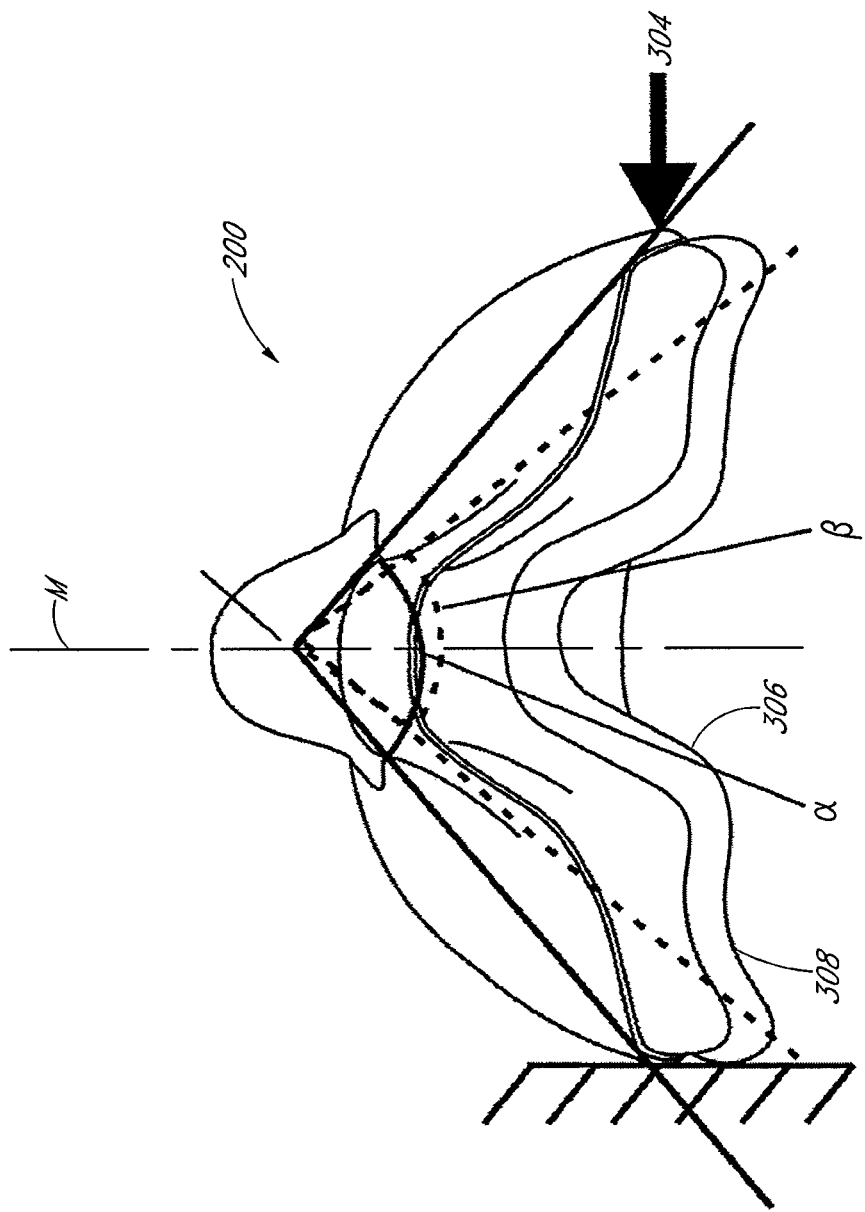
FIG. 15 is a top view of an interface that is arranged and configured in accordance with certain features, aspects and advantages of the present invention, which interface is shown in one or more bending modes.
Figure 23:
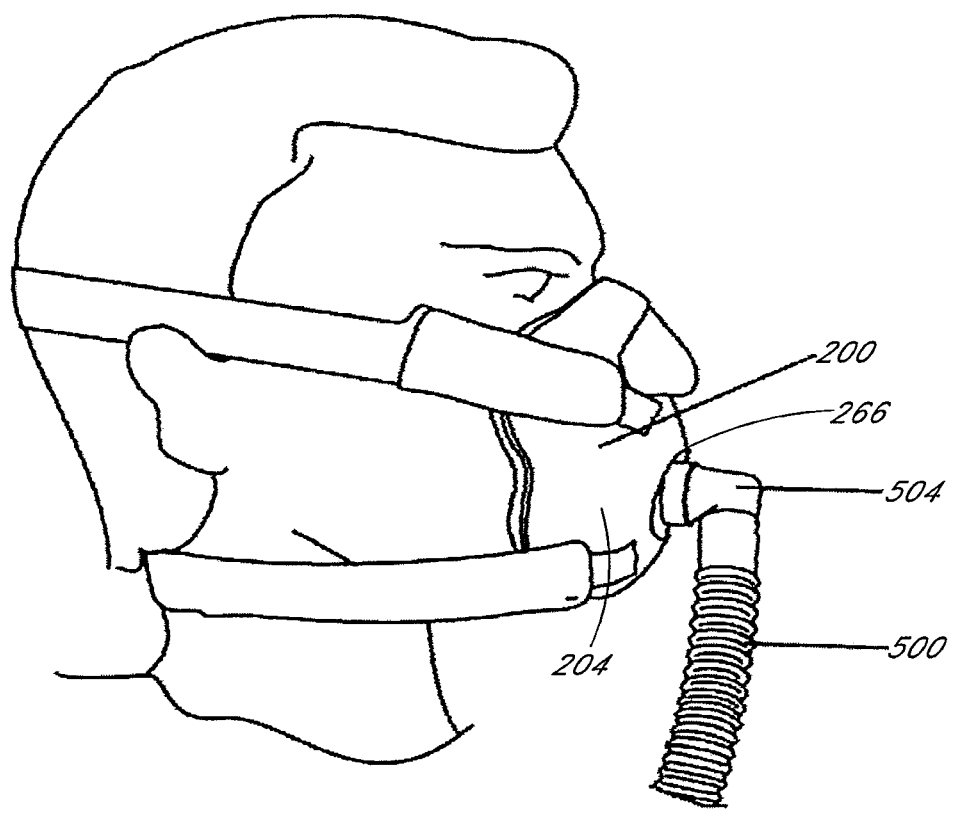
FIG. 23 is a side view of an interface and headgear that is arranged and configured in accordance with certain features, aspects and advantages of the present invention with a breathing tube or supply conduit that is connected to the interface with an elbow connector.

With reference now to FIG. 15, the interface 200 is capable of flexing up to approximately 20 degrees under typically encountered forces from headgear when in use. For example, FIG. 15 illustrates the interface 200, which comprises the seal member 202 and the supporting member 204. The supporting member 204 preferably is sufficiently flexible to deform substantially about the medial plane M. The interface 200 that is shown in FIG. 15 from a top down view also is shown in perspective view in FIG. 14 and in side view in FIG. 23. As illustrated, the illustrated interface 200 comprises a generally triangular appearance from the top down view of FIG. 15. In addition, a recess 306 is formed along a base 308 of the triangle in this view. Of course, the recess 306 is configured in accommodate at least a portion of the nose of the patient. In the side view of FIG. 23, the interface 200 comprises a generally square or truncated pyramid shape. In some configurations, no significant recess can be identified along the interface when viewed from the side. The illustrated configuration results in an interface that is significantly more flexible about the generally vertical medial plane when compared to the flexibility about a generally horizontally extending plane. Moreover, the illustrated configuration results in an interface that is longer from top to bottom than wide from the outermost cheek portion to the outermost cheek portion and that has an upper perimeter surface 310 that is generally triangular (i.e., the upper portion of the perimetric surface that extends between the cheek portions is generally triangular when viewed from the front) and a lower perimeter surface 312 that is generally triangular (i.e., the lower portion of the perimetric surface that extends between the cheek portions is generally triangular when view from the front). The upper perimeter surface being generally triangular and the lower perimeter surface being generally triangular along with the nasal portion and the chin portion being recessed relative to the cheek portions provide a configuration that is significantly more flexible about the vertical medial plane when compared to the flexibility about a horizontally extending plane.

As illustrated in FIG. 15, the left hand side of the interface 200 is braced to reduce the likelihood of movement and a force 304 is applied. Preferably, the force 304 is applied at approximately the widest point of the interface 200, which generally corresponds to the cheekbone portions. With the force 304 applied, the interface 200 preferably deforms such that angle $\alpha$ changes to angle $\beta$ (i.e., the change in angle is $\alpha-\beta$). In one embodiment, the change from $\alpha$ to $\beta$ is at least about 10 degrees when the force 304 is applied at a 3 N magnitude. In a more particular embodiment, strap forces typical of an interface in use are believed to be capable of causing a deformation of approximately $\alpha-\beta=10°$ to 50°. In a further embodiment, $\alpha-\beta$ is at least approximately 10° to 30° under typical strap forces of about 1.5 N to about 15 N per strap assuming four straps are used.

In one embodiment, the force 304 with a 1 N magnitude is capable of deforming the interface 200 at least about 5 mm. In a further embodiment, the force 304 with a 3 N magnitude is capable of deforming the interface 200 between about 5 mm and about 50 mm. In another further embodiment, the force 304 of 3 N magnitude is capable of deforming the interface 200 between about 15 mm and about 25 mm.

In use, the deflection of the supporting member 204 may occur to close or open the shape of the interface. In some embodiments, the force applied to open the interface 200 a given amount may be less than the force applied to close the interface 200 by the same amount. For example, in one embodiment, a force applied in a direction opposite of force 304 (i.e., an opening force) of 1 N magnitude is capable of deforming the interface 200 at least about 3 mm. In a further embodiment, an opening force of 3 N magnitude is capable of deforming the interface 200 between about 3 mm and about 25 mm. In another further embodiment, an opening load of 3 N magnitude is capable of deforming the interface between about 10 mm and about 20 mm.

Figure 12:
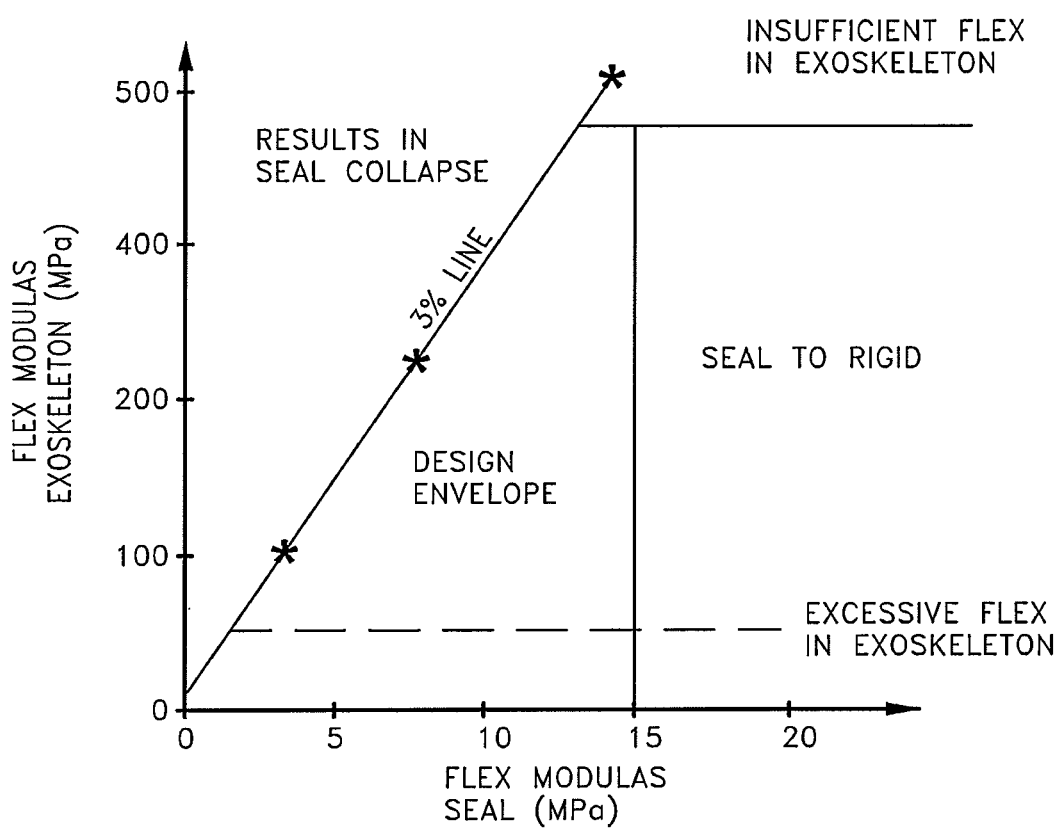
FIG. 12 is a graphical depiction of properties relating to the interaction of a support member flexibility and a seal member flexibility.

With reference to FIG. 12, a flex modulus of the supporting member 204 and a flex modulus of the seal member 202 can be interrelated. As shown in the graphical illustration of FIG. 12, the flex modulus of the material that forms the seal member 202 preferably is less than about 15 MPa. At levels that significantly exceed about 15 MPa, the seal member 202 has been found to be too stiff or rigid. On the other hand, the flex modulus of the support member 204 preferably is less than about 480 MPa. At levels that significantly exceed about 480 MPa, the support member 204 has been found to be too stiff or rigid. In addition, the flex modulus of the support member 204 preferably is above about 50 MPa. At levels significantly less than about 50 MPa, the support member 204 exhibits excessive flexure. Finally, in defining flexure characteristics that are desired in both the support member 204 and the seal member 202, it has been found that a desired interrelationship can be found within the hatched envelop shown in FIG. 12.

Flexible Interface Support

Historically, an ability of an interface to seal on a face of a patient has been hindered by difficulties in conforming to the facial geometry of the patient. The result of the inability to accurately conform the interface to the particular facial geometry of the patient is excessive leaking between the interface seal and the patient's face. With prior interface configurations, tightening of headgear can result in a force vector on the interface that unevenly loads the seal contact surface on the face of the patient. Uneven loading of the seal contact surface can result in pressure points in some locations and in inadequate pressure in other locations. The pressure points may result in irritation of the skin of the patient while the locations of inadequate pressure are likely to lead to leakage.

With reference to FIGS. 16-21, several embodiments of interfaces 200 are illustrated that present structures that enhance the ability of the interfaces 200 to conform to and seal with the face of the patient more evenly. The structures also enhance the ability of the interfaces 200 to conform to a wide variety of face geometries. Preferably, more even distribution of seal pressure can be achieved by applying a composite construction to the interfaces 200. Thus, the interfaces 200 can flex and contort to accommodate different facial geometries while allowing the sealing member 202 to inflate or balloon between the support member 204 and the face, thereby more evenly distributing the headgear fitting force onto the interface between the sealing member and the skin.

Figure 16:
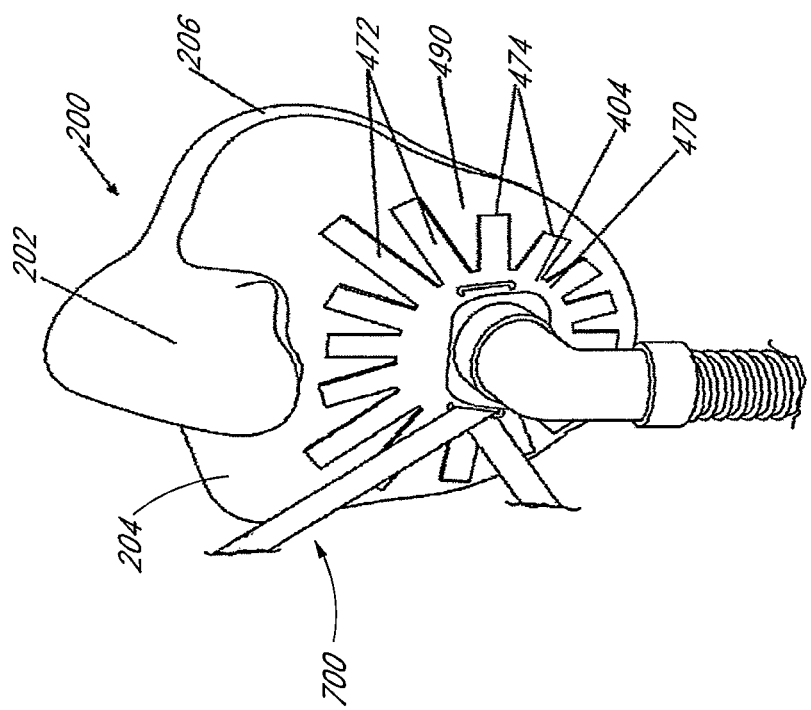
FIG. 16 is a front perspective view of another interface that is arranged and configured in accordance with certain features, aspects and advantages of the present invention. The interface is illustrated with headgear straps shown on only one side.

As shown in FIG. 16, the patient interface 200 comprises the soft compliant seal member 202 and the support member 204, such as those described above. The seal member 202 is adapted in use to cover a nose and a mouth and to seal around a face along the perimetric edge 206 of the seal member 202. For the most part, the interface 200 shown in FIG. 16 is the same as the interface 200 shown in and described with respect to FIG. 2. In particular, the features of FIGS. 16-21 described below can be implemented with the interfaces 200 that are arranged and configured in accordance with the descriptions contained elsewhere in this application, for example.

An added support member 404 is provided over the seal member 202 or the support member 204 in order to provide support to the seal member 202. The support member 404 and the seal member 202 have a small wall thickness and are formed to be complimentary in shape such that the seal member 202 fits snugly underneath the support member 404. Preferably, in at least one embodiment, the outer profile or shape of the support member 404 and the seal member 202 substantially follow the contour of a typical face such that the interface 200 comprises a relatively low profile component. In some embodiments, the patient interface 200 may be more typical in size and dimensions.

The support member 404 comprises a central hub portion 470 that is connected to the support member 404. In some configurations, the central hub portion 470 can be directly connected to the seal member 202. Radiating outwards from the hub portion 470 are a plurality of displaceable members 472 or 'fingers' that are separated at the ends by spaces 490. The displaceable members 472 preferably are cantilevered from the hub portion 470 and extend outwards towards the perimetric edge 206. The displaceable members 472 preferably are not rigidly bonded or attached to the underlying seal member 202 so that relative sliding motion can occur between the seal member 202, or the support member 204 when present, and the displaceable members 472.

In some embodiments, the displaceable members 472 may be resiliently hinged rather than cantilevered. In such a configuration, the displaceable members 472 are moveable with respect to one another substantially in a front to back direction (with respect to a face when wearing the interface 200) such that a force applied by headgear acting on the hub portion 470 urges the interface 200 towards the face.

Preferably, the displaceable members 472 are made of a material that is significantly stiffer than the soft compliant seal member 202. For example, any typical polymer materials used in interface frames may be appropriate, such as polypropylene, polyethylene or polycarbonate, for example but without limitation. According to one variation, the displaceable members 472 may include elastic material extending between adjacent lateral margins of adjacent fingers 472 in a manner similar to a catcher's mitt. In other words, webbing of an elastic material may extend between adjacent fingers 472.

The plurality of displaceable members 472 function to distribute a load applied to the central hub 470 across the wider surface area of the interface 200 thereby providing a more localized force to press the perimetric edge 206 of the seal member 202 onto a user's face. In particular, because the displaceable fingers 472 are cantilevered from the hub 470 and because the displaceable fingers 472 provide significant front to back movement at the free ends, the support member 404, which includes the displaceable members 472, can conform to a face and can providing an adequate seal for a wide variation of facial geometries. The sliding movement of at least free ends 474 of the displaceable members 470 with respect to the underlying seal member 202 provides a mechanism by which the members 472 can put pressure on slightly different parts of the underlying seal member 202 depending upon the differing geometry of a user's face. Such a construction can increase the conformability of a given seal to a wide range of facial geometries.

If a wearer has a relatively flat face, it is easier to achieve a good seal. However, if a user has a face that includes large front to back variations in shape, the free ends 474 of the displaceable members 472 provide localized pressing forces at locations distant from the relatively central hub 470 such that the forces from the headgear can be transmitted from the hub 470 to the free ends 474.

In some configurations, multiple hub portions 470 may be located non-centrally on the interface with each hub portion 470 having displaceable members 472 extending therefrom. For example, the chin and left and right cheeks are preferable places to load a user's face and the interface may include hub portions 470 at one or more of these locations.

Figure 17:
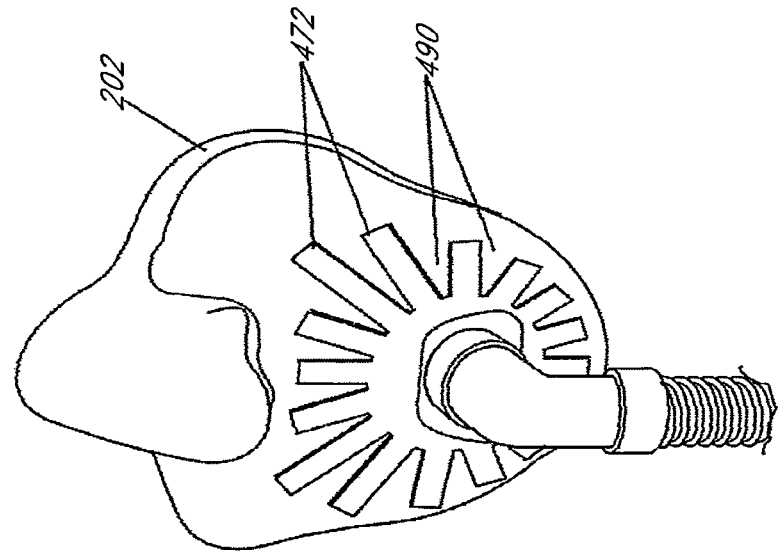
FIG. 17 is a front perspective view of an interface that is arranged and configured in accordance with certain features, aspects and advantages of the present invention. The interface is illustrated without headgear straps.
Figure 18:
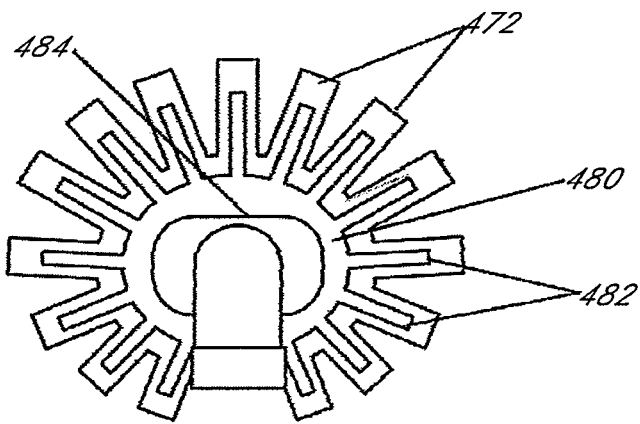
FIG. 18 is a front view of a portion of an interface similar to that of FIGS. 16 and 17 with a supporting member that is arranged and configured in accordance with certain features, aspects and advantages of the present invention.

With reference now to FIG. 18, a further support member 480 can be applied to the support member 404 shown in FIGS. 16 and 17. In some configurations, the support member 480 can be secured to the support member 404 to form a laminate-type structure. The support member 480 can comprise a plurality of displaceable members 482 that are moveable with respect to each other and/or at least an inner hub portion 484 of the further support member 480. Preferably, the fingers 482 of the further support member 480 bear on the fingers 472 of the support member 404. While the illustrated configuration shows the same number of displaceable members on the support member 404 and the additional support member 480, the number and placement of the displaceable members can vary. In some embodiments, the plurality of displaceable members associated with the further support member 480 may bear directly on the seal member 402.

It will be appreciated that embodiments may be constructed where combinations will be present. In other words, some of the plurality of fingers (either of the support member or of the further support member) may bear directly on the seal or may bear on other fingers. For example the interface 200 illustrated in FIG. 16 includes the support member 204 interposed between the seal member 402 and the support member 404 (and/or further support member (not shown)). In this embodiment, the free ends 474 of the support member (and/or further support member) bear on the support member 204, which in turn applies pressure to the underlying seal member 402. The support member 204 serves to further spread the loading forces across the seal member 402 and/or support the softer seal member 402.

Figure 19:
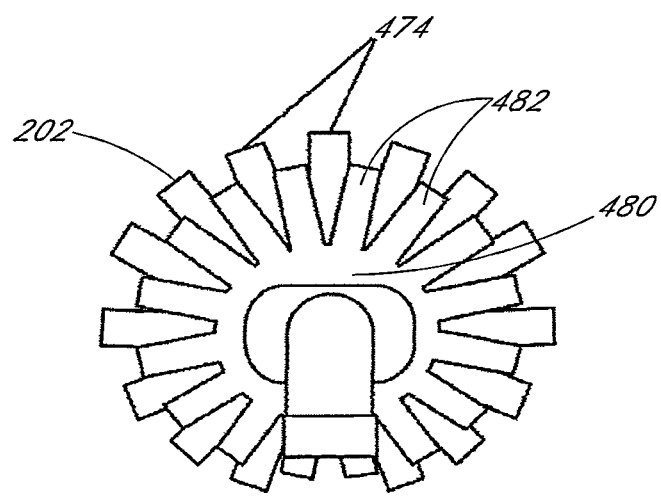
FIG. 19 is a front view of a portion of an interface similar to that of FIGS. 16 and 17 with a supporting member that is arranged and configured in accordance with certain features, aspects and advantages of the present invention.
Figure 20:
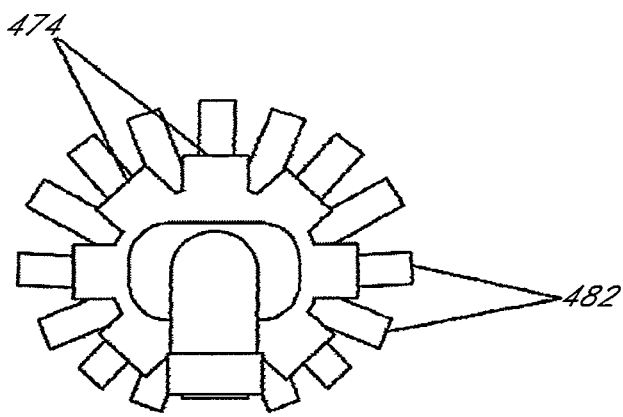
FIG. 20 is a front view of a portion of an interface similar to that of FIGS. 16 and 17 with a supporting member that is arranged and configured in accordance with certain features, aspects and advantages of the present invention.

In an alternative embodiment shown in FIG. 19, the free ends 474 of the support member (and/or further support member) can bear directly on the compliant seal member 202 beneath. In the embodiment shown in FIG. 20, the free ends 474 of the fingers bear on the underlying displaceable members 482 of the further support member. Any other suitable variations also can be used.

Figure 21:
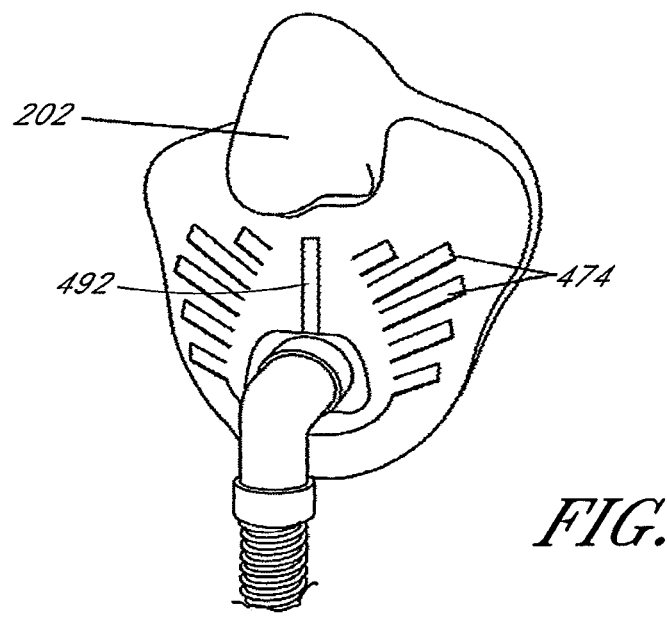
FIG. 21 is a front perspective view of an interface with a support member that is arranged and configured in accordance with certain features, aspects and advantages of the present invention.

The above description gives only a few examples of interface seal types where displaceable members can provide improved facial fit and/or improved sealing. Other configurations also are possible. The number, spacing and width of the displaceable members can be varied. In addition, while the example embodiments illustrated in FIGS. 16-21 all show support members (and further support members) that are generally circular in plan view, and/or illustrate displaceable members that radiate generally from a central location, other shapes are possible. For example, rather than a central generally circular hub, a linear or generally rectangular hub may be employed. In such an embodiment, the displaceable members 474 may radiate outwards in a 'leaf like' structure or like the branches of a tree as shown in FIG. 21, for example but without limitation. In such an embodiment, it may be preferable that the hub is substantially aligned with a mid sagittal plane of a user when wearing the interface. In addition, the hub may include one or more a semi-rigid reinforcing ribs 492 to substantially stiffen the "trunk" of the structure. The inclusion of the trunk reinforcing rib 492 provides a beam to resist bending in a given direction.

In a further alternative embodiment the displaceable members may be constructed having a variable thickness in order to tailor the stiffness of the cantilevered sections with respect to bending the front to back direction. For example, the material thickness of the fingers may decrease towards the free ends. Similarly, the fingers may or may not have a substantially rectangular plan profile as illustrated in the figures. For example, the width of the displaceable members may narrow towards the free ends or may have differing shapes to provide a desired level of displacement.

In a further alternative embodiment, the free ends of the displaceable members described in the above embodiments may further include features where the free end bears on the sealing member or on an underlying further support member. For example, a compressible material pad may be located between the free end and the seal surface such that the compressible pad bears on the seal member. In another example, the free end may be rounded at the point of contact between the free end and the seal member. Alternatively, the free end may include a compliant member that bears on the seal. The compliant member may be foam or a plurality of small compressible hoop structures for example.

The forgoing describes example of the interface support that can be applied in combination with the reproduced nose interface described earlier. The interface support can be used with other interface configurations having a soft compliant seal. For example, it is not necessary to have a support body in between the seal and the displaceable support members. In at least one embodiment, this configuration is preferable. In other words, the displaceable support members may act directly on the compliant seal at specific locations to press the interface seal against a users face. Similarly, the interface support is not limited in application to any single head gear configuration. The general purpose of the interface support is to distribute the force applied by the headgear to substantially a single location over a wide area and, as such, the disclosed configurations can define means for distributing a localized force over an interface body. In particular, the interface support can distribute the force over a wide area and/or also accommodate a large variation in facial contours in the front to back direction.

Breathing Tube Connections

Figure 22:
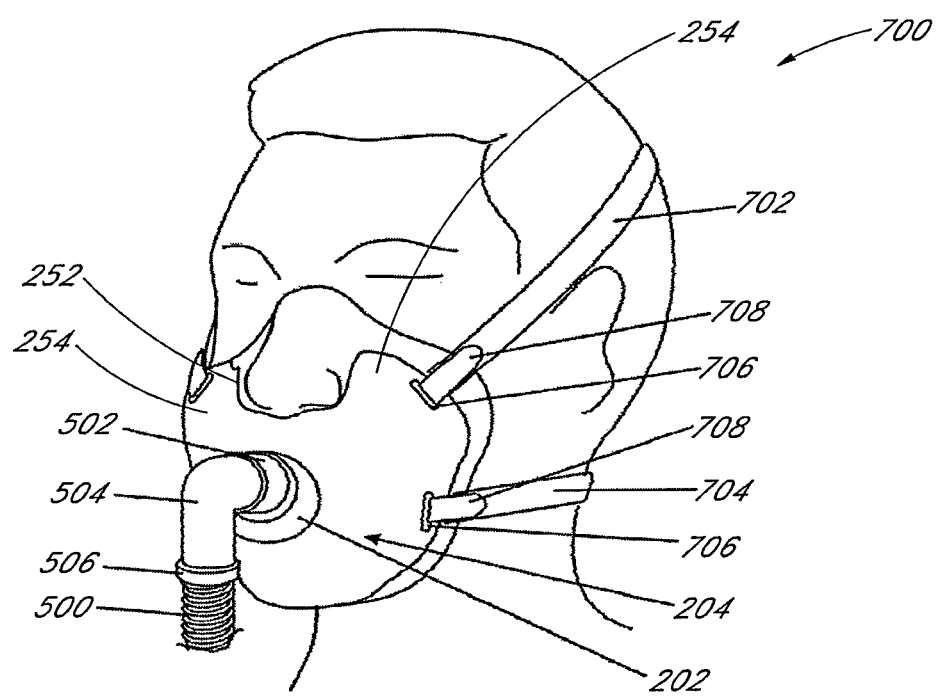
FIG. 22 is a front perspective view of an interface, which includes the interface body of FIG. 2, fitted to a user using headgear that is arranged and configured in accordance with certain features, aspects and advantages of the present invention. The illustrated interface is shown with a breathing tube or supply conduit attached.

With reference now to FIGS. 14 and 22 a breathing tube 500 is shown connected to the interface 200 in at least two different manners. The connections that will be described between the breathing tube and the interface can be interchanged. In addition, any of the described connections can be used with any of the described interfaces.

With reference initially to FIG. 22, the illustrated breathing tube 500 is connected to a breathing tube connector with an elbow 504. The breathing tube connector can be fitted to and sealed with the aperture 242 of the seal member 202. Because the breathing tube connector is secured to the aperture 242, the breathing tube connector extends through the opening 266 formed in the support member 204.

In some configurations, a snap fit arrangement is provided wherein a semi-rigid section of the connector protrudes through the aperture 242 in the seal member 202 from one side of the seal member 202 while another semi rigid section of the connector can be snap fit to the first semi-rigid member. In some configurations, any other suitable technique for bonding may be used to form a boss on the soft compliant seal member 202 and the connector can be connected to the boss. The elbow 504 can be connected to the connector.

In FIG. 22, the interface body 200 is shown with the breathing tube 500 is connected to the connector with the elbow 504, which connector may be connected to the seal member 202 or to seal member 202 and the support 204. A swivel 502 allows the elbow 504 to rotate relative to the interface body 200 so the supply conduit 500 can take up different orientations with respect to the interface body 200, thereby improving user comfort during movement, for example but without limitation. A further swivel 506 may be provided between the elbow 504 and the breathing tube 500.

The interfaces described herein also can be used with a bi-directional flow ventilator with the conduit 500 being short and being connected to a Y-piece. In addition, with a uni-directional flow system provided, for example, by a CPAP machine, appropriate ventilation holes may be provided in the elbow 504 or in a region near the bridge of the nose of the seal member 202. Moreover, rather than the swivel 502, a ball-joint type connection can be provided to allow articulation between the breathing tube 500 and the interface body 200.

In some configurations, such as that illustrated in FIG. 14, the interface body 200 may include an anti-asphyxiation valve 520. The anti-asphyxiation valve 520 may be associated with the interface body or, in some embodiments, may be incorporated into the breathing conduit connection or into the elbow connector, for example but without limitation.

While suitable for use, the connection using the elbow 504 results in the breathing gases entering the interface body 200 substantially horizontally. Accordingly, the breathing gases are directed straight towards the patient's mouth. It has been found that this arrangement has several disadvantages. For example, patients may feel uncomfortable having breathing gases directed straight at their face or mouth. Additionally, the elbow connector 504 is attached to the front of the interface body 200 and projects outwardly away from the user's face a distance. The top of the interface body 200 (i.e., the nasal portion 220 of the interface body 200), where the seal member 202 interacts with the nose, is a portion that is difficult to seal due to considerable anatomical variations among patients. As a result, the bridge of the nose is a common site for interface leakage. Any torque applied the interface body 200 may aggravate the sealing problem in this region. In order to compensate for this effect, it is common to overtighten the headgear to push the interface body 200 tightly onto a patient's face. The overtightening can lead to discomfort, which is highly undesirable.

With continued reference to FIG. 14, in this embodiment, connection to the breathing tube 500 can be made with a short flexible tube 522 that connects directly to the breathing tube and that enters the interface body 200 in the vicinity of the wear's chin and at an angle (projecting downwards from a wearer's chin). Thus, the gases enter the interface in a direction that is upwards and towards a patient's mouth and nose. In other words, the tube 522 extends downwards and away from the patient.

The flexible tube 522 connects to the interface body through a port 525. The port 525 is located below a line extending directly outwards through a patient's mouth when facing forward in a normal position. Preferably, the conduit 522 enters the interface body 200 through the port 525 at an angle between about 0° and about 70° from vertical. In some configurations, the entry angle is between about 50° and about 60°. Preferably, the entry angle is about 55°.

Preferably the gases port 525 is located in the vicinity of the patient's chin (i.e., between the patient's lower lip and the tip of the chin,). This port location advantageously positions the port 525 such that the front of the interface body 200 has more room for attachment mechanisms, such as holes, posts, loops, clips and the like. In addition, this port location also provides more room for the anti-asphyxiation valve 520 to be located forward of the mouth. Moreover, the location of the breathing gases entry port 525 in the vicinity of the lowest point of the interface interior when in use provides an effective vomit drain.

The short length of tubing 522 allows natural head movement of the patient by being very flexible and making the location of the connection between the patient interface 200 and breathing tube 500 distant from the interface itself. The connection between patient interface 200 and breathing tube 500 can be achieved via rigid connectors of a known type. Positioning these connectors away from the chin and neck of a patient improves the patient's head mobility, especially when tilting the head forwards.

Any other suitable technique of supplying pressurized gases to the interface body also can be used.

Interface Flow Control

Figure 25:
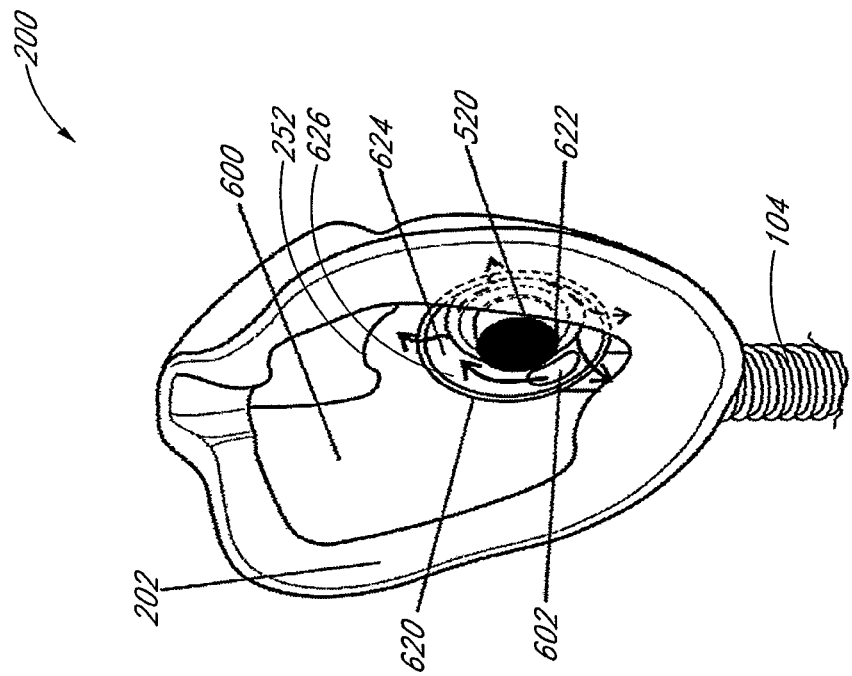
FIG. 25 is a rear perspective view of an interface that is arranged and configured in accordance with certain features, aspects and advantages of the present invention. The illustrated interface comprises a cyclonic flow inducing configuration.
Figure 24:
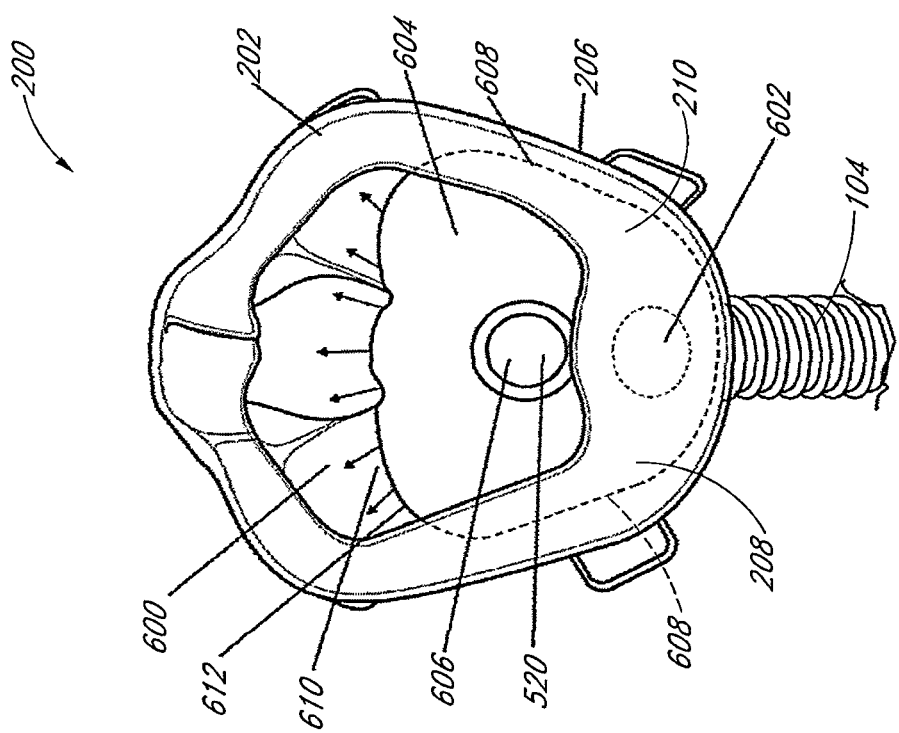
FIG. 24 is a rear view of an interface that is arranged and configured in accordance with certain features, aspects and advantages of the present invention. The illustrated interface comprises a plenum space with a diffuser port.

With reference now to FIGS. 24 and 25, diffusion and control of flow within the interface body 200 will be described. The interface body 200 can be configured in any suitable manner and, in the illustrated configuration, the interface body 200 comprises a cavity 600 defined within the interface 200 by the seal member 202, for example but without limitation. The seal member 202 can be configured in any suitable manner, including but not limited to those disclosed within this application. In use, the seal member 202 contacts and seals against the face of the patient. When sealed against the face, the seal member 202 reduces the likelihood of air or gases leaking out of the cavity 600.

The breathing tube or another short flexible tube 104 connects to the interface body 200 in any suitable manner, including but not limited to those described within this application. The breathing tube 104 supplies breathing gases to an entry port 602. The entry port 602 preferably is located in a region of the interface body 200 that will be located within the vicinity of the chin of the patient. More preferably, the entry port 602 is configured such that the breathing gases are introduced in an upwardly inclined direction rather than directly toward the face of the patient.

With reference to FIG. 24, the cavity 600 defined within the seal member 202 can be segmented by a partition wall 604. The partition wall 604 can be formed within the cavity 600 in any suitable manner. The partition wall 604 preferably is mounted or supported within the cavity 600 by a boss 606 or other suitable mounting structure. In such a configuration, the partition wall 604 is mounted at a location contained within a boundary defined by a peripheral edge 608 of the partition wall 604. In the illustrated configuration, the entire peripheral edge 608 is spaced from the inner wall of the seal member 202 or other interface wall defining the cavity 600.

The partition wall 604 can be offset from the inner wall such that a gap is defined between the partition wall 604 and the inner wall. The partition wall 604 preferably approximately follows the general shape of the cavity 600 such that a plenum space is defined by an approximately constant gap between the partition wall 604 and the inner wall. Preferably, the gap between the partition wall 604 and the inner surface of the cavity 600 is less than about 10 millimeters. More preferably, the gap is between about 3 millimeters and about 6 millimeters. In some configurations, an incident angle between the flow from the port 602 and the partition wall is between about 30° and about 80°. In some configurations, the incident angle is between about 50° and 70°. Preferably, the incident angle is about 60°.

A diffuser port or a diffuser outlet 610 can be defined by a space between the peripheral edge 608 of the partition wall 604 and the inner wall. In some configurations, the partition wall is generally circular and has a diameter of between about 30 mm and about 100 mm. In configurations, the diameter is between about 40 mm and 80 mm. The peripheral edge 608 of the partition wall preferably is sized and positioned to extend near to the outer perimeter of the seal member 202. More preferably, the peripheral edge 608 of the partition wall 604 extends into a region that is overlapped by the extended surface 210 defined by the flange 208.

The partition wall 604 also preferably is contained within the lower portion of the cavity 600. More preferably, an upper margin 612 of the partition wall 604 is positioned at or below the cheekbone level of the interface body 200. Even more preferably, the upper margin 612 of the partition wall 604 is generally aligned with a lowermost portion of the notch 252 for the nasal portion 220. Accordingly, the upper margin 612 can be positioned generally at the same position as the nose of the patient.

In the illustrated embodiment, the diffuser outlet 610 is substantially or completely contiguous about the entire partition wall 604. In some configurations, the diffuser outlet 610 can be defined solely along the upper margin 612 of the partition wall 604. In some configurations, the diffuser outlet 610 includes the region along the upper margin 612 such that the diffuser outlet 610 includes an upper diffuser port portion that causes breathing gases to flow substantially tangentially over the wearer's cheek bone region.

In some configurations, however, the partition wall 604 does not follow the contour of the inner surface of the seal member 202 and, therefore, the gap defined between the partition wall 604 and the inner surface of the seal member 202 is not substantially constant.

The entry port 602 provides gases from the breathing tube into the plenum space that is defined within the cavity 600. The entry port 602 leads into the plenum chamber that is defined between the partition wall 604 and the inner surface of seal member 202 or, where the seal member 202 is replaced by the support member 204 in a particular region of the interface body 200, the inner surface of the support member 204. Thus, the gases provided through the entry port 602 generally are prevented from flowing directly to a patient's mouth by the partition wall 604. Rather, the gases stream impacts the partition wall 604 and is deflected throughout the thin plenum chamber.

Where the inner wall that defines the cavity 600 and the partition wall 604 approximate the contours of the wearers face, the resulting diffused breathing gases flow is substantially tangential to the facial surface. The diffused breathing gases flow exits the plenum chamber through the diffuser port 610, which is defined by the gap between the inner cavity wall and the periphery 608 of the partition wall 604.

The plenum chamber functions as a means to evenly distribute breathing gases flow to the patient around the edges of the partition wall without substantially increasing resistance to flow. In interfaces that incorporate an inflating or ballooning seal, the diffuser port 610 that directs the flow radially outward from the entry port 602 instead of having the flow continue along the axis of the entry port 602 directs the flow toward and preferably onto the perimeter of the seal member 202, which helps seal the flange 208 to the face of the patient.

In some configurations, the partition wall 604 can be supported in a number of different locations (e.g., at least two or more locations). The partition wall 604 could be supported in such a manner that the diffuser port 610 includes distinct regions along the peripheral edge 608 of the partition wall 604 and/or along the upper margin 612 that are not a continuous open port. In other words, the diffuser port 610 may not be a continuous opening extending substantially around the entire perimeter 608 of the partition wall 604.

Preferably, the total cross sectional area of the diffuser port(s) 610 is greater than the cross sectional area of breathing gases entry port 602. With such a construction, the gases velocity decreases from the entry port 602 to the diffuser port 610. Preferably, the cross sectional area of the diffuser port 610 is at least twice the cross sectional area of the entry port 602. Even more preferably, the cross sectional area of the diffuser port 610 is between 2 and 5 times the cross sectional area of the entry port 602. The enlarging of the cross sectional area reduces the occurrence of ventilation synchrony issues and jetting effects on the patients. For example, the spreading and/or slowing of the gases flow, together with the tangential redirection of the gases flow over the wearer's skin, results in a more comfortable patient experience.

In some configurations, the partition wall 604 may comprise one or more small holes. The holes enable some gentle breathing gases to flow directly towards the mouth. Further, in some configurations, the plenum chamber may include flow directing features, such as partitions or the like, to aid concentration of the flow to particular areas of the face. For example, flow can be directed away from patient receptor area that would normally contribute to a hot and uncomfortable feeling during therapy. In addition, in some configurations, flow can be directed toward patient receptor areas that encourage feelings of flow over the face, which can mitigate a feeling of breathlessness or lack of airflow. In some applications, the flow can be diverted away from the nose using a flow directing feature. The flow directing features may be associated with the inner surface of the cavity and/or partition wall 904.

Preferably, the interface body 200 also comprises the anti-asphyxiation valve 520. The valve 520 may be incorporated into the partition wall supporting boss 606 in some configurations. In addition, in some configurations, the partition wall 604 can be made to flex, move or pivot such that incoming flow is dispersed by the partition wall 604 while exhalation can be channeled directly toward the port.

In some embodiments, the interface body 200 may be provided with one or more pressure monitoring ports (not shown) that is located on the exterior surface of the interface body 200. The pressure monitoring ports could extend through the plenum chamber and open into the gases cavity 600. In other words, the opening of the port preferably is positioned within the gases cavity 600 at a location outside of the plenum chamber defined between the partition wall 604 and the inner surface of the cavity. More preferably, the opening of the port is positioned along the partition wall 604 on the opposite side of the partition wall 604 from the plenum chamber. Placement of the pressure monitoring port behind the baffle wall or partition wall 604, yet in front of the face of the patient, can improve pressure monitoring accuracy. Such a placement also improves breath triggering or the like when used with a ventilator.

The partition wall 604 has been found to provide markedly improved acoustics in association with patient speech. It has been found that the plenum chamber defined by the offset partition wall 604 improves the interface acoustics, which enables a patient to be more easily heard when speaking. In addition, by diffusing the flow into the interface, the patient does not need to overcome jetting into the nose and/or mouth in order to speak. In other words, the patient does not need to overcome an incoming breath from a ventilator in order to speak.

Furthermore, due to the diffusion of the airflow, the plenum chamber arrangement provided by the partition wall 604 may help reduce condensate formation within the cavity 600. In addition, the arrangements for diffusing flow that are disclosed within this application have been found to reduce the likelihood of a collection of unwanted water vapor, water droplets and mobile water collecting upon the interface surfaces. With the diffused airflow, the condensed water or liquid can be directed flushed from the cavity 600 and directed toward the port or other collection or drainage location.

With reference now to FIG. 25, a further flow diffusing configuration is illustrated therein. In this configuration, breathing gases entering the interface body 200 are swirled around the cavity 600 to produce a cyclonic motion that preferably is substantially tangential to the surface of the face of the patient.

The interface body 200 comprises the gases cavity 600. The seal member 202 is configured to contact the face and to substantially seal the cavity 600 against the face. The breathing gases entry port 602 is located in the vicinity of the chin. The breathing tube delivers gases to the breathing gases entry port 602 as described elsewhere within this application.

The breathing gases entry port can be positioned within a gases swirling structure 620. The swirling structure 620 comprises substantially cylindrical wall 622 extending substantially perpendicular to the interface cavity wall. In other words, with a patient upright, the cylindrical wall 622 projects forward in a location substantially in front of the mouth of the patient. A substantially conical wall 624 extends coaxially with the cylindrical wall 622 and a swirling space 626 is defined between the cylindrical wall 622 and the conical wall 624. The conical wall 624 is angled such that the gap between the conical wall 624 and the cylindrical wall 622 is larger closer to the wearer of the interface.

In use, breathing gases enter the swirling space 626 through the port 602 in the conical wall 624. The port 602 is offset from the axis of the walls 622, 624 such that gas flow enters the swirling space 626 offset and approximately tangentially as shown. As a result, gases flow around the illustrated annular swirling space 626 in an anti-clockwise direction setting up a rotating flow. The inclined conical wall 624 urges the rotating flow towards the patient (i.e., in a direction out of the page in FIG. 25). As the flow rotates and moves towards the patient, the gas flow peels off the top of the conical wall 624, which results in a sweeping blade of air moving outwards and towards the patients face. The resulting flow across the wearers face is diffuse and preferably travelling slower than the gases stream entering the swirling structure. In some configurations, the flow of air toward the face of the patient is less than about 8 m/s. In some configurations, the flow toward the face of the patient is less than about 6.5 m/s. In a similar manner to the plenum chamber embodiment described earlier, the result is improved comfort for the patient.

Headgear

The interface body 200 can be secured on the patient using any suitable headgear assembly 700. Several different headgear assemblies now with be described with reference to the drawings.

Figure 26:
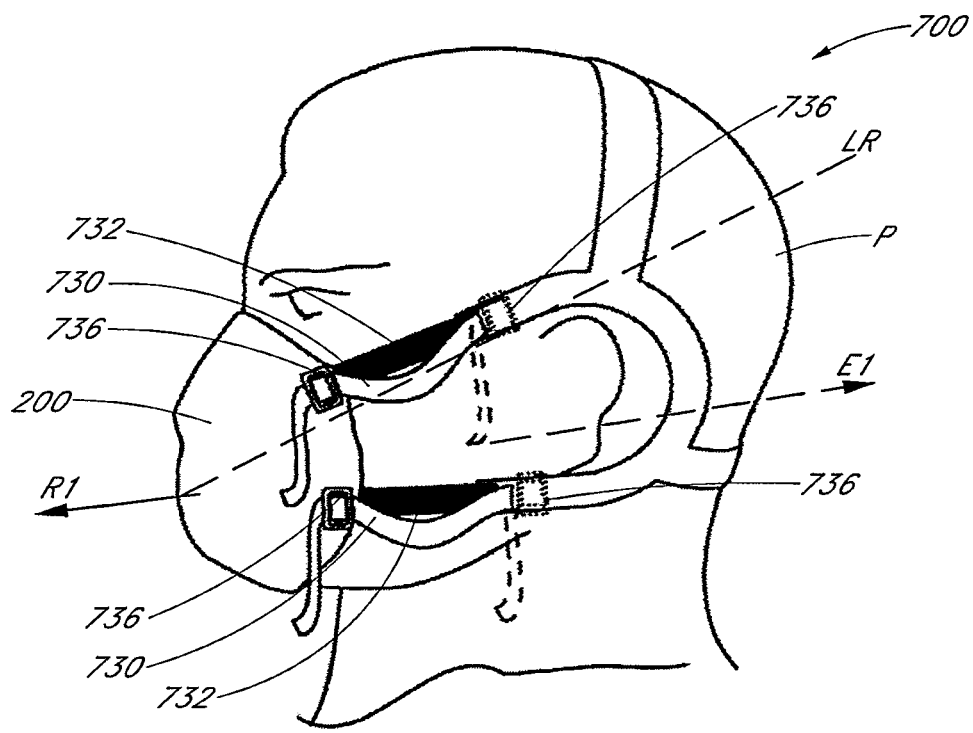
FIG. 26 is a side view of an interface and headgear that is arranged and configured in accordance with certain features, aspects and advantages of the present invention.

Initially, with reference to FIG. 26, it can be seen that the headgear assembly 700 is used to restrain the interface body 200 against movement created by the pressurized gas flow being introduced between the patient P and the interface body 200. A force vector R1 results from the geometry of the interface body 200 and the flow of gases into the interface body 200. An equilibrant vector E1 can be envisaged extending in the opposite direction. Ideally, a single strap could be used to secure the interface body 200 to the face so long as the single strap was positioned along the line of action of the equilibrant vector E1. Given a desire to capture the chin, a line of retention LR also can be envisioned. The line of retention LR extends along an uppermost portion of the ears and through a center of area of the interface body 200.

Preferably, the interface body 200 is primarily supported on at least three parts of the patient's face: left cheekbone, right cheekbone and chin. Preferably, the strap attachment positions on the interface body 200 approximately correspond to the vertical positions of the cheek bones for the upper straps and the chin region for the lower straps. Such a configuration provides a symmetrical force pattern by which the headgear retains the interface on the patient's face.

While some of the headgear assemblies 700 that will be described can comprise a single strap that extends generally along the line of retention LR, other headgear assemblies 700 will comprise two or more straps (e.g., FIGS. 13, 16, 22, 23, 26 and 27). For example, in the configuration of FIG. 16, the headgear assembly 700 comprises a strap that extends in two directions from the interface body 200 in order to secure the interface body 200 to a user's face. While the strap is shown on only one side for convenience, a similar strap would be used on the other side of the interface body or the same strap could extend to both sides of the interface body 200.

Figure 27:
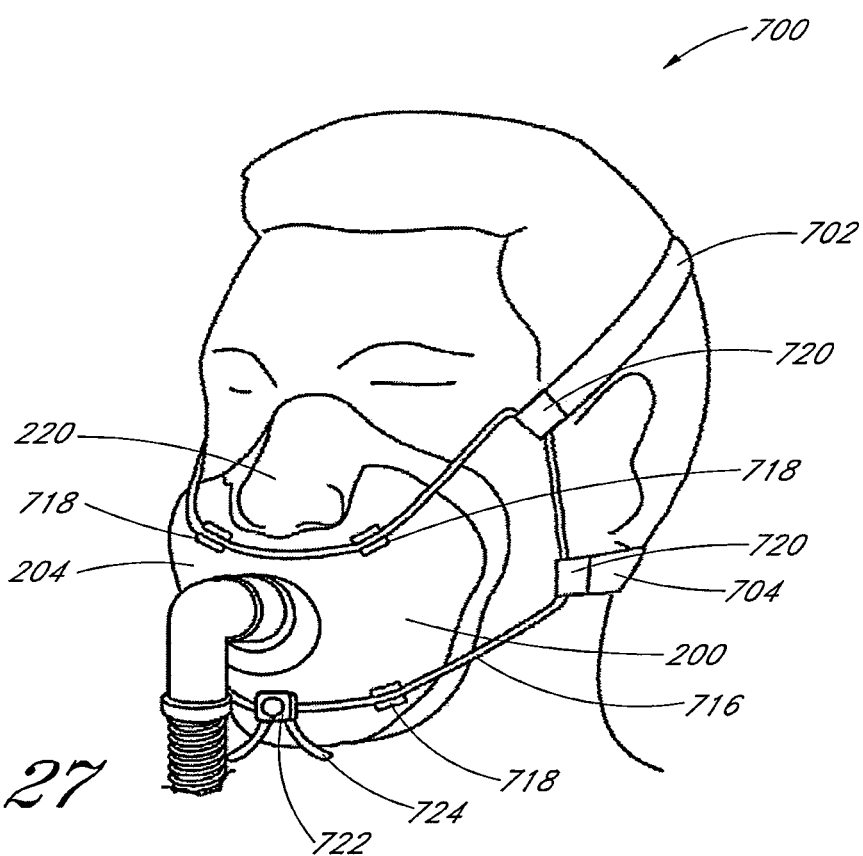
FIG. 27 is a front perspective view of a further interface, which generally includes a modification of the interface body of FIG. 2, fitted to a user using headgear that is arranged and configured in accordance with certain features, aspects and advantages of the present invention. The illustrated interface is shown with a breathing tube or supply conduit attached.

With reference now to FIGS. 13, 22 and 27, further examples of headgear assemblies 700 are shown that can be used to mount the interface body 200 on the patient. These headgear assemblies 700 are provided for illustration and other headgear types may be equally suitable.

Slots and Hook and Loop Fasteners

In the example of FIG. 22, the headgear assembly 700 comprises includes an upper strap 702 and a lower strap 704. The upper strap 702 extends around the back of the head of the patient above the ear. The lower strap 704 extends around the back of the neck of the patient below the ear.

Each strap 702, 704 is secured to the supporting member 204 of the interface body 200. The straps 702, 704 may be secured to the supporting member 204 by passing through clips. However, in some configurations, the straps 702, 704 may be secured to the supporting member 204 with slots 706 that can be formed through the supporting member 204. In particular, free ends 708 of the straps 702, 704 can pass through the slots 706. The free ends 708 of the straps 702, 704 can be secured, for example but without limitation, by hook and loop fasteners such as Velcro® or the like, back onto the remainder of the strap. Other suitable termination techniques also can be used.

In some configurations, the upper strap 702 can be secured to the supporting member 204 at a lower region while the lower strap 704 can be secured to the supporting member 204 at an upper region. In such configurations, the straps 702, 704 cross over at the side of the head of the patient.

Interface Body with Integrated Strap Portions

With reference to FIG. 13, the illustrated supporting member 204 comprises integral extended strap portions such as upper extended strap portions 710 and lower extended strap portions 712. Each extended strap portion 710, 712 may terminate in an arrangement for securing a strap (e.g., the upper strap 702 and the lower strap 704). Such an arrangement can be provided in the form of a slot 714. Other arrangements are also possible. For example, the ends of the upper and lower headgear straps 702, 704 and the ends of the integral strap portions 710, 712 may be provided with suitable complementary connectors, buckles and holes, or the like.

Single Point Adjustment

FIG. 27 illustrates a further configuration for headgear assemblies 700 in which the headgear assembly 700 can be more easily adjusted. Adjustment for desired positioning and/or tensioning of the interface body 200 is desired. Current approaches to provide adjustability use a combination of adjustable mechanisms, such as the hook and loop ends described with respect to FIGS. 22 and 13, for example but without limitation. The combination of adjustable mechanisms are connected to two, three, four or more discrete anchoring points on the interface body 202. Each connection to each anchoring point needs to be adjusted in a separate process, which makes achieving generally symmetrical positioning and loading of the interface body 200 a challenge.

With reference to FIG. 27, the illustrated headgear assembly 700 and adjustment system incorporates at least one sliding connection between the headgear assembly 700 and the interface body 200. Preferably, the at least one sliding connection comprises an upper sliding connection between the upper strap 702 and an upper portion of the interface body 200 and a lower sliding connection between the lower strap 704 and a lower portion of the interface body 200.

The sliding connections may comprise a line 716 passing across the outer surface of the interface body 200. The line 716 connects to the headgear straps 702, 704 on each side of the interface body 200. The line 716 can be slidably secured within sliding clips 718 on the exterior of the supporting member 204. Preferably, the chosen materials for the line 716 and the clips 718 allow a low friction contact to enable easy relative movement or sliding of the line 716 relative to the clips 718. In some configurations, the line 716 can be completely or partially enclosed within a lumen of a hose or tube to protect the sliding mechanism and/or to reduce the likelihood of objects (e.g., hair) becoming caught in the adjustment mechanism.

The clips 718 preferably capture the line 716 to reduce the likelihood of the line 716 separating from the clips 718 or the interface body 200. The captured but slidable line 716 enables the headgear and the interface body 200 to remain connected when the interface body 200 is removed from the head or face, for example. Preferably, the clips 718 allow removal of the interface body 200 from the line 716 if desired while the line 716 remains attached otherwise and during normal use conditions.

The clips 718 preferably are positioned to guide the line 716 across the interface body 200 at a location below the level of the nasal portion 220. The clips 718 also may be used to provide a sliding interface between the ends of the lower strap 704. The lower clips 718 guide the line 716 across a lower portion of the interface body 200.

In some configurations, the clips 718 may comprise one or more rotating pulley wheels to further reduce friction and allow enhanced slidability (i.e., relative movement between the line 716 and the interface body 200). In this respect, the term "sliding" has been used to broadly describe the relative motion between the line 716 and interface body 200. Low friction in the circuit of the line 716 allows the line 716 to be kept in tension all around the circuit of a loop defined by the line 716 as the interface body 200 and/or the headgear assembly 700 moves on the face or head during use, for example but without limitation.

With reference to FIG. 27, the single adjustment line 716 passes through the sliding connections 718 to the interface body 200 and through sliding connections 720 on the right and left side portions of the headgear assembly 700. The two end portions of the adjusting line 716 can come together at a clasp 722. Ends 724 of the adjusting line 716 can be pulled laterally apart to further pull the adjusting line 716 through the clasp 722, which reduces the length of the loop of the adjusting line 716 and which tightens the fit on the patient (i.e., increases the tension). The clasp 722 can allow the adjusting line 716 to pass through upon application of sufficient tension. The clasp 722 can have any suitable form. In some configurations, the clasp 722 can comprise a retractable key ring-type of component, a clamp, a jam cleat, a cam cleat, a wheel, or a ski binding type ratchet mechanism or any other suitable adjustment mechanism.

In some configurations, only one end of the adjustment line 716 is adjustable through the clasp 722. The other end of the adjustment line 716 could be fixed or anchored. In some configurations, the other end of the adjustment line 716 is fixed to the clasp 722, to the interface body 200, the one or more of the straps, or to the interface body 200 along with the clasp 722, for example but without limitation.

In some configurations, the clasp 722 may have a predetermined or adjustable limit to how much tension in the loop it can resist. In such configurations, the clasp tension limit can be used to set a limit to how much force the retention system can exert on a user's face. The clasp 722 may also be a wheel rotatably fixed to the support member 204 with the adjustment line 716 wound on about the wheel such that rotation of the wheel in one direction tightens the loop defined by the adjustment line 716 while rotation of the wheel in the other direction loosens the loop defined by the adjustment line 716. In this embodiment, a ratchet and release mechanism can be incorporated to hold the line 716 in place when adjustment to the wheel is not being made (i.e., with the release mechanism locked).

In some configurations, the interface body 200 and the loop of the line 716 may include only a single clip 718 that is positioned along the upper portion of the support member 204. Preferably, the single clip 718 is positioned along or fairly close to the medial plane. In some configurations, several clips 718 may be distributed along the interface body 200 and the line 716 may be routed to extend through only a portion of the several clips 718. In this manner, the shape of the loop defined by the line 716 can be varied. As a result, the angle of the line 716 extending towards the headgear strap portions 720 can be controlled and the loop defined by the line 716 can be routed around the ears or other anatomical features of the patient to improve comfort and/or fit.

As described, the headgear assembly 700 shown in FIG. 27 and described above features a single and simple adjustment for the interface-to-headgear connection. In other words, a single adjustment point can be effective in reducing and/or increasing the effective size of the patient interface to fit users of varying sizes and anatomical geometries. In addition, the single point of adjustment is all that is required to adjust the tension of the interface. In particular, the single point of adjustment in the illustrated configuration allows the interface and the headgear to remain symmetrically positioned on the face during and after adjustment of the tension in the line 716 while also allowing some gliding movement during use and during pressurization of the inflating seal.

One of the advantages of the interface body 200 and the headgear 700 featuring the line 716 is that the adjustments of the interface body 200 and/or the headgear assembly 700 can be made when the headgear assembly 700 and the interface body 200 is in position on the head and face. This greatly improves the ease of use of the interface body 200 and the headgear assembly 700 and allows for simplified adjustments to be made, which provides added comfort to the patient. Quick attachment and adjustment of the interface body 200 allows therapy to begin as soon as possible. Moreover, this adjustment system finds application with many different headgear configurations and many different types of patient interfaces.

Easy-Fit Headgear

FIG. 26 illustrates a headgear assembly 700 that can be quickly and easily placed onto a patient and/or adjusted by at least one of the patient or healthcare provider.

With most interface bodies, but particularly with the interface body 200 that comprises an inflating type seal, the headgear assembly 700 preferably has only a small amount of stretch. In other words, the headgear assembly 700, where it connects to the interface body 200, preferably has no stretch or virtually no stretch. However, interfaces that have the inflating seal can be especially difficult to fit with an appropriate level of tension pulling the interface body 200 onto the face of the patient. For example, if the interface body 200 is fitted to the patient with no breathing gases flow delivered to the interface body 200, the tension applied to keep the interface body 200 comfortably on the patient's face may not be sufficient to reduce the likelihood of substantial leakage when the breathing gases are delivered.

With reference to FIG. 26, the patient P has the interface body 200 positioned over the mouth and nose. The headgear assembly 700 includes two generally inelastic connecting straps 730 on each side of the interface body 200 and two generally elastic connecting straps 732 on each side of the interface body 200. The connecting straps 730, 732 connect the interface body to the balance of the headgear assembly 700.

The inelastic connecting straps 730 are fixed to any suitable headgear 700, including an encircling headgear 734, at one end and the inelastic connecting straps 730 preferably are connected to the interface body 200 with an adjustment mechanism 736 that allows the length of the inelastic connecting strap 730 to be varied (i.e., allows adjustment of the length of the connection between the interface body 200 and the headgear 734). In some applications, the adjustment mechanism 736 may be located at the end of the inelastic connecting strap 730 that connects to the headgear 734 instead of the interface body 200. In any event, the adjustment mechanism 736 preferably is positioned in a location that allows manipulation while the head of the patient is resting on a pillow or other structure such that the adjustment mechanism 736 can be manipulated without moving the head of the patient P.

The adjustment mechanism 736 may comprise any suitable structure. In some configurations, the adjustment mechanism 736 comprises a friction clasp that is fixed to the interface body 200 and through which the inelastic connecting straps 730 extend. The friction clasp can operate by a friction element that is biased to grip the connecting strap 730 to reduce the likelihood of the connecting strap passing through the friction clasp. When adjustment is required, the friction member can be disengaged from the connecting strap 730, thereby allowing the straps 730 to lengthen as desired. The friction clasp provides a simple mechanism 736 that can be easily operated with one hand. In some configurations, the adjustment mechanism 736 can comprise a ladder lock, a buckle, a ratchet, a clamp, a cam cleat or a post and hole engagement, for example but without limitation.

Many different types of adjustment mechanisms 736 can be provided to allow the length of the relatively inelastic connecting straps 730 to be adjusted. For example, while friction clasps and various forms of cam cleats may be particularly appropriate for configurations where the connecting straps 730 are rope, cord or the like, other forms of adjustment may be more appropriate, especially where the connecting straps 730 are semi-rigid. For example, a ski binding type ratchet mechanism or other clamp locking mechanism may be used as appropriate.

In some configurations, the adjustment mechanism 736 is of a locking type having at least two modes. In the first locking mode, the length of the substantially inelastic connecting straps 730 cannot be lengthened. In the unlocked mode, the length of the straps 730 can be adjusted in both directions (i.e., lengthened and shortened). In some configurations, the length of the straps 730 can be shortened when the respective adjustment mechanism 736 is in the locking mode but the length cannot be lengthened.

In some configurations, the locking mode may be operable to reduce the likelihood of lengthening and shortening adjustments of the respective straps 730. In some configurations, all of the adjustment mechanisms 736 are located on the interface body 200. Preferably, all of the adjustment mechanisms 736 are located on a forward facing surface of the interface body 200. Such positioning of the adjustment mechanisms 736 would facilitate length adjustment of the straps 730 while the patient P remains with the back of their head supported on a pillow, for example.

The relatively elastic upper and lower connecting straps 732 can be arranged in parallel with the relatively inelastic connecting straps 730 such that both sets of the straps 730, 732 extend between the interface body 200 and the headgear 734. In other words, the relatively elastic connecting strap 732 is fixed to the headgear 734 at one end and also is fixed to the interface body 200 at the other end. The connection locations of the relatively elastic straps 732 may substantially coincide with the connection locations of relative inelastic straps 730. In some configurations, however, the connection locations may be offset such that the inelastic and elastic straps 730, 732 respectively connect to the headgear 734 and the interface body 200 in differing locations.

The relatively elastic connecting straps 732 preferably are extensile (i.e., stretchable). In some configurations, the length of the relatively elastic straps 732 can be stretched to between approximately 1.5 times and approximately 3 times the un-stretched length. Preferably, the length of relatively elastic straps 732 can be stretched to approximately double the un-stretched or relaxed length. Preferably, the relatively elastic straps 732 are not adjustable in length in any way other than through stretching of the strap material.

The parallel arrangement of the relatively elastic straps 732 and the relatively inelastic straps 730 facilitates a two-stage fitting process. The relatively elastic straps 732 allow a coarse fitting before a final fitting is achieved using the relatively inelastic straps. In some acute care applications, it is desired that respiratory therapy is delivered to the patient as quickly as possible. In order to achieve quick initiation of treatment, a preferred fitting procedure begins with holding the interface body 200 to the face of the patient P before fitting the headgear assembly 700 over the head of the patient P. In some fitting methods, the fitting procedure occurs substantially in line with the head of the patient (i.e., substantially aligned with the mid-sagittal plane of the patient).

The method of fitting the interface body 200 to the patient P can comprise: (1) gripping the interface body 200 in one hand and the headgear assembly 700 in the other hand; (2) positioning the interface body 200 over the mouth and nose of the patient in order to deliver therapy as quickly as possible (i.e., the therapeutic airflow has begun); (3) pulling the headgear assembly 700 rearward over the head of the patient until a desired headgear position is approximated; (4) releasing the interface body 200 and/or the headgear assembly 700 while the relatively elastic straps 732 provide sufficient tension force to hold the headgear assembly 700 on the head and the interface body 200 on the face while the relatively inelastic connections remain loose; and (5) making a final adjustment of the headgear assembly 700 and interface body 200 with the relatively inelastic straps 730. During the final adjustment, the relatively inelastic straps 730 can be tensioned to a desired level by adjusting the length of the relatively inelastic straps 730 and securing the desired level/lengths with the adjustment mechanisms 736.

The parallel arrangement of the relatively elastic connecting straps 732 with the relatively inelastic connecting straps 730 allows the headgear assembly 700 to be fitted such that it will stay in place without human intervention before the final adjustment of the relatively inelastic straps 730. The relatively elastic straps 732 allow a large degree of movement between the interface body 200 and the headgear assembly 700 to enable the headgear assembly 700 to be fitted over the head and the ears of the patient P with considerable ease. The retention force provided by the relatively elastic straps 732 preferably is sufficient to retain the interface body 200 on the face of the patient and the headgear assembly 700 on the head of the patient during fitting. While it is not necessary to provide a sufficient tension to result in proper sealing of the interface body against the face with the relatively elastic straps 732, in some configurations, the elastic retention force provided by the relatively elastic straps 732 can be sufficiently high to enable sealing of the interface body 200 to the face during use. Nevertheless, it is preferable that the configuration allows a large range of patient head sizes to be accommodated easily.

The relatively inelastic connection straps 730 are provided to reduce the likelihood of stretching of the headgear assembly 700 during ventilation once the straps 730 have been adjusted to a desired tension/length. Slight stretching of elastic straps can cause the pressure within the mask to drop slightly. The slight pressure drop can generate a response from a ventilator such that a pulsing gases supply can result from the elastic stretching of headgear or a connection between the headgear and the interface. For this reason, a substantially inelastic headgear and connection between the headgear and the interface are desired. When used with interface bodies that have an inflating seal, the desired tension/length for the relatively inelastic connecting straps 730 can be set while gases are flowing to the interface body and while the seal member 202 is inflated.

While, in the above embodiment, the connection between the interface body 200 and the headgear assembly 700 is provided by both upper and lower straps on both sides of the interface body 200, a single set of parallel elastic and inelastic straps 732, 730 can be provided or the straps can be provided only on one side of the interface body 200. In some configurations, the parallel elastic plus inelastic strap arrangement can be provided to only one of the top or bottom strap sets on each side while a single strap (either elastic or inelastic) can be provided for the other. In some configurations, the parallel elastic and inelastic strap arrangement can be provided to only one side of the interface body while the other is only a single strap (either elastic or inelastic).

In addition, in some configurations, the parallel arrangement of elastic and inelastic straps 732, 730 can be provided with an arrangement having no upper and lower straps but only a single level strap. In some configurations, the top strap may be secured to the interface body at a lower region while the lower strap may be secured at an upper region. In such a configuration, the straps cross over at the side of the head of the patient.

The above-described method of fitting the interface body 200 to the patient P is illustrative only and may be altered and even be reversed. For example, the headgear assembly 700 may be fitted to the head of the patient P first and then straps and the interface body 200 may be stretched over the head of the patient P until the interface body 200 is approximately in position. Finally, the relatively inelastic connecting straps 730 can be tightened to the appropriate length, usually while gases flow is being delivered to the interface body.

Thus, in some configurations, the generally inelastic connecting straps 703 are adjusted to a longer length that is sufficient to easily fit the interface body 200 and the headgear assembly 700 over the head of the patient. The interface body 200 then is grasped in one hand and the headgear assembly 700 is grasped in the other hand. The headgear assembly 700 is positioned approximately on the head with one hand. The other hand stretches the relatively elastic straps 732 of the headgear assembly 700 by pulling the interface body 200 away from the headgear assembly 700. With the interface body 200 pulled away from the headgear assembly 700, the interface body 200 is moved down over the face of the patient to fit over the mouth and nose. Once released, the relatively elastic straps 732 provide sufficient retention force to hold the interface body 200 on the face of the patient and to hold the headgear assembly 700 in place on the head of the patient while the relatively inelastic connection straps 730 remain loose. In order to complete adjustment of the headgear assembly 700 and the interface body 200, the relatively inelastic connecting straps 730 are pulled through the adjustment mechanism 736 until the appropriate length/tension in the relatively inelastic connecting straps 730 is achieved.

Figure 28:
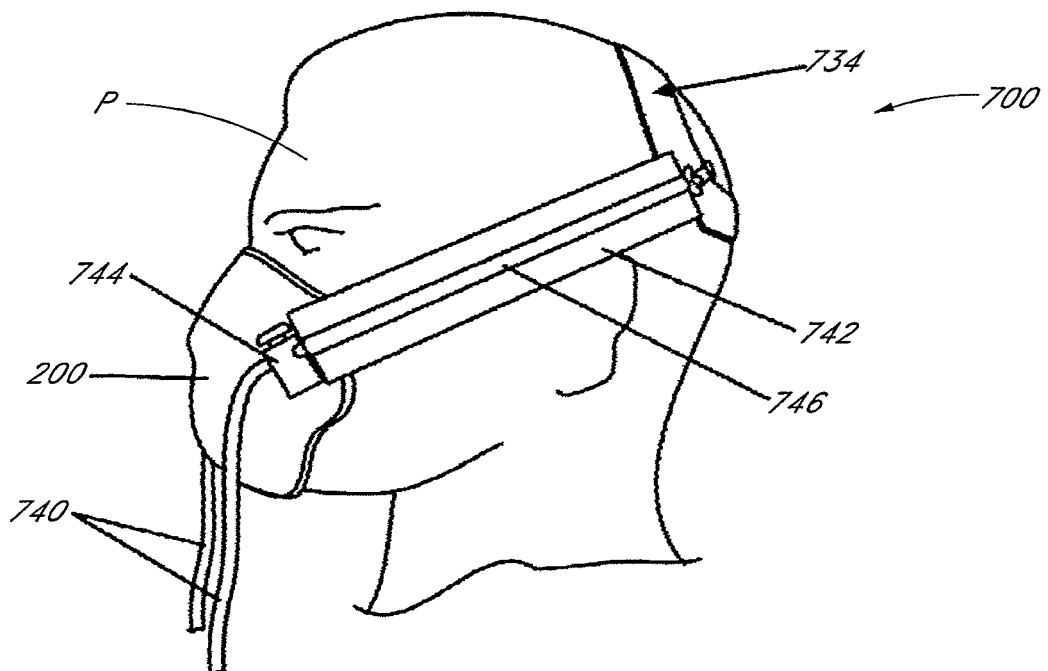
FIG. 28 is a side view of an interface and headgear that is arranged and configured in accordance with certain features, aspects and advantages of the present invention. The illustrated headgear includes integrated elastic and inelastic straps.

With reference to FIG. 28, a further configuration will be described in which the relatively inelastic connecting straps 740 are at least partially integrated with the relatively elastic connecting straps 742. The illustrated relatively inelastic connecting strap 740 comprises a substantially non-stretch strap and is fixed to the headgear 734 at one end. At the other end, the substantially non-stretch connecting strap 740 is connected to the interface body 200 via an adjustment mechanism 744 that allows the length of the connecting strap 740 to be varied. In the illustrated configuration, the elastic connecting straps 742 comprise a passage 746 that extends from one end to the other and within which the relatively inelastic connecting strap 740 is disposed. The adjustment mechanism 744 can comprise friction clasps or any other suitable adjustment mechanisms, including but not limited to those discussed elsewhere within this application. The adjustment mechanism preferably is mounted to the interface body 200 but can be positioned elsewhere if desired. An advantage of the illustrated embodiment in FIG. 28 is that the configuration is compact, visually unobtrusive and less likely to tangle the straps.

It is to be understood that this embodiment may include upper and lower straps or only one level of strap(s) between the headgear 734 and interface body 200. The embodiment of FIG. 28 comprises a locking mode for the relatively inelastic connecting straps 740 by the friction clasps 744 or other suitable adjustment mechanism. When in the unlocking mode, the relatively inelastic connecting straps 740 can be lengthened or shortened. When in the locking mode, the length of the connecting straps 740 are fixed or alternatively cannot be lengthened. When fitting the interface body 200, the connecting straps 740 and the respective adjustment mechanisms 744 provide a strain limiting effect, which reduces the likelihood of the distance between the interface body 200 and the headgear 734 increasing, while the more elastic connecting straps 742 provide a temporary retention force during coarse fitting.

Like previous embodiments, the arrangement illustrated in FIG. 28 may be fitted either interface body first or headgear assembly first. A preferred fitting procedure fits the interface body and the headgear assembly substantially in-line, as described previously, and begins with placing the interface body over the face of the patient in order to provide therapy immediately.

Figure 29:
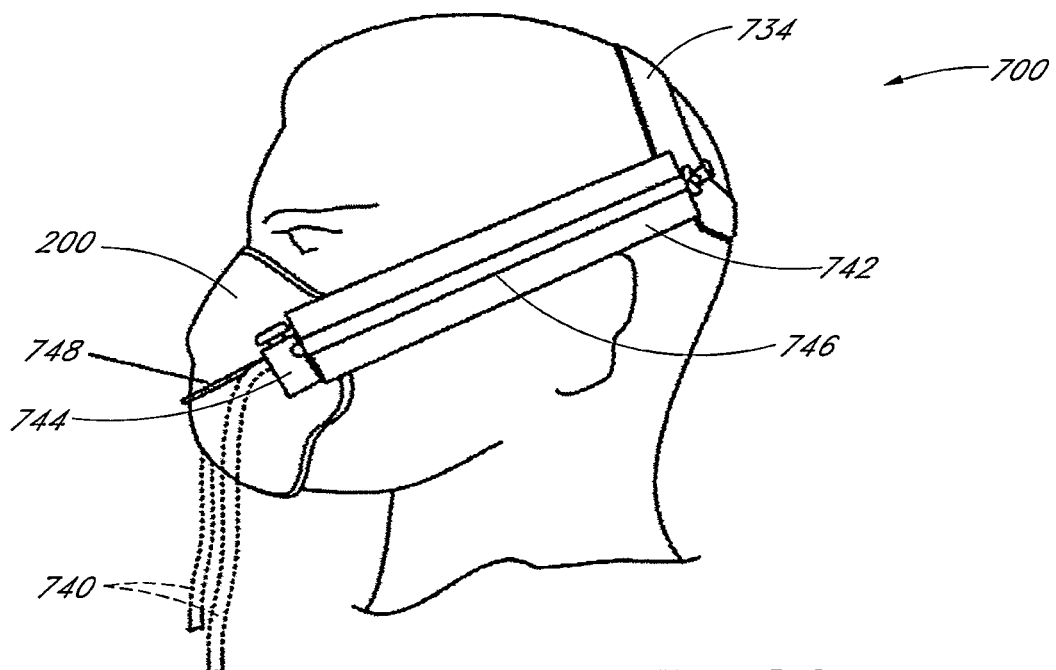
FIG. 29 is a side view of an interface and headgear that is arranged and configured in accordance with certain features, aspects and advantages of the present invention. The illustrated headgear includes integrated elastics and inelastic straps and a spine.

In some configurations, the relatively inelastic connecting member 740 may be replaced with, or may be supplemented by, as shown by dotted lines in FIG. 29, a substantially noncompressible/non-buckling spine member 748 that extends through the passage 746. In this embodiment, the spine member 748 provides a connection between the interface body 200 and the headgear 734 that generally resists both elongation and compression or buckling. In such a configuration, the spine member 748 preferably is semi-rigid such that it generally resists buckling and compressive forces, which allows the headgear to maintain an overall shape.

Especially in connection with a semi-rigid headgear assembly, it has been found that the shape holding, or self-supporting nature, can result in an overall assembly that is intuitive to fit. In particular, where the connection and/or headgear members are self-supporting such that they maintain a three-dimensional form, the headgear can be fitted in the correct orientation with very little if any instruction. In a self-supporting arrangement, the tendency of the straps to not tangle also reduces the time taken to fit the overall assembly.

The semi-rigid nature of the spine 748 allows the connection length between the interface body 200 and the headgear 734 to be shortened by a simple process. For example, when the spine 748 is used in place of a rope or cord, the connection length with the adjustment mechanism 744 in an unlocked position may have a tendency to shorten "automatically" in response to the retention force of the elastic connecting strap 742. This feature further aids the simplicity of the procedures used to don and/or doff the system.

Semi-Rigid Headgear

Figure 30:
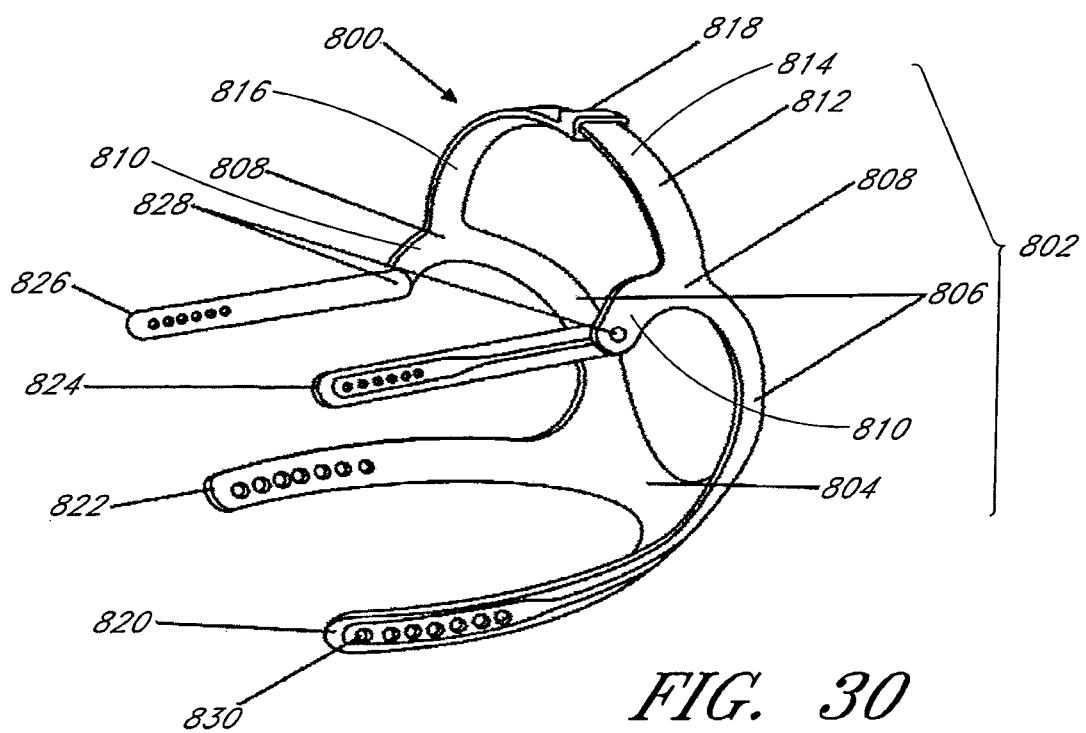
FIG. 30 is a perspective view of headgear that is arranged and configured in accordance with certain features, aspects and advantages of the present invention.

A further headgear embodiment for use with the patient interface 200 now will be described with reference to FIGS. 30 to 32. In the illustrated configuration, the headgear assembly 700 comprises a semi-rigid headgear assembly 800. It has been found that an advantage of the headgear assembly such as that illustrated in FIG. 30 is that, when not in use, the headgear assembly can maintain a substantially three-dimensional form. As a result, the fitting of the headgear assembly to the head of the patient is intuitive and may be accomplished consistently and accurately with little instruction or untangling before fitting.

As used herein, the term "semi-rigid" is used to denote that the headgear assembly is sufficiently stiff such that the assembled headgear assembly can assume a three-dimensional shape with dimensions approximating the head of the patient for which the headgear is designed to fit while also being sufficiently flexible to generally conform to the anatomy of the patient. For example, some of the other components (e.g., straps) of the headgear assembly may also be partially or wholly "semi-rigid" such that the components are capable of holding a three-dimensional form that is substantially 'self-supporting'. A "semi-rigid" headgear assembly is not intended to mean that each and every component of the headgear assembly is semi-rigid. For example, the substantially three-dimensional form that the self-supporting headgear assembly may assume may relate primarily to the rear and top portions of the headgear assembly. In addition, the "semi-rigid" headgear assembly may include semi-rigid regions that extend forward of the ears and above the ears when placed on the head of the patient.

The illustrated headgear assembly 800 generally comprises a first strap portion 802 that is adapted to engage the head of the patient. The illustrated first strap portion 802 generally comprises three sub-portions or regions: a lower rear region 804; side regions 806; and a top portion 812. In some configurations, at least the first strap portion 802 can be formed with contrasting colors between an inside surface and an outside surface such that twists in any portion that is so colored can be readily identified.

The lower rear region 804 is adapted to engage with the rear of head of the user. Preferably, the lower rear region 804 is adapted to engage with the head at a location on or below the external occipital protuberance. The lower rear region 804 spans the distance around the back of the head and extends to each side of the head. In some configurations, the lower rear region 804 comprises a longitudinal center that is adapted to be located about 25 degrees below a horizontal plane that extends through the ear canal of the patient.

On either side of the head, the first strap portion 802 extends upward into left and right side regions 806. The side regions 806 generally extend superolaterally (i.e., upwards and outwards). The side regions 806 are adapted to extend behind the ears of the patient. Preferably, the side regions 806 also are adapted to extend behind the mastoid processes of the patient. Each of the left and right side regions 806 of the first strap portion 802 extends into or comprises an arched portion 808. The arched portion 808 bends upward and forward. The arched portion 808 is adapted to extend over the respective ears of the patient. Preferably, each of the arched portions 808 terminates at a respective termination portion 810. The termination portions 810 preferably are adapted to be located forward of the ears of the patient. In some configurations, the side regions 806 and the arched portions 808 of the first strap portion 802 do not include a soft inner padding portion but may comprise a single, self-supporting, resilient material that is in direct contact with the head/hair of the patient.

The top portion 812 of the first strap portion 802 connects the arched portions 808 of the side regions 806. The top portion 812 can be positioned forward of the ears in some configurations. Preferably, the top portion 812 is positioned generally vertical from the ears. More preferably, a longitudinal center of the top portion 812 is adapted to be spaced about 13 mm rearward of a vertical plane that intersects the ear canals. In some configurations, the top portion 812 comprises a first segment 814 and a second segment 816 with the first segment 814 and the second segment 816 combining to form the top portion 812. The first segment 814 extends upward from an apex of the left arched portion 808 while the second segment 816 extends upward from an apex of the right arched portion 808. Preferably, the top portion 812 is formed of a self-supporting and resilient material. In some configurations, the top portion 812 does not include any backing, including a soft padded backing layer.

The first segment 814 and the second segment 816 can be connected with any suitable connector 818. The connector 818 can comprise an adjustment mechanism such that the first and second segments 814, 816 are adjustably connected. The adjustment mechanism of the connector 818 preferably is substantially flat on its underside to improve comfort. Preferably, the adjustment mechanism can be adjustable to account for small size variations such that a range of sizes can be accommodated. For example, the connector 818 may comprise a series of spaced apertures on the first segment 814 and one or more posts projecting upwards and located on the second segment 816. In some configurations, the apertures and posts provide an adjustment pitch of about 20 mm with one, two, three or more possible positions. This type of adjustment mechanism allows the length of the top portion 812 to be simply adjusted by pushing the post through the appropriate aperture.

While, in some configurations, the first and second segments 814, 816 are integrally formed (i.e., the top portion 812 is a single strap that is permanently or semi-permanently connected to the arch portions 808) and, in some configurations, the first and second segments 814, 816 are non-adjustably connected, the illustrated configuration allows adjustment for customization of the headgear assembly 800 to the patient.

With continued reference to FIG. 30, at least the arch portions 808 preferably are sufficiently stiff to resist significant deformation or displacement. In other words, the arch portions are sufficiently stiff to resist opening of the arch when a load is applied at or about the termination portions 810 in a forward direction. The applied load corresponds to a strap tension force that may be experienced with the interface body 200 is in use with breathing gases being delivered to the patient while the headgear assembly 800 is worn by the patient, for example but without limitation. Preferably, the termination portion 810 is configured to be strong enough to carry a load and exhibits bending behavior consistent with the following equation: $[(t*w^3)/12]*TS>2400$, where t is thickness of the material, w is the width of the strap and TS is the tensile strength of the material used to form the strap. Preferably, at least the remainder of the first strap portion 802 of the headgear assembly 800 (e.g., the arch portions 808, the side regions 806, the top portion 812 and the lower rear region 804) are configured to satisfy the following two equations: (1) $[(w*t^3)/3]*FM<6,250$, where t is thickness of the material, w is the width of the strap and FM is the flexibility modulus of the material used to form the strap; and (2) $[(w*t^3)/12]*TS<24$, where t is thickness of the material, w is the width of the strap and TS is the tensile strength of the material used to form the strap. In addition, the strap width preferably is at least 25 mm. In some configurations, the strap width is about 30 mm. In some configurations, the strap has a thickness of about 1 mm.

With reference again to FIG. 30, a left lower strap 820 and a right lower strap 822 each extend from a respective side of the lower rear region 804. The left lower strap 820 and the right lower strap 822 preferably extend forward from the lower rear region 804. More preferably, the left and right lower straps 820, 822 are adapted to extend forward at a location below the ears of the patient.

The left and right lower straps 820, 822 may be formed of a semi-rigid material or may be of a conformable material and not semi-rigid. Where used herein, the semi-rigid materials may include molded plastic or sheet materials that include but are not limited to homogeneous plastic materials and bonded non-woven fiber materials. Where the lower straps 820, 822 are semi-rigid, it is preferable that they are formed integrally with at least the lower rear region 804. In some configurations, however, the lower straps 820, 822 can be formed separately and can be permanently, semi-permanently or removably secured to the lower rear region 804. Preferably, the right and left lower straps 820, 822 are formed as an integrated component that, in use, will extend around the back of the head and/or neck of the patient. The integrated component can be integrally formed with the lower rear region 804 or can be formed separate of the lower rear region 804 and secured to the lower rear region in any suitable manner. Forming the right and left lower straps 820, 822 in a single piece advantageously reduces that likelihood that one of the straps 820, 822 separating from the lower rear region 804 in a failure mode will release the interface body 200 from the face of the patient because the integrated straps 820, 822 will still be secured around the back of the neck or head of the patient even if the integrated straps 820, 822 become separated from the lower rear region 804.

A left upper strap 824 and a right upper strap 826 respectively extend from the respective termination portions 810. Preferably, the upper straps 824, 826 extend forward and around the side of the head of the patient. More preferably, the upper straps 824, 826 are adapted to extend in a region generally below the eye of the patient. The upper straps 824, 826 connect to the interface body 200.

In some configurations, the upper straps 824, 826 are formed separately from the first strap portion 802. The upper straps 824, 826 can be constructed of a semi-rigid material or of a conformable and/or compliant material. In some embodiments, the upper straps 824, 826 can be formed in a laminate structure comprising of soft padding (i.e., padding on the surface facing the head of the patient) and a generally inelastic portion (i.e., on the opposite side of the padding from the head of the patient). Such a configuration is shown in FIG. 30. Any of the lower straps 820, 822 or the upper straps 824, 826 may comprise a laminate structure such that the strap portion comprises a soft padding component at least on the inside of the strap that would contact the head/face of the patient. Preferably, at least the lower straps 820, 822 and, in some configurations the upper straps 824, 826 as well, are configured to support a maximum load of about 15 N from the holes of each strap. While the straps can be configured to support higher loads, supporting a maximum load of about 15 N provides a small sized strap that is sufficiently strong to counteract forces encountered when the mask is pressurized. Thus, the straps preferably are sized to counteract forces that result from pressurizing the interface 200.

As used herein with respect to headgear and straps, "soft" is used to describe a hand of the material, which means the quality of the material assessed by the reaction obtained from the sense touch. In addition, as used herein with respect to headgear and straps, "conformable" is used to describe the ability of the material to conform to the anatomical features of the patient (e.g., around a facial feature). In particular, a strap including at least an element of "soft" and/or "conformable" material also may be "semi-rigid" and/or axially inelastic.

The attachment of the upper straps 824, 826 to the respective termination portions 810 can be in any suitable manner. In some configurations, the attachment is made with a joint that will allow rotation of the upper straps 824, 826 about a pivot point 828 as shown for example in FIG. 31. The pivot point 828 can be located on the termination portions 810 at a location that is intersected by a plane that is about 33 degrees from vertical. In some configurations, the plane is about 33 degrees forward of a plane defined by the top portion 812. In some configurations, however, the upper straps 824, 826 may be otherwise connected to the first strap portion 802. In some configurations, the upper straps 824, 826 can be integrally formed with the arch portions 808 of the first strap portion 802.

Figure 34:
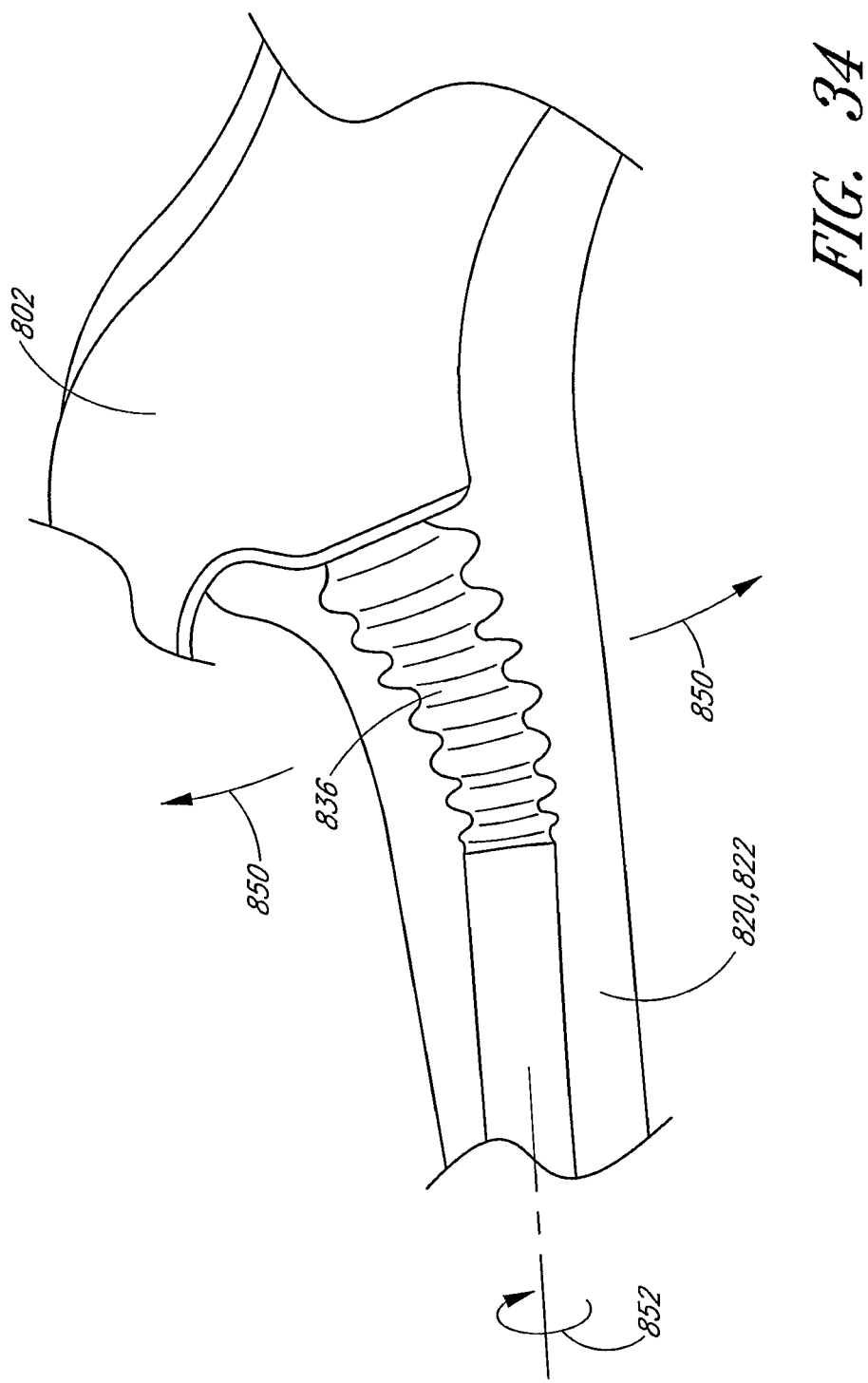
FIG. 34 illustrates a junction of a connection strap and the first strap portion of FIG. 30 with the first strap portion extending over at least a portion of the connection strap to provide strain relief and reinforcement.

With reference to FIG. 34, a junction between the lower straps 820, 822 and the lower rear portion 804 can be integrated, such as in the embodiment of FIG. 30. As shown in FIG. 34, the straps and the lower portion can be configured with a flexing region 836 to provide a degree of bend along its width (see arrows 850—which illustrate movement within the plane of the paper) and to provide a degree of rotation along an axial length (see arrow 852). These movements help the straps 820, 822 to conform to the anatomy of the patient while not significantly increasing bending in the thickness direction relative to a construction not having the flexing region 836. As illustrated in FIG. 34, the flexing region may include a grooved region, which has portions with material removed such that the flexing region 836 has the appearance of vertebrae that can bend and twist to improve the conformance of the straps 820, 822 to the anatomy of the patient while being reinforced by the first strap portion 802. Furthermore, the straps 820, 822 can reduce the likelihood of the reinforcing digging in to the patient or presenting a rigid edge to the patient. The reinforcement can be attached to the straps 820, 822 in any suitable manner, including but not limited to overmolding, welding, gluing, adhering, cohering, or the like.

In some configurations, such as that illustrated in FIG. 30, the above-described first strap portion 802 can be formed from a single flat member that assumes a three-dimensional headgear shape when the first and second segments 814, 816 of the top portion 812 are joined together. In some configurations, the first strap portion 802 and the lower straps 820, 822 are formed from a single flat member. In some configurations, the first strap portion 802, the lower straps 820, 822 and the upper straps 824, 826 all are formed from a single flat member. In some configurations, the first strap portion 802 and the upper straps 824, 826 all are formed from a single flat member. In some configurations, the first strap portion 802 is formed from a first single flat member and the first and second lower straps 820, 822 are formed from a second single flat member. The first and second single flat members can be secured together in any suitable manner. Moreover, in some configurations, one or more portions of the headgear assembly (e.g., the first strap portion 802) can be molded or otherwise formed as a three dimensional component.

The flat members may be of a self-supporting, resilient, substantially inelastic material, such as Santoprene, polyolefin, polypropylene, polyethylene, foamed polyolefin or non-woven polymer material for example but without limitation. In some configurations, the flat members are formed from the polyethylene or polypropylene families. The material can be a low density polyethylene such as Dowlex 2517, which is a linear low density polyethylene that has a yield tensile strength of 9.65 MPa, a break tensile strength of 8.96 MPa, and a flexural modulus—2% secant of 234 MPa. The flat member preferably is formed of a material such that the headgear assembly 800 is substantially shape sustaining under its own weight regardless of the orientation of the headgear assembly 800. In some configurations, the straps do not stretch more than approximately 6 mm under a 30 N tensile load. In some configurations, the straps do not stretch more than approximately 3 mm under a 30 N tensile load.

In some configurations, one or more of the straps or flat members could be formed from non woven polyolefin (NWP), which is bonded (e.g. overmolded or laminated) with a polyolefin. In such configurations, the overmolded polyolefin material provides the principle shape sustaining properties. In addition, the softer NWP material is adapted to contact the skin and provide a desired comfort level. Furthermore, the NWP material may assist in providing the desired load bearing properties, such as the desired tensile load bearing properties. In some configurations, the lower straps 820, 822 may comprise a soft material, such as non-woven polymer, for example but without limitation.

The above-described embodiments of the headgear assembly 800 provide a low-profile and comfortable headgear assembly 800 that has very little or substantially no stretch. For example, the headgear assembly can have a tensile modulus greater than about 10 kPa. More preferably, the headgear assembly can have a tensile modulus greater than about 20 kPa. With use of at least semi-rigid materials for the first strap portion 802 (i.e., the portions that engage the rear and top parts of the head), the assembled headgear is capable of holding a self-supported three-dimensional form. This feature, coupled with features described within this application, result in a headgear assembly that is intuitive to fit with little or no instruction. In particular, the speed of fitting has been found to be significantly faster than existing headgear designs.

With particular reference to FIG. 30, the illustrated lower straps 820, 822 and the illustrated upper straps 824, 826 include a series of adjustment apertures 830 to provide an adjustable mechanism for fitting the headgear assembly 800 to various configurations of the interface body 200. The interface body 200 preferably comprises posts 832 that are adapted to engage with the apertures 830 of the straps 820, 822, 824, 826. During manufacturing, the apertures preferably are formed using laser cutting, which cauterizes the material surrounding the apertures such that the durability of the apertures can be greatly increased in a simple to manufacture manner. The illustrated style of attachment and adjustment mechanism is effective in practice and provides an intuitive solution requiring little or no instruction. In particular, the location of the adjustment/connection to the interface body 200 advantageously is positioned on the surface of the interface body. Preferably, the location of the adjustment/connection to the interface body 200 is positioned on a laterally extending portion of the support member 204, which is formed on the outside surface of the interface body 200. Such a location provides easy access and facilitates the fitting/adjustment while the head of the patient is resting on a pillow, for example. In other words, the adjustment of the straps can take place at locations forward of the ears and, more preferably, forward of the rearward-most surface of the interface. The adjustment also lends itself to correct balancing of left vs right side strap length adjustments because of the finite number of positions defined by the apertures 830. The apertures 830 provided in the upper and/or lower straps (820, 822, 824, 826) can be very easily counted or visually matched to encourage symmetric fitting of the headgear. Moreover, because there is no doubling back of the strap during tensioning, such as might be found with the use of a slot and hook/loop component of FIG. 22 for example, the force that can be applied to the straps 820, 822, 824, 826 during fitting is significantly less. In other words, there is no multiplier effect possible with the attachment and adjustment mechanism illustrated in FIGS. 30-32.

In addition, the illustrated straps 820, 822, 824, 826 tend to present forward naturally due to the semi-rigid configurations. In some configurations, only a portion of the illustrated straps 820, 822, 824, 826 are formed of a semi-rigid construction. The portion can provide sufficient lateral or forward presentation to keep the straps from being hidden or tangled behind the head of the patient. In addition, in some configurations, the portion of the lower straps 820, 822 and the portion of the lower rear region 804 that connect are semi-rigid while the distal ends (i.e., the ends of the straps 820, 822 that connect to the interface body 200) are substantially more flexible, while remaining relative inelastic in an axial direction. The forward presenting nature of the straps 820, 822, 824, 826 makes positioning and alignment of the apertures 830 with the attachment posts 832 of the interface body 200 intuitive and easy. Where the straps 820, 822, 824, 826 are relatively long for a given patient, the straps 820, 822, 824, 826 may project forward significantly beyond the aperture 830 through which the post 832 extends. In this situation, it is possible to double the forward projecting strap 820, 822, 824, 826 back on itself and pass an additional aperture 830 over the post 832. The result is a neat and tidy arrangement where the excess strap length is retained on the interface body.

Figure 32A:
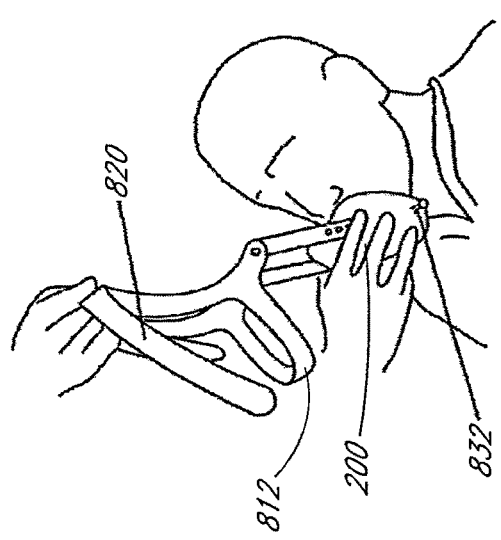
FIGS. 32(a)-32(d) illustrate a sequence of steps for fitting an interface and headgear that is arranged and configured in accordance with certain features, aspects and advantages of the present invention.
Figure 32B:
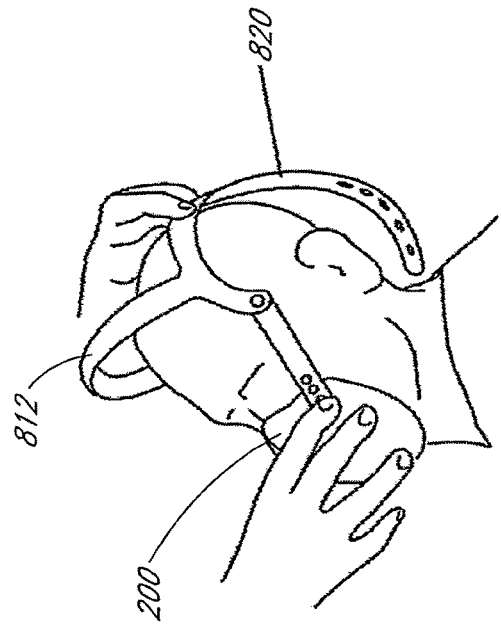
Figure 32C:
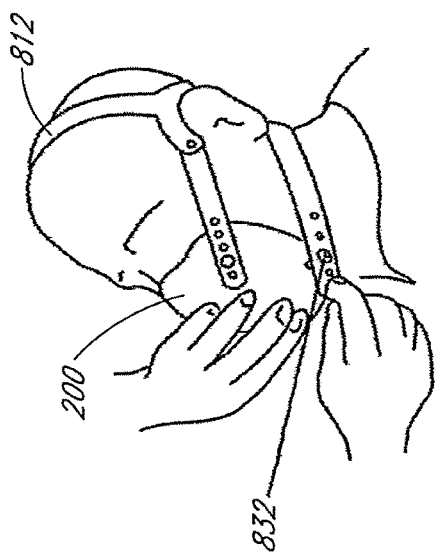
Figure 32D:
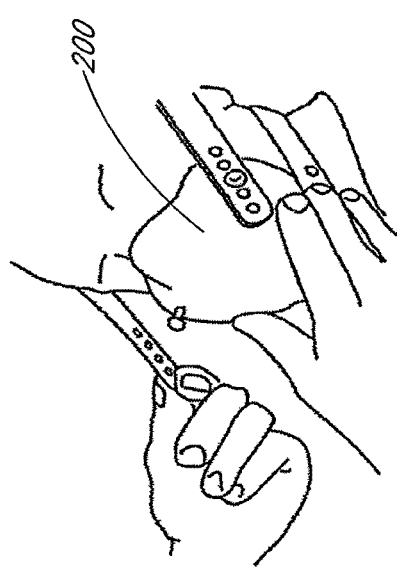

In one embodiment, it is preferred that the attachment between the upper straps 824, 826 and the patient interface 200 is semi-permanent. A fitting process with such an embodiment now will be described with particular reference to FIGS. 32A to 32D. In FIG. 32A, the healthcare provider takes the interface body 200 and places it on the face of the patient in order to deliver respiratory therapy immediately. When placing the interface body 200 onto the face, the interface body includes a sealing flange 208 as described above. The flange 208 includes a recess to accommodate, and/or locate on, the chin of the patient. Thus, when placing the interface body 200 onto the face, the chin is located within the recess and then the rest of the interface body 200 is brought into contact with the face. With the interface body in place on the face, the healthcare provider grips the headgear assembly 800, which is joined to the interface body by the upper straps 824, 826, with the other hand and raises the headgear assembly 800 over the head of the patient. As shown in FIG. 32B, the healthcare provider pulls the headgear assembly 800 down over the back of the head of the patient. The lower straps 820, 822 remain somewhat untangled and present around the side of the head due to the semi-rigid construction. In addition, the interface body 200 is loosely held against the face by the upper straps 824, 826. As shown in FIG. 32C, the healthcare provides connects the lower straps 820, 822 to the interface assembly by pushing the posts 832 through the appropriate apertures 830. If desired, the upper straps can be adjusted as shown in FIG. 32D. Final adjustments can be made to the upper straps 820, 822 and/or the lower straps 824, 826 to complete the final fitting. It will be appreciated that the foregoing steps need not necessarily be taken in the order recited.

Figure 31:
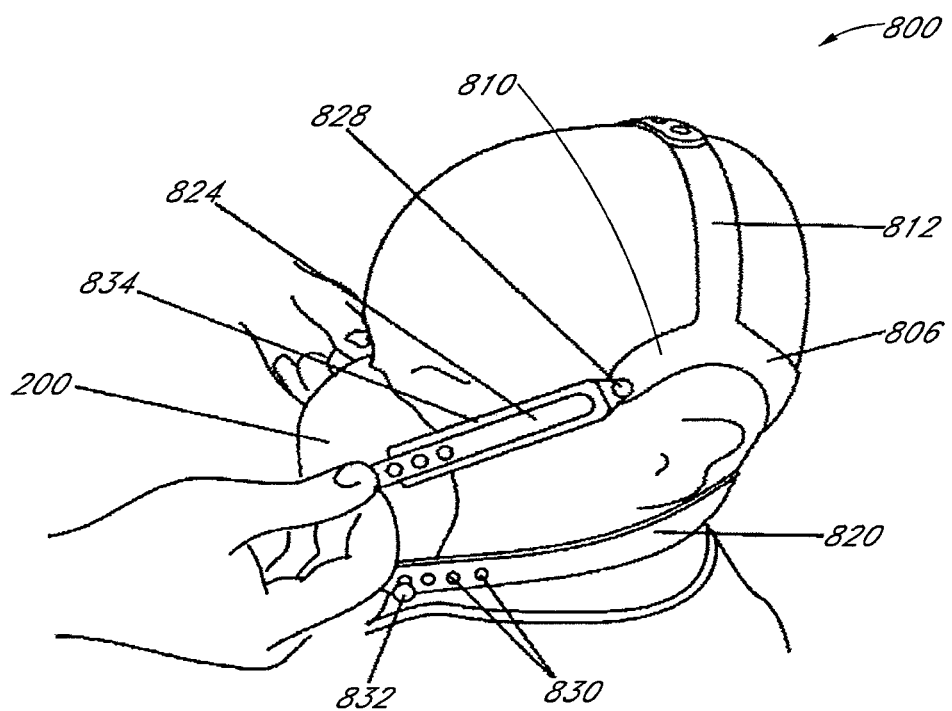
FIG. 31 is a perspective view of an interface and the headgear of FIG. 30 shown being fitted to a user.

With particular reference to FIG. 31, the headgear assembly 800 comprises substantially inelastic upper straps 824, 826 that are secured to the headgear assembly 800 at the pivot point 828. At the other end, the substantially inelastic connecting straps 824, 826 can be connected to the interface body 200 with an adjustment mechanism that allows the length of the straps 824, 826 to be varied. For example, the length of connection between the interface body 200 and the headgear assembly 800 can be adjusted by pushing the post 832 of the interface body 200 through an appropriate aperture 830 in each of the straps 824, 826. Each of the left and right side upper straps 824, 826 can comprise a stretchable elastic strap 834 that is secured to the headgear assembly 800 at one end and to the interface body 200 at other end in any suitable manner. Preferably, where parallel straps (i.e., elastic and inelastic straps in parallel) are used, the two straps are differently colored from each other to provide a contrast in color between the elastic and inelastic straps. The parallel arrangement of the elastic and non-elastic straps 824, 826, 834 facilitates a two-stage fitting process similar to that described earlier. A coarse fitting can be achieved with the elastic straps 834 before a final inelastic fitting is achieved using the inelastic straps 824, 826. In some configurations, the lower straps 820, 822 can be constructed in the same manner as just described.

Headgear

FIG. 33 illustrates a further headgear assembly 900. The headgear assembly 900 can be used in conjunction with a wide variety of patient interfaces, such as those described previously. In particular, the illustrated headgear assembly 900 is particularly suited to the configurations of the patient interface 200 described above. The headgear assembly 900 has been configured for easily donning and doffing, even for people with poor dexterity. In addition, the illustrated headgear assembly 900 is particularly easy and comfortable to put on and remove because there are no straps that extend under or behind the ears of the patient. In headgear assemblies that have straps that extend under the ears of the patient, those straps can catch on the ears of the patient while being removed or fitted.

The illustrated headgear assembly 900 comprises a top strap 902 that extends over the top of the head of the patient. The top strap 902 preferably lies substantially flat to the curve of the head of the patient. Preferably, the top strap 902 is adapted to be positioned over the top of the head of the patient at a location generally behind the ears.

The top strap 902 can comprise a side burn portion 904. The side burn portion 904 extends from the generally vertically extending top strap 902. Preferably, the side burn portion 904 extends from the top strap 902 at a position generally above the ears. The side burn portion extends downward and forward relative to the ears. The side burn portion 904 preferably terminates at a location below and in front the ears of the patient.

The headgear assembly 900 further comprises a back strap 906. The strap 906 can be pivotally connected at a pivot 908 to the top strap 902 at a location generally above the ears of the patient. The location of the pivot 908 preferably is in the vicinity of the connection between the generally vertically extending top strap 902 and the side burn portion 904.

Figure 33A:
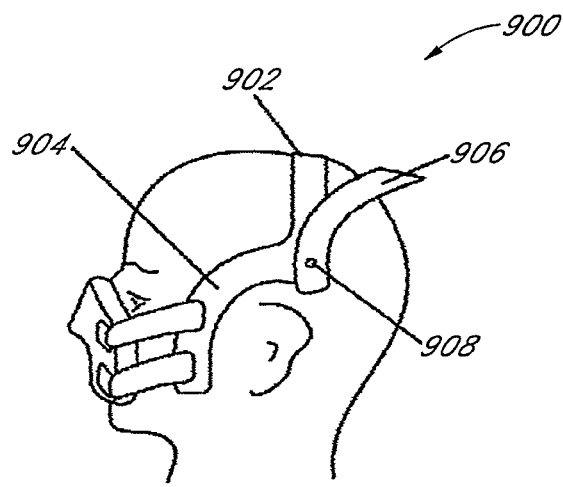
FIGS. 33(a)-33(d) illustrate a sequence of steps for fitting an interface and headgear that is arranged and configured in accordance with certain features, aspects and advantages of the present invention.
Figure 33B:
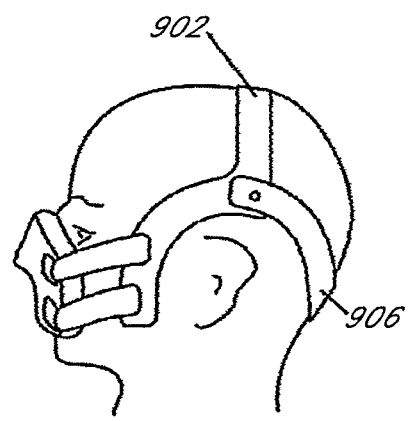
Figure 33C:
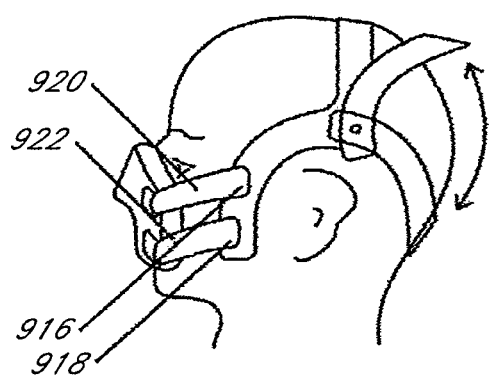
Figure 33D:
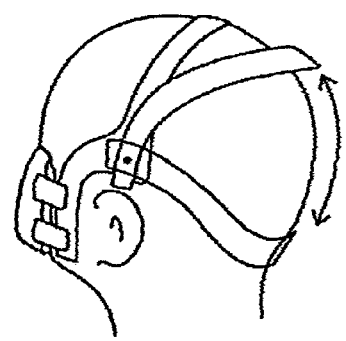

The pivot 908 allows the back strap 906 to rotate between two operating conditions. In a first operating condition, which is shown in FIG. 33A, the back strap 906 is pivoted upwards to disengage from the back of the head of the patient, which allows for easy removal of the headgear assembly 900. In a second operating condition, which is shown in FIG. 33B, the back strap 906 can be rotated downwards such that a lower rear portion of the back strap 906 engages with the rear of the head of the patient. Preferably, the lower rear portion of the back strap 906 is configured to engage the head of the patient at a position on or lower than the external occipital protuberance.

The back strap 906 and the top strap 902 can be provided with a locking mechanism that is operable to lock the back strap 906 in the lowered position, which is the position substantially as illustrated in FIG. 33B. In some configurations, the locking mechanism comprises a detent and a cooperating protrusion, which can be associated with one of the top strap and the back strap respectively. The detent and the protrusion preferably are reflected in matched sets that are located on both sides of the headgear assembly 900.

In some configurations, the top strap 902 can be provided with the protrusion while the back strap 906 is provided with the cooperating detent. As the back strap 906 is lowered into the position illustrated in FIG. 33B, the detent will align with the protrusion and the back strap 906 will lock into position, which will enable the back strap 906 to pull the interface body 200 onto the face of the patient with the straps.

To release the back strap 906 so that the headgear assembly 900 can be more easily removed, the protrusion can be spring biased and can be released by pushing against the biasing spring until the protrusion disengages with the detent. Alternatively, the back strap 906 can be lifted with sufficient force to overwhelm but not damage the locking mechanism. A number of other suitable locking mechanisms also can be used with the headgear assembly 900.

The side burn portions 904 of the illustrated headgear assembly 900 can provide attachment points 916, 918 from which the straps 920, 922 (i.e., the upper and lower straps respectively) can attach to the interface body 200. In some configurations, the headgear assembly 900 can include only a single strap between the interface body 200 and the headgear assembly 900 on each side of the side burn portion 904. In some configurations, the upper strap 920 can connect with a lower portion of the interface body 200 while the lower strap 922 can connect with an upper portion of the interface body 200 in a criss-cross fashion.

In some configurations, one or more of the straps 920, 922 can be formed of a stretchy elastic material. In some configurations, one or more of the straps 920, 922 can be formed of a substantially inelastic material. The top strap 902 and the side burn portions 904 can be formed of a semi-rigid, self-supporting material such that the headgear assembly 900 can assume a substantially three-dimensional shape and generally does not tangle. In addition, the back strap 906 can be formed of a semi-rigid, substantially self-supporting material. In some configurations, the material can comprise a laminate structure of both conformable and semi-rigid portions, for example but without limitation.

At least a portion of the top strap 902 and the side burn portions 904 can include padding to improve patient comfort. The back strap 906 also can include at least portions of padding to further improve patient comfort. The padding can take any suitable configuration that provides at least a layer of padding material on the inside of the headgear adjacent the skin and/or hair of the patient. In some configurations, the padding can be a soft layer of foam or other soft material. In some configurations, the semi-rigid headgear components can be completely or partially encapsulated by a soft material or can be over-molded with a soft material, for example but without limitation.

The foregoing description of the invention includes preferred forms thereof. Modifications may be made thereto without departing from the scope of the invention as provisionally indicated by the accompanying claims. In particular, it will be appreciated that the present invention describes a number of patient interface inventions (masks) as well as a number of headgear inventions and adjustment systems. While the specification gives a number of examples in which various interface embodiments are combined with various headgear embodiments, each and every possibility of the inventions are not explicitly given. It is intended that each and every combination of elements may be utilized alone or in combination as part of the present invention. Similarly, other known headgear and interface designs may also be used with the interface and headgear designs of the present invention respectively.

What is claimed is:

1. A headgear assembly used to secure a respiratory interface to a head of a user, the headgear assembly comprising:
   a first strap portion; and
   at least one connecting strap assembly, comprising:
      a relatively inelastic connecting strap; and
      a relatively elastic connecting strap,
      wherein the relatively inelastic connecting strap is at least partially integrated with the relatively elastic connecting strap,
      wherein the relatively inelastic connecting strap is fixed to the first strap portion at a first end of the relatively inelastic connecting strap, and a second end of the relatively inelastic connecting strap is connected to the respiratory interface via an adjustment mechanism such that the relatively inelastic connecting strap provides a connection between the respiratory interface and the first strap portion,
      wherein the adjustment mechanism allows a connection length of the relatively inelastic connecting strap between the first strap portion and the respiratory interface to be varied,
      wherein the relatively elastic connecting strap comprises a passage that extends from the first end to the second end and within which the relatively inelastic connecting strap is disposed.

2. The headgear assembly of claim 1, wherein the relatively inelastic connecting strap comprises a spine member that extends through the passage, the spine member providing the connection between the respiratory interface and the first strap portion, that generally resists both elongation and compression or buckling.

3. The headgear assembly of claim 2, wherein the headgear assembly is self- supporting such that it maintains a three-dimensional form.

4. The headgear assembly of claim 2, wherein when the adjustment mechanism is in the unlocking mode, the relatively inelastic connecting strap can shorten the connection length automatically in response to a retention force of the relatively elastic connecting strap.

5. The headgear assembly of claim 1, wherein the adjustment mechanism is configured to be mounted to the respiratory interface.

6. The headgear assembly of claim 1, wherein the adjustment mechanism comprises:
   a locking mode for the relatively inelastic connecting strap by the adjustment mechanism, wherein a length of the relatively inelastic connecting strap is fixed or alternatively cannot be lengthened such that the connection length between the respiratory interface and the first strap portion cannot be lengthened; and
   an unlocking mode, in which the relatively inelastic connecting strap can be lengthened or shortened such that the connection length between the respiratory interface and the first strap portion can be shortened.

7. The headgear assembly of claim 1, wherein the relatively inelastic connecting strap and the adjustment mechanism provide a strain limiting effect, which reduces a likelihood of a distance between the respiratory interface and the first strap portion increasing, while the relatively elastic connecting strap provides a temporary retention force during coarse fitting.

8. The headgear assembly of claim 1, wherein the at least one connecting strap assembly comprises a first connecting strap assembly and a second connecting strap assembly.

9. The headgear assembly of claim 8, wherein the first connecting strap assembly and the second connecting strap assembly are on each side of the respiratory interface.

10. The headgear assembly of claim 1, in combination with the respiratory interface, wherein the respiratory interface comprises a support member and a seal member, the seal member being connected to the support member.

* * * * *